(12) United States Patent
Skerra et al.

(10) Patent No.: US 10,406,247 B2
(45) Date of Patent: Sep. 10, 2019

(54) PSMA-SPECIFIC BINDING PROTEINS

(71) Applicants: TECHNISCHE UNIVERSITÄT MÜNCHEN, München (DE); BIOTECHNOLOGICKY USTAV AV CR, V.V. I., Vestec (CZ)

(72) Inventors: Arne Skerra, Freising (DE); Antonia Richter, Freising (DE); Volker Morath, Freising (DE); Cyril Barinka, Prague (CZ); Jakub Ptacek, Prague (CZ)

(73) Assignees: Technische Universität München, München (DE); Biotechnologicky Ustav AV CR, v.v.i., Vestec (CZ)

( * ) Notice: Subject to any disclaimer, the term of this patent is extended or adjusted under 35 U.S.C. 154(b) by 0 days.

(21) Appl. No.: 15/742,155

(22) PCT Filed: Jul. 6, 2016

(86) PCT No.: PCT/EP2016/065993
§ 371 (c)(1),
(2) Date: Jan. 5, 2018

(87) PCT Pub. No.: WO2017/005799
PCT Pub. Date: Jan. 12, 2017

(65) Prior Publication Data
US 2018/0318451 A1    Nov. 8, 2018

(30) Foreign Application Priority Data
Jul. 7, 2015 (EP) ................................. 15175735

(51) Int. Cl.
| | | |
|---|---|---|
| *A61K 38/17* | (2006.01) | |
| *A61K 49/00* | (2006.01) | |
| *C07K 14/47* | (2006.01) | |
| *C07K 7/06* | (2006.01) | |
| *C07K 7/08* | (2006.01) | |
| *C07K 14/705* | (2006.01) | |
| *C07K 19/00* | (2006.01) | |
| *C12N 15/62* | (2006.01) | |
| *G01N 33/533* | (2006.01) | |
| *G01N 33/574* | (2006.01) | |

(52) U.S. Cl.
CPC ........ *A61K 49/0017* (2013.01); *A61K 38/177* (2013.01); *C07K 7/06* (2013.01); *C07K 7/08* (2013.01); *C07K 14/4721* (2013.01); *C07K 14/4748* (2013.01); *C07K 14/705* (2013.01); *C07K 19/00* (2013.01); *C12N 15/62* (2013.01); *G01N 33/533* (2013.01); *G01N 33/57434* (2013.01); *C07K 2318/20* (2013.01); *C07K 2319/036* (2013.01); *C07K 2319/10* (2013.01); *C07K 2319/33* (2013.01); *C07K 2319/61* (2013.01); *C07K 2319/74* (2013.01)

(58) Field of Classification Search
None
See application file for complete search history.

(56) References Cited

FOREIGN PATENT DOCUMENTS

| WO | WO2012065978 A1 | 5/2012 |
| WO | WO2013174783 A1 | 11/2013 |

OTHER PUBLICATIONS

Richter, A. et al, "Anticalins: exploiting a non-ig scaffold with hypervariable loops for the engineering of binding proteins." FEBS Lett. (2014) 588 p. 213-218.*
Chang, Sam. S. et al, "Five different anti-protate specific membrane antigen antibodies confirm psma expression in tumor associated neovasculature." Canc. Res. (1999) 59 p. 3192-3198.*
Guilarte, Thomas R. et al, "Dysregulation of glutamate carboxypeptidsase II in psychiatric disease." Schizophr. Res. (2008) 99(103) p. 324-332.*
Richter, Antonia et al., "Neuartige biopharmazeutische Wirkstoffe auf der Grundlage von Lipocalinen" Biospektrum, Spektrum Akademischer Verlag, DE, vol. 20, No. 5, Sep. 3, 2014, pp. 503-505, doi:10.1007/S12268-014-0471-9.
Gebauer, Michaela et al., "Anticalins small engineered binding proteins based on the lipocalin scaffold" Methods in Enzymology 2012, vol. 503, 2012, pp. 157-188, doi:10.1016/B978-0-12-396962-0.00007-0.

(Continued)

*Primary Examiner* — Fred H Reynolds
(74) *Attorney, Agent, or Firm* — Perdue IP Law, APC

(57) ABSTRACT

The present invention relates to a prostate-specific membrane antigen (PSMA)-specific binding protein, wherein the PSMA-specific binding protein is a lipocalin 2 (Lcn2)-derived binding protein and binds to PSMA with a $K_D$ of 10 nM or lower. The present invention also relates to a nucleic acid molecule encoding the PSMA-specific binding protein of the invention, a vector comprising said nucleic acid molecule of the invention and a host cell transformed with the vector. Furthermore, the invention relates to a method of producing the PSMA-specific binding protein of the invention, the method comprising culturing the host cell of the invention under suitable conditions and isolating the PSMA-specific binding protein produced. The present invention further relates to a protein conjugate comprising the PSMA-specific binding protein of the invention, or the PSMA-specific binding protein produced by the method of the invention. In addition, the present invention relates to a pharmaceutical or diagnostic composition; to the PSMA-specific binding protein of the invention, the nucleic acid molecule of the invention, the vector of the invention, the host cell of the invention or the PSMA-specific binding protein produced by the method of the invention, for use in therapy and/or diagnosis, and in particular for use in the therapy and/or diagnosis of tumors, Crohn's disease and/or neurological diseases.

Figure 2A:
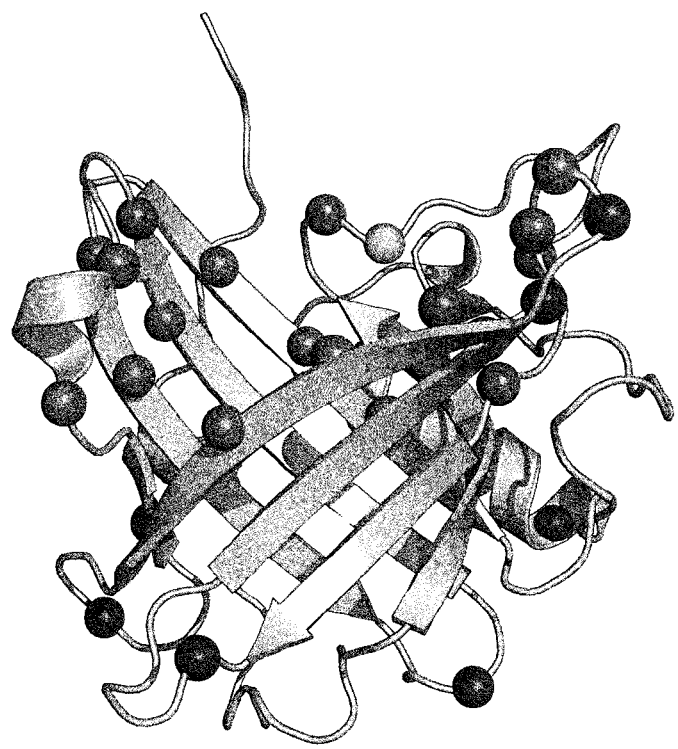

11 Claims, 10 Drawing Sheets
Specification includes a Sequence Listing.

(56) References Cited

OTHER PUBLICATIONS

Hohlbaum, A. M. et al., "Anticalins(R): The lipocalin family as a novel protein scaffold for the development of next-generation immunotherapies" Expert Review of Clinical Immunology, Future Drugs Ltd., London, GB, vol. 3, No. 4, Jan. 1, 2007, pp. 491-501, doi:10.1586/1744666X.3.4.491.

Schlehuber, S. et al., "Lipocalins in drug discovery: From natural ligand-binding proteins to 'anticalins'" Drug Discovery Today, Elsevier, Rahway, NJ, US, vol. 10, No. 1, Jan. 1, 2005, pp. 23-33, ISSN 1359-6446.

* cited by examiner

Figure 1A
Avi-PSMA:
```
           Avi-tag              TEV-site
RS GLNDIFEAQKIEWHE GSGSGS ENLYFQG RS-rhPSMA
```
SF-PSMA:
```
   Strep-tag II   FLAG-tag    TEV-site
RS WSHPQFEK DYKDDDDK ENLYFQG RS-rhPSMA
```
Figure 1B
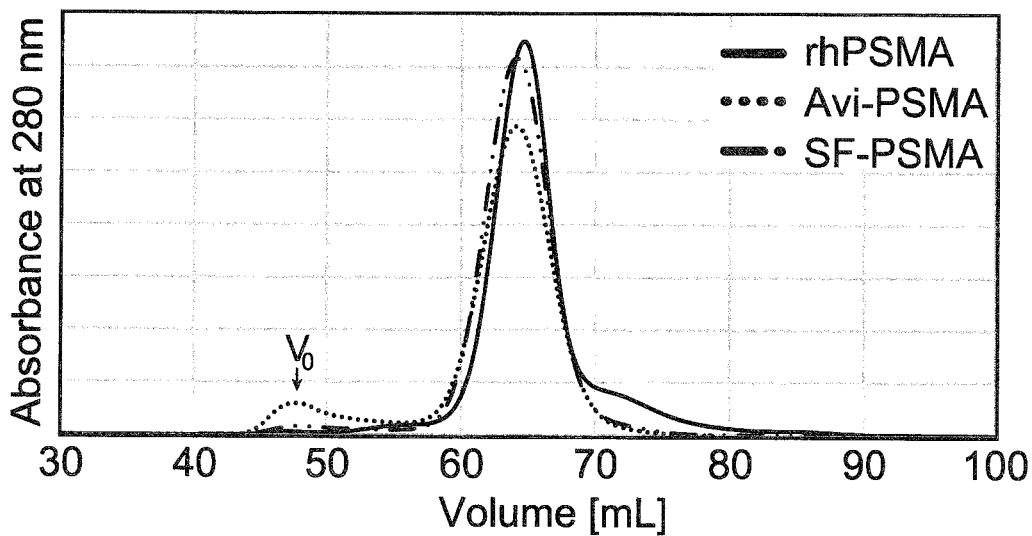
Figure 1C
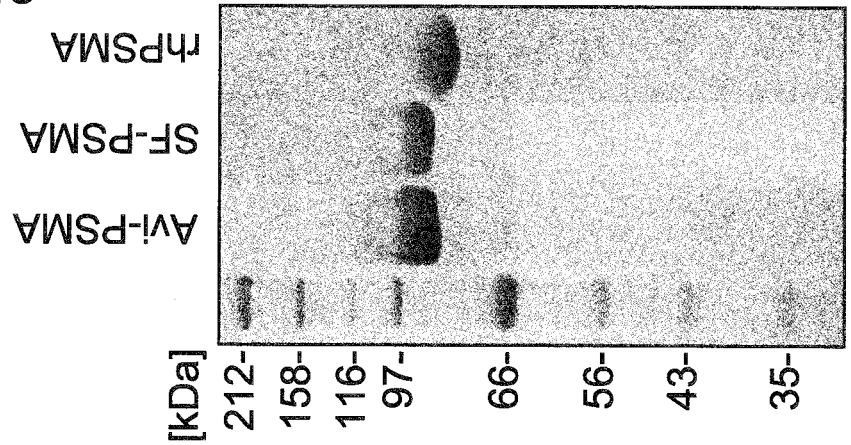

Figure 2C

```
          1           10         20         30         40         50         60         70         80         90        100
wtLcn2    QDSTSDLIPAPPLSKVPLQQNFQDNQFQGKWYVVVGLAGNAILREDKDPQKMYATIYELKEDKSYNVTSVLFRKKKCDYWIRTFVPGCQPGEFTLGNIKSY
Library   .............................h........x.....xx.....x..x.......x.x.xx...x.x.x....s.....x..x
A3        .............................h........M.....Y..S...x..x.......N.R.YL..Y.T.A....s.....x..T...G
A3A5      .............................h........V.....Y..S......................N.R.YL..Y.T.A....s.....x..T...G
A3A5.1    .............................h........V.....Y..S.........N............N.RYYL..Y.T.A....s.....Y..T...G
A3A5.7    .............................h........V.....Y..S......................N.R.YLN.Y.T.A....sR.....T...G
              ====A======          ===B====    ===C====     #2     ===D====  ==E===   #3
                        #1

101         110        120        130        140        150        160        170        178
wtLcn2    PGLTSYLVRVVSTNYNQHAMVFFKKVSQNREYFKITLYGRTKELTSELKENFIRFSKSLGLPENHIVFPVPIDQCIDG
Library   ...x...x............x.x.....E.Q...W.I.........................
A3        ...K...G............E.Q...W.I.........................
A3A5      ...K...G...........S........E.Q...W.I..........K...........
A3A5.1    ...D...G............E.Q...W.I.........................
A3A5.7    ...K...G............E.Q...W.I..........K...........
          ====F====         ===G====          #4            ===H===
```

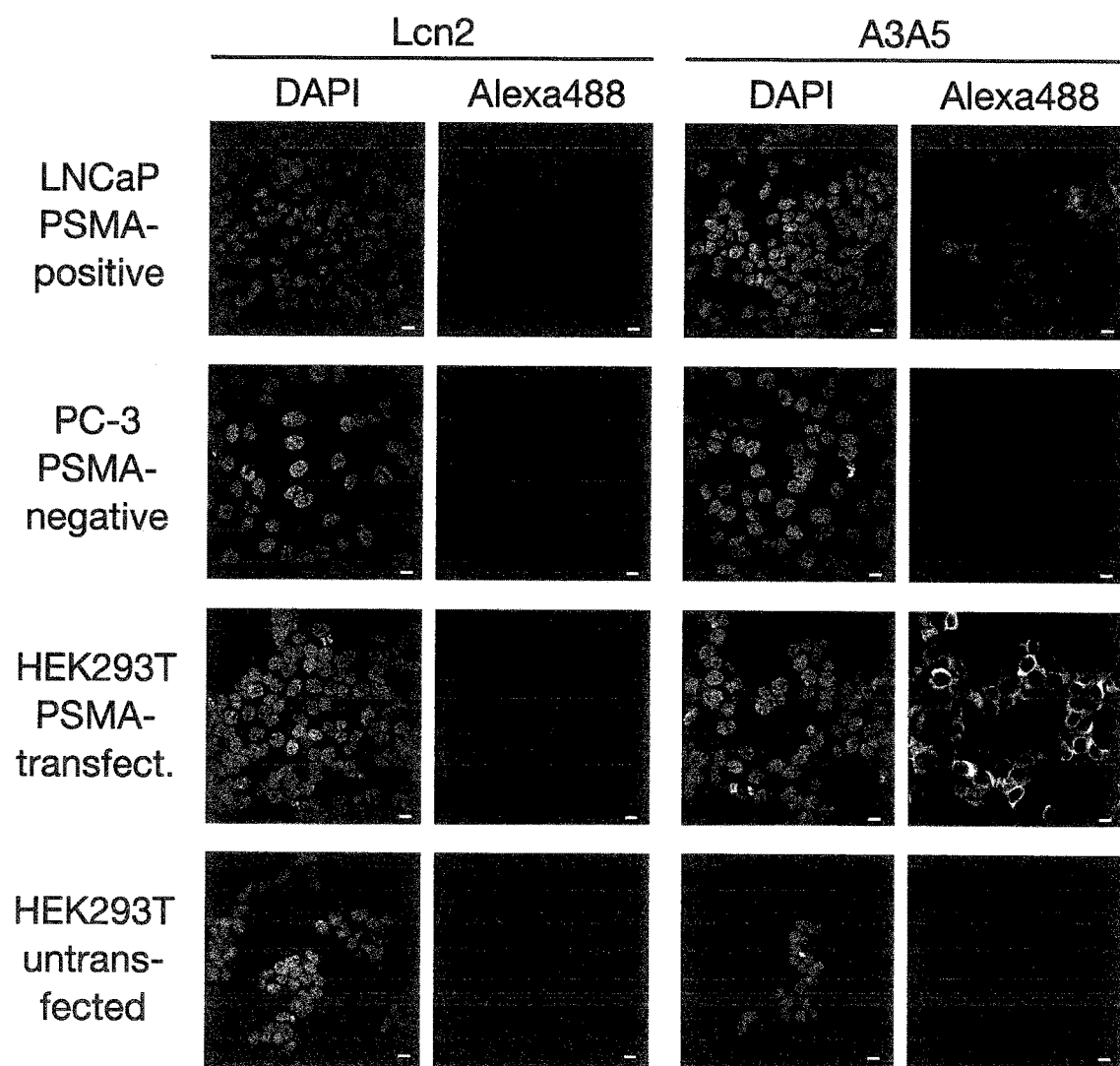

PSMA-SPECIFIC BINDING PROTEINS

CROSS-REFERENCE TO RELATED APPLICATIONS

This application is a national stage application under 35 U.S.C. § 371, of International Application No. PCT/EP2016/065993, filed Jul. 6, 2016, which claims benefit of priority to European Application No. 15175735.8, filed Jul. 7, 2015, each of which is incorporated herein by reference in its entirety.

SUBMISSION OF SEQUENCE LISTING

The sequence listing associated with this application is filed in electronic format via EFS-Web and is hereby incorporated by reference into the specification in its entirety. The text file containing the sequence listing, created on May 23, 2018, is named "Substitute_Seq_Listing_1111_107.TXT" and is 44 kB in size.

The present invention relates to a prostate-specific membrane antigen (PSMA)-specific binding protein, wherein the PSMA-specific binding protein is a lipocalin 2 (Lcn2)-derived binding protein and binds to PSMA with a $K_D$ of 10 nM or lower. The present invention also relates to a nucleic acid molecule encoding the PSMA-specific binding protein of the invention, a vector comprising said nucleic acid molecule of the invention and a host cell transformed with the vector. Furthermore, the invention relates to a method of producing the PSMA-specific binding protein of the invention, the method comprising culturing the host cell of the invention under suitable conditions and isolating the PSMA-specific binding protein produced. The present invention further relates to a protein conjugate comprising the PSMA-specific binding protein of the invention, or the PSMA-specific binding protein produced by the method of the invention. In addition, the present invention relates to a pharmaceutical or diagnostic composition; to the PSMA-specific binding protein of the invention, the nucleic acid molecule of the invention, the vector of the invention, the host cell of the invention or the PSMA-specific binding protein produced by the method of the invention, for use in therapy and/or diagnosis, and in particular for use in the therapy and/or diagnosis of tumors, Crohn's disease and/or neurological diseases.

In this specification, a number of documents including patent applications and manufacturer's manuals is cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Prostate carcinoma (PCa) is one of the most commonly diagnosed cancers in men. It is a cancer in the prostate, i.e. a gland in the male reproductive system and develops primarily in men over fifty. However, despite the common occurrence of prostate carcinoma, the presently available diagnostic and therapeutic modalities have limited efficacy. A recently published comprehensive validation of immunohistochemical biomarkers of prostate cancer showed that prostate-specific membrane antigen (PSMA) (together with AKT1, stromal androgen receptor, and EZH2) is one of only four markers that are independently prognostic for prostate-specific antigen (PSA) relapse following radical prostatectomy (Huber, F. et al. [2015] Brit. J. Cancer. 112:140-148).

PSMA is also known as glutamate carboxypeptidase II (GCPII) or N-acetylated-alpha-linked acidic dipeptidase (NAALADase) (Foss, C. A. et al. [2012] Curr. Med. Chem. 19:1346-1359; Barinka, C. et al. [2012] Curr. Med. Chem. 19:856-870) and is a membrane-tethered homodimeric metallopeptidase expressed in benign prostate secretory-acinar epithelium. Dysplastic and neoplastic transformation of prostate tissue is accompanied by a substantial increase in PSMA expression, with the highest levels observed in high-grade, metastatic, and hormone-insensitive cancers (Wright, G. L. et al. [1995] Urol. Oncol. 1:18-28). Apart from prostate carcinoma, increased PSMA expression has been observed also for subtypes of bladder carcinoma and Schwannoma (Wang, W. et al. [2009] Urol. Oncol. 27:525-528; Samplaski, M. K. et al. [2011] Mod. Pathol. 24:1521-1529), and PSMA is also detectable in the neovasculature of many solid tumors (Chang, S. S. et al. [1999] Cancer Res. 59:3192-3198; Haffner, M. C. et al. [2009] Hum. Pathol. 40:1754-1761). Therefore, bioactive molecules that target the neovasculature-restricted PSMA open excellent therapeutic opportunities and offer versatile diagnostic tools for the detection of many solid cancers, including prostate carcinoma.

Current imaging agents directed at PSMA fall into four categories, with the first two being the most advanced in the clinic: (i) antibodies, (ii) low molecular weight ligands, (iii) nanoparticles, and (iv) nucleic acid aptamers (Foss, C. A. et al. [2012] Curr. Med. Chem. 19:1346-1359; Mease, R. C. et al. [2013] Curr. Top. Med. Chem. 13:951-962).

At present, the only FDA-approved PSMA-specific imaging agent is a murine monoclonal antibody (mAb) radiolabeled with $^{111}$In known as ProstaScint (Ellis, R. J. et al. [2011] Int. J. Radiat. Oncol. Biol. Phys. 81:29-34). However, due to the fact that ProstaScint recognizes an intracellular epitope of PSMA it can only bind apoptotic or necrotic cells; consequently, this agent is not suitable for live cell staining, including the imaging of tumor neovasculature. This limitation was mitigated by the development of second generation mAbs which recognize extracellular epitopes of PSMA (David, K. A. et al. [2006] Clin. Genitourin. Canc. 4:249-256; Elsasser-Beile, U. et al. [2006] Prostate 66:1359-1370). The clinically most advanced agents are radio-metal conjugates of the murine mAb J591 (or its humanized form) that were shown to specifically image prostate carcinoma as well as other solid tumors in vivo (Vallabhajosula, S. et al. [2005] J. Nucl. Med. 46:634-641).

Nevertheless, mAbs in general suffer from several drawbacks as imaging agents, including poor tissue penetration and long circulation times, which causes significant background radioactivity within the blood pool and non-target tissues and, thus, poor imaging contrast (Mendler, C. T. et al. [2015] mAbs 7:96-109). One of the strategies for addressing the exceptionally slow pharmacokinetics of mAb-derived imaging agents is the use of smaller aptamers or PSMA-specific low molecular weight ligands. Phosphorus- and urea-based small molecule inhibitors having (sub)nanomolar affinities are most extensively investigated in this regard. These inhibitors typically comprise the P1' glutamate that is specifically recognized by PSMA, which is functionalized by a PET or SPECT radioisotope or an optical imaging agent. Such molecules did already prove efficacious in preclinical in vitro and in vivo models as well as in human clinical trials (Foss, C. A. et al. [2012] Curr. Med. Chem. 19:1346-1359; Afshar-Oromieh, A. et al. [2015] Eur. J. Nucl. Med. Mol. Imaging 42:197-209; Cho, S. Y. et al. [2012] J. Nucl. Med. 53:1883-1891; Barrett, J. A. et al. [2013] J. Nucl. Med. 54:380-387; Nedrow-Byers, J. R. et al.

[2013] Prostate 73:355-362; Ferraris, D. V. et al. [2012] Curr. Med. Chem. 19:1282-1294).

However, despite the fact that a lot of effort is currently being invested into the development of PSMA-specific research tools and theranostic agents, there is still a need to provide alternative PSMA-specific binding proteins that provide high target specificity, good tissue penetration as well as a tunable plasma half-life.

This need is addressed by the provision of the embodiments characterized in the claims.

Accordingly, the present invention relates to a prostate-specific membrane antigen (PSMA)-specific binding protein, wherein the PSMA-specific binding protein is a lipocalin 2 (Lcn2)-derived binding protein and binds to PSMA with a $K_D$ of 10 nM or lower.

Prostate-specific membrane antigen (PSMA) is a metallopeptidase that is a homodimeric class II membrane glycoprotein, with the larger part of the enzyme extending into the extracellular space. PSMA catalyzes the hydrolysis of N-acetylaspartylglutamate (NAAG) to glutamate and N-acetylaspartate (NAA) and is expressed in many tissues, including the prostate, kidney, the small intestine, and the central and peripheral nervous system. Human PSMA contains 750 amino acids and has a mass of approximately 84 kDa per monomer and is encoded in humans by the FOLH1 (folate hydrolase 1) gene.

Human PSMA mRNA is, for example, represented by the NCBI Reference Sequence: NM_004476.1 (as available on May 7, 2015) and human PSMA protein is, for example, represented by the UniProt ID Q04609 (as available on May 7, 2015).

The term "PSMA-specific binding protein" relates to a molecule that specifically binds (also referred to herein as "specifically interacts") to PSMA but does not or essentially does not cross-react with a different protein of similar structure. Cross-reactivity of a panel of molecules under investigation may be tested, for example, by assessing binding of said panel of molecules under conventional conditions to PSMA as well as to a number of more or less (structurally and/or functionally) closely related proteins. Only those molecules that bind to PSMA but do not or do not essentially bind to any of the other proteins are considered specific for PSMA. Corresponding methods are described e.g. in Harlow & Lane [1988] Antibodies: A Laboratory Manual, Cold Spring Harbor Laboratory Press; Harlow & Lane [1999] Using Antibodies: A Laboratory Manual, Cold Spring Harbor Laboratory Press.

The term "a molecule that essentially does not cross-react", as used herein, refers to a molecule that binds to PSMA with at least 5-times higher affinity than to a different protein of similar structure, more preferably at least 10-times higher affinity, such as e.g. at least 50-times higher affinity, more preferably at least 100-times higher affinity, such as e.g. at least 250-times higher affinity. Even more preferably, it binds with at least 500-times higher affinity to PSMA than to a different protein of similar structure and most preferably with at least 1.000-times higher affinity.

In accordance with the present invention, the PSMA-specific binding protein is a lipocalin 2 (Lcn2)-derived binding protein. Lipocalin-derived binding proteins, also referred to as Anticalins, represent a recently developed class of non-immunoglobulin binding proteins based on the human lipocalin scaffold. Lipocalins comprise a diverse family of small (20 kDa) extracellular proteins that occur in many species ranging from bacteria to humans and serve for the transport or scavenging of physiological compounds. Despite mutually low sequence homology, the three-dimensional fold of lipocalins is highly conserved (Schiefner, A. & Skerra, A. [2015] Acc. Chem. Res. 48, 976-985).

Their single chain molecular architecture is dominated by a compact eight-stranded anti-parallel β-barrel. At the open end of the barrel there are four loops connecting each pair of β-strands (see e.g. FIG. 2). The four structurally variable loops are referred to herein as "loop regions", whereas the remainder of the protein makes up the framework or "frame regions". Thus, similar to the structure of antibodies, the PSMA-specific binding proteins of the present invention are made up of conserved framework regions that are predominantly not directly involved in the binding to the target molecule, i.e. PSMA, as well as hypervariable, specificity-determining segments (here the loop regions, which are comparable to the CDRs in antibodies).

Lipocalin-2 (LCN2), also known as oncogene 24p3 or neutrophil gelatinase-associated lipocalin (NGAL), is a protein that in humans is encoded by the LCN2 gene. Human LCN2 mRNA is, for example, represented by the NCBI Reference Sequence: NM_005564.3 (as available on May 7, 2015) and human LCN2 protein is, for example, represented by the UniProt ID P80188 (as available on May 7, 2015).

The PSMA-specific binding protein of the present invention has been developed by structural modification of the Lcn2 molecule, i.e. it is a "lipocalin 2 (Lcn2)-derived binding protein". In a preferred embodiment, the PSMA-specific binding protein of the present invention is a binding protein derived from human lipocalin 2 (Lcn2).

In accordance with the present invention, the PSMA-specific binding protein binds to PSMA with a $K_D$ of 10 nM or lower.

The term "$K_D$" refers to the equilibrium dissociation constant (the reciprocal of the equilibrium binding constant) and is used herein according to the definitions provided in the art. Preferably, the PSMA-specific binding protein binds to PSMA with a $K_D$ of 5 nM or lower, such as e.g. 2 nM or lower, more preferably 1 nM or lower, and most preferably 0.7 nM or lower.

The $K_D$ value with which the PSMA-specific binding protein binds to PSMA can be determined by well known methods including, without being limiting, fluorescence titration, competition ELISA, calorimetric methods, such as isothermal titration calorimetry (ITC), flow cytometric titration analysis (FACS titration) and surface plasmon resonance (BIAcore). Such methods are well known in the art and have been described e.g. in (De Jong, L. A. A. et al. [2005] J. Chromatogr. B 829(1-2):1-25; Heinrich, L. et al. [2010] J. Immunol. Methods 352(1-2):13-22; Williams, M. A. & Daviter, T. (Eds.) [2013] Protein—Ligand Interactions, Methods and Applications, Springer, New York, N.Y.) as well as in the examples herein below.

Preferably, ELISA or competition ELISA or surface plasmon resonance (BIAcore) is employed to ensure that the $K_D$ of the PSMA-specific binding protein of the present invention is 10 nM or lower. Even more preferably, the $K_D$ is determined by surface plasmon resonance (BIAcore).

As discussed herein above, mAbs against PSMA are available in the art; however, as mentioned, such antibodies suffer from severe drawbacks as imaging agents, for example poor tissue penetration and long circulation times. These characteristics of mAbs cause significant background signal within the blood pool and non-target tissues and, consequently, provide poor contrast when employed for imaging purposes. The PSMA-specific binding proteins of the present invention, on the other hand, show good tissue penetration as well as a tunable plasma half-life, thereby overcoming the drawbacks associated with antibodies.

Moreover, these PSMA-specific binding proteins show remarkable target specificity, with dissociation constants in the nanomolar and even picomolar range. As is shown in the appended examples (e.g. Example 5), immunofluorescence microscopy confirmed the specific staining of PSMA-positive tumor cell lines, and cytofluorimetric/flow cytometric analysis further confirmed the ability of the PSMA-specific binding proteins of the present invention to detect PSMA on live cells. Due to their small and compact size, the PSMA-specific binding proteins of the present invention show a pharmacokinetic profile more similar to that of small-molecules that are currently preferred in clinical practice, while at the same time exhibiting high specificity similar to mAbs. Thus, the present PSMA-specific binding proteins offer a promising alternative to antibody-based PSMA binders for biomedical applications, including the therapy and diagnosis of tumors and neurological diseases, and in particular for the in vivo imaging of prostate carcinoma and/or the neovasculature of solid tumors.

Although a number of target-specific binding molecules derived from lipocalins were successfully reported in the art, the inventors encountered unexpected difficulties: initial attempts to generate PSMA-specific binding molecules/proteins conducted with a first PSMA target protein comprising an N-terminal Avi-tag (Avi-PSMA) and produced in insect cells were not successful (see Example 3). Upon further investigation, and as discussed in Example 2 below, it was shown by mass-spectrometric analysis that the PSMA ectodomain overexpressed in insect cells carried N-linked sugars with a combined mass of approximately 9.4 kDa (i.e. 12% of the polypeptide mass). Such a high degree of N-glycosylation could potentially mask/obstruct potential surface epitopes, thereby being responsible for the initial lack of success observed. However, a complete removal of N-linked sugars, e.g. by PNGase F treatment or by cultivating PSMA-expressing cells in the presence of tunicamycin, is known to be associated with the risk that partially misfolded protein preparations are obtained. Ultimately, these problems were successfully overcome by a combination of measures as detailed in the appended examples below, including for example the use of partially glycosylated PSMA as the target, which demonstrate that the PSMA-specific binding proteins of the present invention provide novel and promising PSMA-specific reagents that recognize this target protein in its native conformation.

In a preferred embodiment of the PSMA-specific binding protein of the invention, the PSMA-specific binding protein comprises or consists of frame regions and loop regions as represented in formula I:

Frame 1-Loop 1-Frame 2-Loop 2-Frame 3-Loop 3-Frame 4-Loop 4-Frame 5    (formula I), wherein the frame regions consist of the following amino acid sequences:
Frame 1 consists of an amino acid sequence consisting of the sequence of formula II:

$x_1$-(H/Q)-$x_2$    (formula II);

Frame 2 consists of an amino acid sequence consisting of the sequence of formula III:

S-$x_3$-(K/N)-$x_4$-N-$x_5$    (formula III);

Frame 3 consists of an amino acid sequence consisting of the sequence of formula IV:

Y-$x_6$-T-$x_7$-A-$x_8$-(S/C)-(Q/R)-$x_9$-(F/Y)-$x_{10}$    (formula IV);

Frame 4 consists of an amino acid sequence consisting of the sequence of formula V:

G-$x_{11}$-(N/S)-$x_{12}$    (formula V);

Frame 5 consists of an amino acid sequence consisting of the sequence of formula VI:

$x_{13}$-I-$x_{14}$-(E/K)-$x_{15}$    (formula VI);

wherein $x_1$ to $x_{15}$ consist of the following amino acid sequences or are a variant thereof:
$x_1$ consists of the amino acid sequence QDSTSDLIPAPPLSKVPLQQNFQDNQF (SEQ ID NO:8) or an N-terminal deletion fragment thereof; and
$x_2$ consists of the amino acid sequence GKWYVVGLA (SEQ ID NO:9);
$x_3$ consists of the amino acid sequence ATIYEL (SEQ ID NO:10);
$x_4$ consists of the amino acid sequence EDKSYNVT (SEQ ID NO:11);
$x_5$ consists of the amino acid V;
$x_6$ consists of the amino acid Y;
$x_7$ consists of the amino acid I;
$x_8$ consists of the amino acid sequence TFVPG (SEQ ID NO:12);
$x_9$ consists of the amino acid sequence PGE;
$x_{10}$ consists of the amino acid sequence TL;
$x_{11}$ consists of the amino acid sequence LVRVVSTNY (SEQ ID NO:13);
$x_{12}$ consists of the amino acid sequence QHAMVFFK (SEQ ID NO:14);
$x_{13}$ consists of the amino acid F;
$x_{14}$ consists of the amino acid sequence ITLYGRTKELTS (SEQ ID NO:15); and
$x_{15}$ consists of the amino acid sequence LKENFIRFSKSLGLPENHIVFPVPIDQCIDG (SEQ ID NO:16) or a C-terminal deletion fragment thereof;
and wherein the loop regions consist of the following amino acid sequence, or an amino acid sequence having at least 90% sequence identity thereto:
Loop 1 consists of the amino acid sequence consisting of the sequence of formula VII:

$y_1$-M/V-$y_2$-Y-$y_3$    (formula VII);

Loop 2 consists of the amino acid sequence consisting of the sequence of formula VIII:

R-(F/Y)-Y-L-(N/K)-$y_4$    (formula VIII);

Loop 3 consists of the amino acid sequence consisting of the sequence of formula IX:

$y_5$-$y_6$-G-$y_7$-(K/D)-$y_8$    (formula IX);

Loop 4 consists of the amino acid sequence consisting of the sequence of formula X:

E-$y_9$-Q-$y_{10}$-W    (formula X);

wherein
$y_1$ consists of the amino acid sequence GN;
$y_2$ consists of the amino acid sequence ILREDKDP (SEQ ID NO:17);
$y_3$ consists of the amino acid sequence KM;
$y_4$ consists of the amino acid sequence KC;
$y_5$ consists of the amino acid G;
$y_6$ consists of the amino acid sequence IKS;
$y_7$ consists of the amino acid sequence PG;
$y_8$ consists of the amino acid sequence TS;
$y_9$ consists of the amino acid V;
$y_{10}$ consists of the amino acid sequence QNRE (SEQ ID NO:18).

The term "comprising", as used in accordance with the present invention, denotes that further sequences/components can be included in addition to the specifically recited sequences and/or components. However, this term also encompasses that the claimed subject-matter consists of exactly the recited sequences and/or components.

In those embodiments where the PSMA-specific binding protein includes more than the recited amino acid sequence, additional amino acids extend over the specific sequence of formula (I) either at the N-terminal end or the C-terminal end or both. Additional sequences may include for example sequences introduced e.g. for purification or detection, as discussed in detail herein below.

It is a prerequisite that the binding affinity of the PSMA-specific binding protein to PSMA in the presence of these additional amino acids is retained or essentially retained. In accordance with the present invention, the binding affinity to PSMA is considered to be essentially retained if the difference or the ratio between the $K_D$ of the PSMA-specific binding protein comprising such additional amino acids and the $K_D$ of the same PSMA-specific binding protein without such additional amino acids is within two orders of magnitude, more preferably within one order of magnitude. Most preferred is that the binding affinity is fully retained, i.e. the $K_D$ of the PSMA-specific binding protein comprising such additional amino acids is equal or lower than the $K_D$ of the same PSMA-specific binding protein without such additional amino acids. Generally, a lower $K_D$ value corresponds to a higher or better affinity as is well known in the art. Therefore, also in accordance with the invention are PSMA-specific binding proteins having an increased binding affinity compared to the PSMA-specific binding protein without such additional amino acids.

Methods of assessing the binding affinity have been described herein above in connection with the discussion of the term "$K_D$" and include, without being limiting, fluorescence titration, ELISA or competition ELISA, calorimetric methods, such as isothermal titration calorimetry (ITC), flow cytometric titration analysis (FACS titration) and surface plasmon resonance (BIAcore).

The primary structure shown in formula I represents the order of the PSMA-specific binding protein of the present invention from the N-terminus to the C-terminus.

Frame 1 represents the most N-terminal part of the PSMA-specific binding protein of the present invention and its amino acid sequence is represented in formula II. Frame 5 represents the most C-terminal part of the PSMA-specific binding protein of the present invention and has the amino acid sequence represented in formula VI.

Throughout the present description, amino acid residues presented in the format "-(amino acid/amino acid)-", as used for example in Frame 1 for -(H/Q)-, represent two alternative amino acids suitable at the given position. In the example of Frame 1 this means that at the position following $x_1$ either a histidine (H) or a glutamine (Q) may be present.

Further in accordance with the present invention, the most N-terminal portion of Frame 1 (denoted $x_1$) encompasses the amino acid sequence QDSTSDLIPAPPLSKVPLQQNFQDNQF (SEQ ID NO:8) or an N-terminal deletion fragment thereof.

The term "N-terminal deletion fragment" refers to a fragment of the amino acid sequence of SEQ ID NO:8, in which one or several amino acids are lacking at the N-terminal end. Preferably, not more than 6 amino acids are lacking at the N-terminal end, more preferably not more than 5 amino acids, such as e.g. not more than 4 amino acids, more preferably not more than 3 amino acids, even more preferably not more than 2 amino acids and most preferably, one amino acid is lacking at the N-terminal end. In other words, in those cases where 6 amino acids are lacking, the N-terminal deletion fragment consists of the amino acid sequence LIPAPPLSKVPLQQN FQDNQF (SEQ ID NO:56); where 5 amino acids are lacking, the N-terminal deletion fragment consists of the amino acid sequence DLIPAPPLSKVPLQQN FQDNQF (SEQ ID NO:57); where 4 amino acids are lacking, the N-terminal deletion fragment consists of the amino acid sequence SDLIPAPPLSKV-PLQQNFQDNQF (SEQ ID NO:58); where 3 amino acids are lacking, the N-terminal deletion fragment consists of the amino acid sequence TSDLIPAPPLSKVPLQQNFQDNQF (SEQ ID NO:59); where 2 amino acids are lacking, the N-terminal deletion fragment consists of the amino acid sequence STSDLIPAPPLSKVPLQQNFQDNQF (SEQ ID NO:60); and where 1 amino acid is lacking, the N-terminal deletion fragment consists of the amino acid sequence DSTSDLIPAPPLSKVPLQQNFQDNQF (SEQ ID NO:61).

The same considerations apply to the C-terminal deletion fragment of the amino acid sequence LKENFIRFSKSLGL-PENHIVFPVPIDQCIDG (SEQ ID NO:16) of Frame 5, namely the term "C-terminal deletion fragment" refers to a fragment of the amino acid sequence of SEQ ID NO:16, in which one or several amino acids are lacking at the C-terminal end. Preferably, not more than 3 amino acids are lacking at the C-terminal end, more preferably not more than 2 amino acids and most preferably, one amino acid is lacking at the C-terminal end. In other words, in those cases where 3 amino acids are lacking, the C-terminal deletion fragment consists of the amino acid sequence LKENFIRFSK-SLGLPEN HIVFPVPIDQC (SEQ ID NO:62); where 2 amino acids are lacking, the C-terminal deletion fragment consists of the amino acid sequence LKENFIRFSKSLGL-PENHIVFPVPIDQCI (SEQ ID NO:63); and where 1 amino acid is lacking, the C-terminal deletion fragment consists of the amino acid sequence LKENFIRFSKSLGLPENHIVF-PVPIDQCID (SEQ ID NO:64).

In accordance with the present invention, the amino acid sequences of $x_1$ to $x_{15}$ can either consist of the specifically recited amino acid sequences or can be a variant of said specific amino acid sequences.

The term "variant" in accordance with the present invention refers to an amino acid sequence that differs from the specifically recited amino acid sequence by the substitution of one or several amino acids. The term "substitution", in accordance with the present invention, refers to the replacement of a particular amino acid with another amino acid. Thus, the total number of amino acids remains the same. In those cases where more than one amino acid is to be substituted, each amino acid is independently replaced with another amino acid, i.e. for each amino acid that is removed a different amino acid is introduced at the same position. The deletion of one or more amino acids at (a) certain position(s) and the introduction of one or more amino acids at (a) different position(s) is explicitly not encompassed by the term "substitution".

Substitutions, in accordance with the present invention, can be conservative amino acid substitutions or non-conservative amino acid substitutions.

The term "conservative amino acid substitution" is well known in the art and refers to the replacement of an amino acid with a different amino acid having similar structural and/or chemical properties. Such similarities include e.g. a similarity in polarity, charge, solubility, hydrophobicity, hydrophilicity, and/or the amphipathic nature of the residues involved. For example, nonpolar (hydrophobic) amino acids include alanine, valine, leucine, isoleucine, proline, phenylalanine, tyrosine, tryptophan, and methionine; polar neutral amino acids include glycine, serine, threonine, cysteine, asparagine, and glutamine; positively charged (basic) amino acids include arginine, lysine, and histidine; and negatively charged (acidic) amino acids include aspartic acid and glutamic acid.

Non-conservative amino acid substitutions can be introduced in order to introduce new reactive groups, for example, for the conjugation to other compounds, such as polyethylene glycol (PEG), hydroxyethyl starch (HES), biotin, peptides or proteins, or for the formation of non-naturally occurring intermolecular disulphide linkages. To this end, cysteine is introduced into the amino acid sequence, preferably at a position that corresponds to the position 14, 21, 60, 84, 87, 88, 114, 116, 117, 141, 143, 145, 146 or 158 of the wild-type (wt) Lcn2 sequence (SEQ ID NO:7). These positions also correspond to positions 14, 21, 60, 84, 141, 143, 145, 146 or 158 of the amino acid sequences of SEQ ID NOs: 1 to 6. The thiol moiety thus generated can then be used for the conjugation to other compounds, for example, in order to increase the serum half-life of the respective PSMA-specific binding protein. Accordingly, it is preferred in accordance with the present invention that in those cases where the substitution is a non-conservative amino acid substitution, it is a substitution that introduces a cysteine at the above described positions.

Most preferably, in accordance with the present invention, the substitutions are conservative amino acid substitutions.

In certain cases, i.e. in those parts of formula I defined by $x_5$ to $x_7$ and $x_{13}$, only one amino acid is indicated instead of an amino acid sequence comprising a plurality of amino acids. It will be appreciated that in these cases the variant is one other amino acid that substitutes for the one amino acid specifically recited in either of $x_5$ to $x_7$ or $x_{13}$.

In the cases of $x_1$ and $x_{15}$, the amino acid sequence can be a deletion fragment of the specifically recited sequence, as detailed above. In accordance with the present invention, the variant of the amino acid sequence defined by $x_1$ and/or $x_{15}$ can, therefore, also be a variant (comprising one or several amino acid substitutions) of such a deletion fragment.

In those cases where the PSMA-specific binding protein of the present invention comprises one or several variants, it is preferred that the total amount of all variations present in Frames 1 to 5 taken together is at most 12 amino acid substitutions. Even more preferred is that the total amount of N-terminal and/or C-terminal deletions together with the total amount of all variations present in Frames 1 to 5 is at most 17 amino acid deletions/substitutions, such as e.g. at most 12 amino acid deletions/substitutions, more preferably at most 7 amino acids deletions/substitutions, such as at most 5 amino acids deletions/substitutions, even more preferably at most 3 amino acids deletions/substitutions, such as at most 2 amino acids deletions/substitutions and most preferably there is only 1 amino acid deletion/substitution present in the PSMA-specific binding protein according to formula I.

It will be appreciated that also those PSMA-specific binding proteins that contain any terminal deletions and/or amino acid substitutions have to bind to PSMA with a $K_D$ of 10 nM or lower in order to be PSMA-specific binding proteins of the present invention.

Because the parts of formula I defined herein with an "x" are amino acids or amino acid sequences that form part of the frame or scaffold of the PSMA-specific binding proteins of the present invention, their substitution, in particular in form of conservative amino acid substitutions, will in many cases not affect the binding capability of the PSMA-specific binding protein. This is because these amino acids typically are not directly involved in the binding to PSMA, and their substitution for suitable alternative amino acids can be designed such that no alteration in the three-dimensional structure and folding of the protein occurs. On the other hand, such substitutions can provide numerous beneficial effects such as for improved expression in certain hosts or for stabilization of the protein by introduction of e.g. additional disulphide bridges.

In addition, the PSMA-specific binding protein of the present invention comprises four loop regions at the positions shown in formula I, which represent the hypervariable, specificity-determining segments that mediate the binding to PSMA.

In accordance with the present invention, the loop regions either consist of the amino acid sequences specifically recited in the claims, i.e. the amino acid sequences shown in formulas VII, VIII, IX and X, or they consist of amino acid sequences having at least 90% sequence identity to these specifically recited sequences.

In accordance with the present invention, the term "% sequence identity" describes the number of matches ("hits") of identical amino acids of two or more aligned amino acid sequences as compared to the number of amino acid residues making up the overall length of the amino acid sequences (or the overall compared part thereof). Percent identity is determined by dividing the number of identical residues by the total number of residues and multiplying the product by 100. In other terms, using an alignment, the percentage of amino acid residues that are the same (e.g., 90% identity) may be determined for two or more sequences or sub-sequences when these (sub)sequences are compared and aligned for maximum correspondence over a window of comparison, or over a designated region as measured using a sequence comparison algorithm as known in the art, or when manually aligned and visually inspected.

Those having skill in the art know how to determine percent sequence identity between/among sequences using, for example, algorithms such as those based on the NCBI BLAST algorithm (Altschul, S. F. et al. [1997] Nucleic Acids Res. 25:3389-3402), CLUSTALW computer program (Tompson, J. D. et al. [1994] Nucleic Acids Res. 22:4673-4680) or FASTA (Pearson, W. R. & Lipman, D. J. [1988] Proc. Natl. Acad. Sci. U.S.A. 85:2444-2448). The NCBI BLAST algorithm is preferably employed in accordance with this invention. For amino acid sequences, the BLASTP program uses as default a word length (W) of 3, and an expectation (E) of 10. The BLOSUM62 scoring matrix (Henikoff, S. & Henikoff, J. G. [1992] Proc. Natl. Acad. Sci. U.S.A. 89:10915-10919) uses alignments (B) of 50, expectation (E) of 10, M=5, N=4, and a comparison of both strands. Accordingly, all the (poly)peptides having a sequence identity of at least 90% as determined with the NCBI BLAST program fall under the scope of the invention.

In accordance with the present invention, the recited degree of identity refers to the sum of all amino acids of the four loop regions together. In other words, because Loop 1 consists of 14 amino acids, Loop 2 of 7 amino acids, Loop 3 of 11 amino acids and Loop 4 of 8 amino acids, the sum of all amino acids in the loop regions is 40 amino acids, as shown in formulas VII, VIII, IX and X. In those cases where the loop regions differ from the specifically recited amino acid sequences, the degree of difference is limited to the recited degree. Thus, a sequence identity of at least 90% requires that out of the 40 amino acids that make up the loop regions, at least 36 have to be as defined in formulas VII, VIII, IX and X taken together. Because the four loop regions do not form one consecutive stretch of amino acid sequence, it will be appreciated that a comparison (sequence alignment) is most conveniently carried out for the sequences of Loop 1 to Loop 4 individually and the overall degree of sequence identity is subsequently determined by summing up the results of all four loops. For example, if a sequence comparison with Loop 1 shows one amino acid difference, a comparison for Loop 2 shows no difference, a comparison for Loop 3 shows one amino acid difference and a comparison for Loop 4 shows two amino acids difference, then the overall degree of identity is 90%.

In accordance with this embodiment of the present invention, sequences having at least 92.5% sequence identity, more preferably at least 95%, and most preferably at least 97.5% are also encompassed.

It is preferred in accordance with the present invention that any variation in the specifically recited sequences of the loop regions is restricted to those residues denoted as "y"-residues.

Because the loop regions are involved in binding to the target, i.e. PSMA, their amino acid sequence determines the binding capability of the resulting PSMA-specific binding protein. Suitable methods to test whether a PSMA-specific binding protein comprising or consisting of loop regions that have at least 90% sequence identity to the specifically recited amino acid sequences still binds to PSMA with a $K_D$ of 10 nM or lower have been discussed herein above. The PSMA-specific binding protein of formula I may thus be summarized as comprising or consisting of a sequence as shown in formula Z1 below:

(formula Z1)
$x_1$-(H/Q)-$x_2$-Loop1-S-$x_3$-(K/N)-$x_4$-N-$x_5$-Loop2-Y-$x_6$-T-$x_7$-A-$x_8$-(S/C)-(Q/R)-$x_9$-(F/Y)-$x_{10}$-Loop3-G-$x_{11}$(N/S)-$x_{12}$-Loop4-$x_{13}$-I-$x_{14}$-(E/K)-$x_{15}$.

In a more preferred embodiment of the PSMA-specific binding protein of the invention, Loop 1 consists of the amino acid sequence GNVILREDKDPYKM (SEQ ID NO:19) or GNMILREDKDPYKM (SEQ ID NO:20); Loop 2 consists of the amino acid sequence RFYLNKC (SEQ ID NO:21), RFYLKKC (SEQ ID NO:22), RYYLNKC (SEQ ID NO:23) or RYYLKKC (SEQ ID NO:24); Loop 3 consists of the amino acid sequence GTIKSGPGKTS (SEQ ID NO:25) or GTIKSGPGDTS (SEQ ID NO:26); and/or Loop 4 consists of the amino acid sequence EVQQNREW (SEQ ID NO:27).

In an even more preferred embodiment of the PSMA-specific binding protein of the invention, Loop 1 consists of the amino acid sequence GNVILREDKDPYKM (SEQ ID NO:19) or GNMILREDKDPYKM (SEQ ID NO:20); Loop 2 consists of the amino acid sequence RFYLNKC (SEQ ID NO:21), RFYLKKC (SEQ ID NO:22), RYYLNKC (SEQ ID NO:23) or RYYLKKC (SEQ ID NO:24); Loop 3 consists of the amino acid sequence GTIKSGPGKTS (SEQ ID NO:25) or GTIKSGPGDTS (SEQ ID NO:26); and Loop 4 consists of the amino acid sequence EVQQNREW (SEQ ID NO:27).

Thus, in this preferred embodiment, the amino acid sequence of formula I can be represented more specifically as the following formula Z2:

(formula Z2)
$x_1$-(H/Q)-$x_2$-$y_1$-(M/V)-$y_2$-Y-$y_3$-S-$x_3$-(K/N)-$x_4$-N-$x_5$-R-(F/Y)-Y-L-(K/N)-$y_4$-Y-$x_6$-T-$x_7$-A-$x_8$-(S/C)-(Q/R)-$x_9$-

(F/Y)-$x_{10}$-$y_5$-T-$y_6$-G-$y_7$(K/D)-$y_8$-G-$x_{11}$-(N/S)-$x_{12}$-E-$y_9$-Q-$y_{10}$-W-$x_{13}$-I-$x_{14}$-(E/K)-$x_{15}$ wherein the residues $x_1$ to $x_{15}$ and $y_1$ to $y_{10}$ are as defined further above.

The amino acid sequences of the loop regions of these preferred embodiments, and accordingly of formula Z2, correspond to the amino acid sequences of the loop regions of the specific variants described in the examples below, i.e. Loop 1 of variants A3A5, A3A5.1, A3A5.7, A3A5.8 and A3A5.9 is represented in the amino acid sequence of SEQ ID NO:19, and Loop 1 of variant A3 is represented in the amino acid sequence of SEQ ID NO:20; Loop 2 of variant A3A5.7 is represented in the amino acid sequence of SEQ ID NO:21, Loop 2 of variants A3 and A3A5 is represented in the amino acid sequence of SEQ ID NO:22, Loop 2 of variants A3A5.8 and A3A5.9 is represented in the amino acid sequence of SEQ ID NO:23, and Loop 2 of variant A3A5.1 is represented in the amino acid sequence of SEQ ID NO:24; Loop 3 of variants A3, A3A5 and A3A5.7 is represented in the amino acid sequence of SEQ ID NO:25, and Loop 3 of variants A3A5.1, A3A5.8 and A3A5.9 is represented in the amino acid sequence of SEQ ID NO:26; and Loop 4 of all six said variants is represented in the amino acid sequence of SEQ ID NO:27.

Accordingly, these preferred PSMA-specific binding proteins having an amino acid sequence of formula Z2 comprise or consist of an amino acid sequence that encompasses variable frame regions, as defined above, in combination with the recited loop regions. As is shown in the appended examples below, PSMA-specific binding proteins having in their loop regions these preferred amino acid sequences possess remarkable target specificity, with dissociation constants in the nanomolar and even picomolar range. Moreover, the data provided herein further confirm the ability of these PSMA-specific binding proteins to detect PSMA on live cells, thereby rendering them particularly well suited binders for diagnostic and therapeutic applications.

In an even more preferred embodiment of the PSMA-specific binding protein of the invention, Loop 1 consists of the amino acid sequence GNVILREDKDPYKM (SEQ ID NO:19); Loop 2 consists of the amino acid sequence RFYLNKC (SEQ ID NO:21); Loop 3 consists of the amino acid sequence GTIKSGPGKTS (SEQ ID NO:25); and Loop 4 consists of the amino acid sequence EVQQNREW (SEQ ID NO:27).

In accordance with this particularly preferred embodiment, the PSMA-specific binding protein of the present invention comprises in the loop regions the amino acid sequences of variant A3A5.7, which has been found in the appended examples to be the best specific binding protein for PSMA amongst the variants tested.

In another more preferred embodiment of the PSMA-specific binding protein of the invention, the total amount of variation—in those cases where one or more of $x_1$ to $x_{15}$ is/are a variant(s) of the specifically recited amino acid sequence(s)—is 12 or less amino acids.

The following formula Z3 shows the amino acid sequence of formula I, wherein the amino acid sequences of Frames 1 to 5 have been incorporated, including the specific residues $x_1$ to $x_{15}$, which are highlighted as bold and underlined residues.

(formula Z3)
QDSTSDLIPAPPLSKVPLQQNFQDNQF-(H/Q)-GKWYVVGLA-Loop1-

S-ATIYEL-(K/N)-EDKSYNVT-N-V-Loop2-Y-Y-T-I-A-TFVPG- (S/C)-(Q/R)-PGE-(F/Y)-TL-Loop3-G-LVRVVSTNY-(N/S)-

QHAMVFFK-Loop4-F-I-ITLYGRTKELTS-(E/K)-

LKENFIRFSKSLGLPENHIVFPVPIDQCIDG.

In accordance with this preferred embodiment, the overall sum of all variations of $x_1$ to $x_{15}$, as compared to the specifically cited sequences presented for $x_1$ to $x_{15}$ above, does not exceed 12 amino acid variations. Based on the above shown formula Z3 this means that the sum of all variations in the bold and underlined residues over the entire length of formula Z3 does not exceed 12 amino acids variations (as compared to the sequences shown in bold and underlined in formula Z3). When additionally considering possible N-terminal and/or C-terminal deletions together with these variations in the frame regions, it is preferred that the total number of amino acid deletions/substitutions is at most 17, as defined herein above.

As a non-limiting example, in such a variant PSMA-specific binding protein of the present invention, the first five amino acids at the N-terminus can be deleted (i.e. in $x_1$) and another five to 12 amino acid substitutions can be present in the remaining amino acid sequences of $x_1$ to $x_{15}$, for example in $x_2$ and $x_7$. As an alternative example, in such a variant PSMA-specific binding protein of the present invention, the first five amino acids at the N-terminus (i.e. in $x_1$) and the last five amino acids at the C-terminus can be deleted (i.e. in $x_{15}$), either with no substitutions in the frame regions or with up to seven amino acid substitutions in the remaining amino acid sequences of $x_1$ to $x_{15}$.

More preferably, the overall sum of all variations is 10 or less, such as e.g. 5 or less, 4 or less, 3 or less, more preferably 2 or less and most preferably, there is only one variation in the bold and underlined residues over the entire length of formula Z3.

Most preferably, the PSMA-specific binding protein of the invention is a protein based on any one of the sequences of SEQ ID NOs: 1 to 6, wherein up to 12 amino acid variations in $x_1$ to $x_{15}$ (corresponding to positions 1 to 28, 29 to 37, 53 to 58, 60 to 67, 69, 78, 80, 82 to 86, 89 to 91, 93, 94, 107 to 115, 117 to 124, 133, 135 to 146 and 148 to 178 in any one of SEQ ID NOs: 1 to 6) have been introduced. The amino acid variations that can be introduced, and preferred numbers of variations, are as defined herein above with regard to the formula I.

In another more preferred embodiment of the PSMA-specific binding protein of the invention, Frame 1 consists of the amino acid sequence QDSTSDLIPAPPLSKVPLQQN-FQDNQFHGKWYVVGLA (SEQ ID NO:28) or QDSTS-DLIPAPPLSKVPLQQNFQDNQFQGKWYVVGLA (SEQ ID NO:29); Frame 2 consists of the amino acid sequence SATIYELKEDKSYNVTNV (SEQ ID NO:30) or SATI-YELNEDKSYNVTNV (SEQ ID NO:31); Frame 3 consists of the amino acid sequence YYTIATFVPGSRPGEFTL (SEQ ID NO:32), YYTIATFVPGSQPGEFTL (SEQ ID NO:33), YYTIATFVPGSQPGEYTL (SEQ ID NO:34), YYTIATFVPGSRPGEYTL (SEQ ID NO:35), YYTIAT-FVPGCRPGEFTL (SEQ ID NO:36), YYTIATFVPGC-QPGEFTL (SEQ ID NO:37), YYTIATFVPGCQPGEYTL (SEQ ID NO:38), or YYTIATFVPGCRPGEYTL (SEQ ID NO:39); Frame 4 consists of the amino acid sequence GLVRVVSTNYSQHAMVFFK (SEQ ID NO:40) or GLVRVVSTNYNQHAMVFFK (SEQ ID NO:41); and/or Frame 5 consists of the amino acid sequence FIITLYGRT-KELTSKLKENFIRFSKSLGLPENHIV FPVPIDQCIDG (SEQ ID NO:42) or FIITLYGRTKELTSELKENFIRFSK-SLGLPENHIVFPVPIDQCIDG (SEQ ID NO:43).

In an even more preferred embodiment of the PSMA-specific binding protein of the invention, Frame 1 consists of the amino acid sequence QDSTSDLIPAPPLSKVPLQQN-FQDNQFHGKWYVVGLA (SEQ ID NO:28) or QDSTS-DLIPAPPLSKVPLQQNFQDNQFQ GKWYVVGLA (SEQ ID NO:29); Frame 2 consists of the amino acid sequence SATIYELKEDKSYNVTNV (SEQ ID NO:30) or SATI-YELNEDKSYNVTNV (SEQ ID NO:31); Frame 3 consists of the amino acid sequence YYTIATFVPGSRPGEFTL (SEQ ID NO:32), YYTIATFVPGSQPGEFTL (SEQ ID NO:33), YYTIATFVPGSQPGEYTL (SEQ ID NO:34), YYTIATFVPGSRPGEYTL (SEQ ID NO:35), YYTIAT-FVPGCRPGEFTL (SEQ ID NO:36), YYTIATFVPGC-QPGEFTL (SEQ ID NO:37), YYTIATFVPGCQPGEYTL (SEQ ID NO:38), or YYTIATFVPGCRPGEYTL (SEQ ID NO:39); Frame 4 consists of the amino acid sequence GLVRVVSTNYSQHAMVFFK (SEQ ID NO:40) or GLVRVVSTNYNQHAMVFFK (SEQ ID NO:41); and Frame 5 consists of the amino acid sequence FIITLYGRT-KELTSKLKENFIRFSKSLGLPENHIVFPVPIDQCIDG (SEQ ID NO:42) or FIITLYGRTKELT SELKENFIRFSK-SLGLPENHIVFPVPIDQCIDG (SEQ ID NO:43).

The amino acid sequences of the frame regions of these preferred embodiments correspond to the amino acid sequences of the frame regions of the specific variants described in the examples below, or of combinations of said amino acid variations, i.e. Frame 1 of all six variants is represented in the amino acid sequence of SEQ ID NO:28, while the amino acid sequence of SEQ ID NO:29 represents a variant having at position 28 of the wild-type (wt) Lcn2 sequence (SEQ ID NO:7) the originally present Q instead of a H; Frame 2 of variant A3A5.1 is represented in the amino acid sequence of SEQ ID NO:31, and Frame 2 of variants A3, A3A5, A3A5.7, A3A5.8 and A3A5.9 is represented in the amino acid sequence of SEQ ID NO:30; Frame 3 of variant A3A5.7 is represented in the amino acid sequence of SEQ ID NO:32, Frame 3 of variants A3, A3A5, A3A5.8 and A3A5.9 is represented in the amino acid sequence of SEQ ID NO:33, and Frame 3 of variant A3A5.1 is represented in the amino acid sequence of SEQ ID NO:34; while the amino acid sequences of SEQ ID NOs:35 to 39 represent variations thereof as well as variants having at position 87 of the wt Lcn2 sequence (SEQ ID NO:7) the C that is originally present in the wt scaffold instead of an S; Frame 4 of variant A3A5.7 is represented in the amino acid sequence of SEQ ID NO:40 and Frame 4 of variants A3, A3A5, A3A5.1, A3A5.8 and A3A5.9 is represented in the amino acid sequence of SEQ ID NO:41; and Frame 5 of variants A3A5.1, A3A5.7 and A3A5.9 is represented in the amino acid sequence of SEQ ID NO:42 and Frame 5 of variants A3, A3A5 and A3A5.8 is represented in the amino acid sequence of SEQ ID NO:43.

For the amino acid positions 28 and 87, variants comprising the wt Lcn2 sequence (SEQ ID NO:7) as well as variants comprising amino acid substitutions at said position (i.e. Q→H at position 28 and C→S at position 87 of SEQ ID NO:7) were included herein. The rationale for this approach is that said amino acid substitutions were solely introduced for ease of genetic manipulation of the PSMA-specific binding proteins of the present invention. Thus, both the amino acids present in the wildtype as well as in the variants can be employed in accordance with the present invention.

In a yet even more preferred embodiment of the PSMA-specific binding protein of the invention, Frame 1 consists of the amino acid sequence QDSTSDLIPAPPLSKVPLQQN-FQDNQFHGKWYVVGLA (SEQ ID NO:28); Frame 2 consists of the amino acid sequence SATIYELKEDKSYN-VTNV (SEQ ID NO:30); Frame 3 consists of the amino acid sequence YYTIATFVPGSRPGEFTL (SEQ ID NO:32); Frame 4 consists of the amino acid sequence GLVRVVST-NYSQHAMVFFK (SEQ ID NO:40); and Frame 5 consists of the amino acid sequence FIITLYGRTKELTSKLKEN-FIRFSKSLGLPENHIVFPVPIDQCIDG (SEQ ID NO:42).

In accordance with this particularly preferred embodiment, the PSMA-specific binding protein of the present invention comprises in the frame regions the amino acid sequences of variant A3A5.7, which has been found in the appended examples to be the best specific binding protein for PSMA amongst the variants tested.

In another preferred embodiment of the PSMA-specific binding protein of the invention, the PSMA-specific binding protein comprises or consists of an amino acid sequence selected from the group consisting of the amino acid sequences of SEQ ID NOs:1 to 6.

These amino acid sequences represent the six variants described in the appended examples, i.e. SEQ ID NO:1 represents variant A3, SEQ ID NO:2 represents variant A3A5, SEQ ID NO:3 represents variant A3A5.1, SEQ ID NO:4 represents variant A3A5.7, SEQ ID NO:5 represents variant A3A5.8 and SEQ ID NO:6 represents variant A3A5.9.

It is particularly preferred in accordance with the present invention that the PSMA-specific binding protein comprises or consists of an amino acid sequence selected from the group consisting of the amino acid sequences represented in SEQ ID NO:3 and SEQ ID NO:4. Even more preferably, the PSMA-specific binding protein comprises or consists of the amino acid sequence represented in SEQ ID NO:4.

The present invention further relates to a nucleic acid molecule encoding the PSMA-specific binding protein according to the invention.

In accordance with the present invention, the term "nucleic acid molecule", also referred to as nucleic acid sequence or polynucleotide herein, includes DNA, such as cDNA or genomic DNA, and RNA. It is understood that the term "RNA" as used herein comprises all forms of RNA including mRNA. Both, single-strand as well as double-strand nucleic acid molecules are encompassed by this term. Further included are nucleic acid mimicking molecules known in the art such as synthetic or semi-synthetic derivatives of DNA or RNA and mixed polymers. Such nucleic acid mimicking molecules or nucleic acid derivatives according to the invention include phosphorothioate nucleic acid, phosphoramidate nucleic acid, 2'-O-methoxyethyl ribonucleic acid, morpholino nucleic acid, hexitol nucleic acid (HNA), peptide nucleic acid (PNA) and locked nucleic acid (LNA) (see Braasch, D. A. & Corey, D. R. [2001] Chem. Biol. 8:1-7). PNA a synthetic DNA-mimic with an amide backbone in place of the sugar-phosphate backbone of DNA or RNA. As a consequence, certain components of DNA, such as phosphorus, phosphorus oxides, or deoxyribose derivatives, are not present in PNAs. LNA is an RNA derivative in which the ribose ring is constrained by a methylene linkage between the 2'-oxygen and the 4'-carbon. They may contain additional non-natural or derivatised nucleotide bases, as will be readily appreciated by those skilled in the art.

The nucleic acid molecules of the invention can e.g. be synthesized by standard chemical synthesis methods or isolated from natural sources or produced semi-synthetically, i.e. by combining chemical synthesis and isolation from natural sources. Ligation of the coding sequences to transcriptional regulatory elements and/or to other amino acid encoding sequences can be carried out using established methods, such as restriction digests, ligations and molecular cloning.

Representative nucleic acid molecules encoding the six PSMA-specific binding proteins described in the appended examples are provided herein as SEQ ID NOs:44 to 49, wherein i.e. SEQ ID NO:44 encodes variant A3, SEQ ID NO:45 encodes variant A3A5, SEQ ID NO:46 encodes variant A3A5.1, SEQ ID NO:47 encodes variant A3A5.7, SEQ ID NO:48 encodes variant A3A5.8 and SEQ ID NO:49 encodes variant A3A5.9. These nucleic acid sequences represent the coding regions corresponding to the amino acid sequences shown in SEQ ID NOs: 1 to 6, respectively, i.e. the nucleic acid sequences as shown are devoid of the N-terminal bacterial signal peptides and the C-terminal Strep-tag II used for production and purification of the PSMA-specific binding proteins of the present invention as shown in the appended examples.

Further, the present invention also relates to a vector comprising the nucleic acid molecule of the invention.

Usually, the vector is a plasmid, cosmid, virus, bacteriophage or another vector used conventionally e.g. in genetic engineering. Preferably, the vector is a plasmid, more preferably a plasmid based on the generic E. coli expression vector pASK75, such as e.g. the vector pNGAL98 employed in the appended examples. Such vectors that were specifically developed for Anticalin expression but also Anticalin production by e.g. periplasmic secretion in E. coli have been described in the art, such as e.g. in (Gebauer, M. & Skerra, A. [2012] Meth. Enzymol. 503:157-188).

Alternative vectors including, without being limiting, plasmid vectors, such as pQE-12, the pUC-series, pBluescript (Stratagene), the pET-series of expression vectors (Novagen) or pCRTOPO (Invitrogen), lambda gt11, pJOE, the pBBR1-MCS series, pJB861, pBSMuL, pBC2, pUCPKS, pTACT1 and vectors compatible with expression in mammalian cells like E-027 pCAG Kosak-Cherry (L45a) vector system, pREP (Invitrogen), pCEP4 (Invitrogen), pMC1neo (Stratagene), pXT1 (Stratagene), pSG5 (Stratagene), EBO-pSV2neo, pBPV-1, pdBPVMMTneo, pRS-Vgpt, pRSVneo, pSV2-dhfr, pIZD35, Okayama-Berg cDNA expression vector pcDV1 (Pharmacia), pRc/CMV, pcDNA1, pcDNA3 (Invitrogen), pcDNA3.1, pSPORT1 (GIBCO BRL), pGEMHE (Promega), pLXIN, pSIR (Clontech), pIRES-EGFP (Clontech), pEAK-10 (Edge Biosystems) pTriEx-Hygro (Novagen) and pCINeo (Promega). Non-limiting examples for plasmid vectors suitable for *Pichia pastoris* comprise e.g. the plasmids pAO815, pPIC9K and pPIC3.5K (all Invitrogen). Another vector suitable for expressing proteins in *Xenopus* embryos, zebrafish embryos as well as a wide variety of mammalian and avian cells is the multipurpose expression vector pCS2+.

Generally, vectors can contain one or more origins of replication (ori) and inheritance systems for cloning or expression, one or more markers for selection in the host, e.g., antibiotic resistance, and one or more expression cassettes. In addition, the coding sequences comprised in the vector can be ligated to transcriptional regulatory elements and/or to other amino acid encoding sequences using established methods. Such regulatory sequences are well known to those skilled in the art and include, without being limiting, regulatory sequences ensuring the initiation of transcription, internal ribosomal entry sites (IRES) (Owens, G. C. et al.

Proc. Natl. Acad. Sci. U.S.A. 98:1471-1476) and optionally regulatory elements ensuring termination of transcription and stabilization of the transcript. Non-limiting examples for such regulatory elements ensuring the initiation of transcription comprise promoters, a translation initiation codon, enhancers, insulators and/or regulatory elements ensuring transcription termination, which are to be included downstream of the nucleic acid molecules of the invention. Further examples include Kozak sequences and intervening sequences flanked by donor and acceptor sites for RNA splicing, nucleotide sequences encoding secretion signals or, depending on the expression system used, signal sequences capable of directing the expressed protein to a cellular compartment or to the culture medium. The vectors may also contain an additional expressible polynucleotide coding for one or more chaperones to facilitate correct protein folding. Suitable bacterial expression hosts comprise e. g. strains derived from JM83, W3110, KS272, TG1, BL21 (such as BL21(DE3), BL21(DE3)PlysS, BL21(DE3)RIL, BL21 (DE3)PRARE) or Rosettaâ. For vector modification, PCR amplification and ligation techniques, see Sambrook & Russel [2001] (Cold Spring Harbor Laboratory, NY).

Regulatory elements that have been optimized for the expression of Anticalins have been described in the art, such as e.g. in (Gebauer, M. & Skerra, A. [2012] Meth. Enzymol. 503:157-188) and include the tetracycline promoter/operator ($tet^{p/o}$), which is chemically inducible with anhydrotetracycline, an N-terminal OmpA signal for periplasmic secretion in E. coli, an affinity tag, such as e.g. Strep-tag II or the A3C5 tag, the rho-independent Ipp terminator as well as an ampicillin-resistance gene (β-lactamase), a truncated ColEI origin of replication, and the intergenic region of the filamentous phage f1 for the biosynthesis of phagemid particles upon co-infection of E. coli with a helper phage.

Additional examples of suitable origins of replication include, for example, the full length ColE1, the SV40 viral and the M13 origins of replication, while additional examples of suitable promoters include, without being limiting, the cytomegalovirus (CMV) promoter, SV40-promoter, RSV-promoter (Rous sarcoma virus), the lacZ promoter, chicken β-actin promoter, CAG-promoter (a combination of chicken β-actin promoter and cytomegalovirus immediate-early enhancer), the gai10 promoter, human elongation factor 1α-promoter, AOX1 promoter, GAL1 promoter CaM-kinase promoter, the lac, trp or tac promoter, the T7 or T5 promoter, the lacUV5 promoter, the *Autographa californica* multiple nuclear polyhedrosis virus (AcMNPV) polyhedral promoter or a globin intron in mammalian and other animal cells. One example of an enhancer is e.g. the SV40-enhancer. Non-limiting additional examples for regulatory elements ensuring transcription termination include the SV40-poly-A site, the tk-poly-A site or the AcMNPV polyhedral polyadenylation signals. Further non-limiting examples of selectable markers include dhfr, gpt, neomycin, hygromycin, blasticidin or geneticin Preferably, the vector of the present invention is an expression vector. An expression vector according to this invention is capable of directing the replication and the expression of the nucleic acid molecule of the invention and, accordingly, of the PSMA-specific binding proteins of the present invention encoded thereby.

The nucleic acid molecules and/or vectors of the invention as described herein above may be designed for introduction into cells by e.g. non chemical methods (electroporation, sonoporation, optical transfection, gene electrotransfer, hydrodynamic delivery or naturally occurring transformation upon contacting cells with the nucleic acid molecule of the invention), chemical based methods (calcium phosphate, liposomes, DEAE-dextrane, polyethylenimine, nucleofection), particle-based methods (gene gun, magnetofection, impalefection) phage vector-based methods and viral methods. For example, expression vectors derived from viruses such as retroviruses, vaccinia virus, adeno-associated virus, herpes viruses, Semliki Forest Virus or bovine papilloma virus, may be used for delivery of the nucleic acid molecules into targeted cell population. Additionally, baculoviral systems can also be used as vector in eukaryotic expression system for the nucleic acid molecules of the invention.

Preferably, the nucleic acid molecules and/or vectors of the invention are designed for transformation of electrocompetent E. coli by electroporation or for stable transfection of CHO cells by calcium phosphate-, polyethylenimine- or lipofectamine-transfection (Pham, P. L. et al. Mol. Biotechnol. 34:225-237; Geisse, S. & Voedisch, B. [2012] Methods Mol. Biol. 899:203-219; Hacker, D. L. et al. [2013] Protein Expr. Purif. 92:67-76).

The present invention further relates to a host cell or a non-human host transformed with the vector of the invention.

It will be appreciated that the term "host cell or a non-human host transformed with the vector of the invention", in accordance with the present invention, relates to a host cell or a non-human host that comprises the vector of invention.

Suitable prokaryotic hosts comprise e.g. bacteria of the species *Escherichia, Corynebacterium (glutamicum), Pseudomonas (fluorescens), Lactobacillus, Streptomyces, Salmonella* or *Bacillus.*

Typical mammalian host cells include, Hela, HEK293, H9, Per.C6 and Jurkat cells, mouse NIH3T3, NS0 and C127 cells, COS 1, COS 7 and CV1, quail QC1-3 cells, mouse L cells, mouse sarcoma cells, Bowes melanoma cells and Chinese hamster ovary (CHO) cells. Most preferred mammalian host cells in accordance with the present invention are CHO cells.

Also within the scope of the present invention are primary mammalian cells or cell lines. Primary cells are cells which are directly obtained from an organism. Suitable primary cells are, for example, mouse embryonic fibroblasts (MEF), mouse primary hepatocytes, cardiomyocytes and neuronal cells as well as mouse muscle stem cells (satellite cells), human dermal and pulmonary fibroblasts, human epithelial cells (nasal, tracheal, renal, placental, intestinal, bronchial epithelial cells), human secretory cells (from salivary, sebaceous and sweat glands), human endocrine cells (thyroid cells), human adipose cells, human smooth muscle cells, human skeletal muscle cells, human leucocytes such as B-cells, T-cells, NK-cells or dendritic cells and stable, immortalized cell lines derived thereof (for example hTERT or oncogene immortalized cells). Appropriate culture media and conditions for the above described host cells are known in the art.

Other suitable eukaryotic host cells are e.g. chicken cells, such as e.g. DT40 cells, or yeasts such as *Saccharomyces cerevisiae, Pichia pastoris, Schizosaccharomyces pombe* and *Kluyveromyces* lactic. Insect cells suitable for expression are e.g. *Drosophila* S2, *Drosophila* Kc, *Spodoptera* Sf9 and Sf21 or *Trichoplusia* Hi5 cells. Suitable zebrafish cell lines include, without being limiting, ZFL, SJD or ZF4.

Appropriate culture media and conditions for the above described host cells are known in the art.

Preferably, the host cell transformed with the vector of the invention is E. coli, most preferably E. coli selected from E.

*coli* supE strain TG1/F⁻, *E. coli* W3110, *E. coli* JM83, *E. coli* KS272, or *E. coli* BL21. These host cells as well as suitable media and cell culture conditions have been described in the art, e.g. in Gebauer, M. & Skerra, A. [2012] (Meth. Enzymol. 503:157-188).

The host cells in accordance with this embodiment may e.g. be employed to produce large amounts of the PSMA-specific binding proteins of the present invention.

The present invention also relates to a method for the production of a PSMA-specific binding protein of the invention, the method comprising culturing the host cell of the invention under suitable conditions and isolating the PSMA-specific binding protein produced.

In accordance with this embodiment, the vector present in the host of the invention is either an expression vector, or the vector mediates the stable integration of the nucleic acid molecule encoding the PSMA-specific binding protein of the present invention into the genome of the host cell in such a manner that expression of the protein is ensured. Means and methods for selection a host cell in which the nucleic acid molecule encoding the PSMA-specific binding protein of the present invention has been successfully introduced such that expression of the protein is ensured are well known in the art and have been described (Browne, S. M. & Al-Rubeai, M. [2007] Trends Biotechnol. 25:425-432; Matasci, M et al. [2008] Drug Discov. Today: Technol. 5:e37-e42; Wurm, F. M. [2004] Nat. Biotechnol. 22:1393-1398).

Suitable conditions for culturing prokaryotic or eukaryotic host cells are well known to the person skilled in the art. For example, bacteria such as e.g. *E. coli* can be cultured under aeration in Luria Bertani (LB) medium, typically at a temperature from 4 to about 37° C. To increase the yield and the solubility of the expression product, the medium can be buffered or supplemented with suitable additives known to enhance or facilitate both. In those cases where an inducible promoter controls the nucleic acid molecule of the invention in the vector present in the host cell, expression of the polypeptide can be induced by addition of an appropriate inducing agent, such as e.g. anhydrotetracycline as employed in the appended examples. Suitable expression protocols and strategies have been described in the art, e.g. in (Gebauer, M. & Skerra, A. [2012] Meth. Enzymol. 503:157-188) and can be adapted to the needs of the specific host cells and the requirements of the protein to be expressed, if required.

Depending on the cell type and its specific requirements, mammalian cell culture can e.g. be carried out in RPMI, Williams' E or DMEM medium containing 10% (v/v) FCS, 2 mM L-glutamine and 100 U/ml penicillin/streptomycin. The cells can be kept e.g. at 37° C. or at 41° C. for DT40 chicken cells, in a 5% $CO_2$, water-saturated atmosphere. A suitable medium for insect cell culture is e.g. TNM+10% FCS, SF900 or HyClone SFX-Insect medium. Insect cells are usually grown at 27° C. as adhesion or suspension cultures. Suitable expression protocols for eukaryotic or vertebrate cells are well known to the skilled person and can be retrieved e.g. from Sambrook, J & Russel, D. W. [2001] (Cold Spring Harbor Laboratory, NY).

Preferably, the method is carried out using either bacterial cells, such as e.g. *E. coli* cells, or mammalian cells, such as e.g. CHO cells. More preferably, the method is carried out using *E. coli* cells or CHO cells and most preferably, the method is carried out using *E. coli* cells.

Methods of isolation of the protein produced comprise, without limitation, purification steps such as affinity chromatography (preferably using a fusion-tag such as the Strep-tag II or the $His_6$ tag), gel filtration (size exclusion chromatography), anion exchange chromatography, cation exchange chromatography, hydrophobic interaction chromatography, high pressure liquid chromatography (HPLC), reversed phase HPLC or immunoprecipitation. These methods are well known in the art and have been generally described, e.g. in Sambrook, J & Russel, D. W. [2001] (Cold Spring Harbor Laboratory, NY), more specifically for Anticalins in e.g. Gebauer, M. & Skerra, A. [2012] (Meth. Enzymol. 503:157-188) and are also described in the appended examples, see e.g. Example 1.

In accordance with the present invention, the term "isolating the PSMA-specific binding protein produced" refers to the isolation of the PSMA-specific binding proteins of the present invention.

In addition, the present invention further relates to a protein conjugate comprising the PSMA-specific binding protein of the invention or the PSMA-specific binding protein produced by the method of the invention.

The term "protein conjugate", as used herein, relates to the PSMA-specific binding protein of the invention or the PSMA-specific binding protein produced by the method of the invention, to which one or more molecules are coupled (i.e. conjugated).

Conjugation may be carried out by recombinant DNA technology using well established techniques. As a result, the protein conjugate is created through the joining of two or more genes that originally coded for separate molecules. Translation of this fusion gene results in a protein conjugate, also called fusion protein, with functional properties derived from each of the original molecules. Suitable vectors are known in the art and have been described herein above. It will be appreciated that if the protein conjugate of the invention is produced by recombinant DNA technology, the linker is a peptide linker, as defined further below.

Alternatively, the two (or more) molecules to be conjugated may also be provided separately and linked by chemical methods, as e.g. described in (Hermanson, G. T. [2013] Bioconjugate Techniques, Academic Press, 3rd Ed), either by direct coupling of the molecules via functional or functionalized groups or by indirect coupling employing a linker. In this case, the second (and any further) molecule does not necessarily have to be a protein but may also be e.g. a nucleic acid molecule, a lipid, non-peptidic ligands, small molecule drugs, toxic compounds or diagnostically and therapeutically relevant radioactive moieties, including metal chelators, and fluorescent tracers.

The term "linker", as used in accordance with the present invention, relates to peptide linkers, i.e. a sequence of amino acids, as well as to non-peptide linkers.

A peptide linker as envisaged by the present invention is a (poly)peptide linker of at least 1 amino acid in length. Preferably, the linker is 1 to 100 amino acids in length. More preferably, the linker is 5 to 50 amino acids in length and even more preferably, the linker is 10 to 20 amino acids in length. Preferably, the linker is a flexible linker using e.g. the amino acids glycine and/or serine. Preferably the linker sequences are $(Gly_4Ser)_3$, or $(Gly_4Ser)_2$. The length and sequence of a suitable linker depends on the composition of the respective protein conjugate. Methods to test the suitability of different linkers are well known in the art and include e.g. the comparison of the binding affinity or the protein stability or the production yield of the protein conjugate comprising the PSMA-specific binding protein of the invention (or the PSMA-specific binding protein produced by the method of the invention) to protein conjugates comprising different linkers as well as to the respective PSMA-specific binding protein of the present invention without a conjugation partner. Peptide linkers are preferred in accordance with the present invention.

The term "non-peptide linker", as used in accordance with the present invention, refers to linkage groups having two or more reactive groups but excluding peptide linkers as defined above. For example, the non-peptide linker may be a polymer having reactive groups at both ends, which individually bind to reactive groups of the molecules of the protein conjugate, for example, an amino terminus, a lysine residue, a histidine residue or a cysteine residue.

Suitable reactive groups of polymers include an aldehyde group, a propionic aldehyde group, a butyl aldehyde group, a maleimide group, a ketone group, a vinyl sulfone group, a thiol group, a hydrazide group, a carbonylimidazole group, an imidazolyl group, a nitrophenyl carbonate (NPC) group, a trysylate group, an isocyanate group, and succinimide derivatives. Examples of succinimide derivatives include succinimidyl propionate (SPA), succinimidyl butanoic acid (SBA), succinimidyl carboxymethylate (SCM), succinimidyl succinamide (SSA), succinimidyl succinate (SS), succinimidyl carbonate, and N-hydroxy succinimide (NHS). The reactive groups at both ends of the non-peptide polymer may be the same or different. For example, the non-peptide polymer may have a maleimide group at one end and an aldehyde group at another end.

Such protein conjugates can be suitable to confer new characteristics on the PSMA-specific binding proteins of the present invention or the PSMA-specific binding protein produced by the method of the invention.

For example, and as discussed herein above, conjugation can be employed to modify or enhance the solubility of the resulting protein conjugate, to modify or enhance their stability, or to facility the purification of said molecules.

Solubility and stability can for example be affected by conjugation to larger molecules capable of modulating serum half-life, such as e.g. molecules selected from the group consisting of polyethylene glycol (PEG), immunoglobulin, albumin and albumin-binding peptides.

Purification can be simplified by conjugating the PSMA-specific binding proteins of the present invention (or the PSMA-specific binding protein produced by the method of the invention) with one or more peptide sequences that confer on the resulting protein conjugate an affinity to certain chromatography column materials. Typical examples for such sequences include, without being limiting, oligo-histidine-tags, Strep-tags, glutathione S-transferase, maltose-binding protein or the albumin-binding domain of protein G.

Conjugation may further be employed to functionalize the PSMA-specific binding proteins of the present invention (or the PSMA-specific binding protein produced by the method of the invention) such that they can be employed as imaging agents. Non-limiting examples of conjugation partners in this regard include enzymes capable of catalyzing chromogenic, chemiluminescent or fluorescent reactions, such as e.g. horseradish peroxidase (HRP), luciferase, β-galactosidase and alkaline phosphatase (AP). Further non-limiting examples of conjugation partners for imaging purposes include fluorescent proteins, such as e.g. green fluorescent protein (GFP), yellow fluorescent protein (YFP), red fluorescent protein (RFP), cyan fluorescent protein (CFP) or infrared fluorescent protein (IFP) as well as fluorescent dyes such as e.g. Fluorescein, Alexa Fluor or Cy dyes. Such protein conjugates are, amongst others, usefully as fluorescent tracers, for example in fluorescence image-guided surgery (FIGS), a medical imaging technique used to detect fluorescently labeled structures during surgery (van Dam, G. M. et al. [2011] Nat. Med. 17:1315-1319; Mondal, S. B. et a. [2014] Adv. Cancer Res. 124:171-211.). Radioactive moieties can also be employed as conjugation partners to functionalize the PSMA-specific binding proteins of the present invention for imaging, including in vivo diagnostics. Such radioactive moieties include for example the group of gamma-emitting isotopes, such as e.g. $^{99m}$Tc, $^{123}$I, $^{125}$I, $^{111}$In and the group of positron emitters, such as e.g. $^{18}$F, $^{64}$Cu, $^{68}$Ga, $^{86}$Y, $^{124}$I, $^{89}$Zr. The group of beta-emitters, such as e.g. $^{131}$I, $^{90}$Y, $^{177}$Lu, $^{67}$Cu, and the group of alpha-emitters, such as e.g. $^{213}$Bi, $^{211}$At are particularly suitable for applications in radio-immuno therapy (RIT), apart from imaging or detection in vivo or in vitro. Also, the above described purification tags may be employed for imaging purposes by detecting the PSMA-specific binding proteins of the present invention (or the PSMA-specific binding protein produced by the method of the invention) e.g. by means of an antibody against said tags.

In addition, conjugation proteins may confer a therapeutic or prophylactic efficacy to the PSMA-specific binding proteins of the present invention (or the PSMA-specific binding protein produced by the method of the invention). For example, the conjugation partner can be an enzyme capable of liberating or activating cytotoxic agents that have been brought into the vicinity of the targeted tissue, for example an enzyme for pro-drug activation, such as e.g. an enzyme selected from the group consisting of carboxy-peptidases, glucuronidases and glucosidases (Bagshawe, K. D. [2009] Curr. Drug Targets 10:152-157; Chen, K.-C. [2011] Bioconjugate Chem. 22:938-948.). The conjugation partner can also itself be a toxic compound, preferably a small organic compound or a polypeptide, such as for example a toxic compound selected from the group consisting of calicheamicin, neocarzinostatin, esperamicin, dynemicin, kedarcidin, maduropeptin, doxorubicin, daunorubicin, auristatin, maitansine, Ricin-A chain, modeccin, truncated *Pseudomonas* exotoxin A, diphtheria toxin and gelonin. In addition, the conjugation partner can be a photosensitizer, such as e.g. bis(triethanolamine)Sn(IV)chlorin $e_6$ (SnChe$_6$); or a radioactive moiety such as those discussed in the preceding paragraph.

Furthermore, the PSMA-specific binding proteins of the present invention (or the PSMA-specific binding protein produced by the method of the invention) can be conjugated to a functional Fc domain, preferably a human functional Fc domain, to enable an immune response of a mammal to target the tissue where the PSMA-binding component of the protein conjugate is located. Also, the PSMA-specific binding proteins of the present invention (or the PSMA-specific binding protein produced by the method of the invention) can be employed as part of a chimeric antigen receptor (CAR) for T-cell therapy by replacing the tumor antigen-specific single-chain variable fragment (scFv) within the fusion protein e.g. with the CD3-zeta transmembrane and endodomain (Baas, T. [2014] SciBX 7:1-7).

The PSMA-specific binding proteins of the present invention (or the PSMA-specific binding protein produced by the method of the invention) can also be conjugated to other binding molecules that either target a different epitope on PSMA or that target different molecules, such as e.g. other proteins, macromolecules or low molecular weight ligands, thereby creating bi-specific (or higher) binding molecules. Non-limiting examples of such binding molecules include Adnectins, Affibodies, Anticalins other than the PSMA-specific binding proteins of the present invention, DARPins or antibody fragments.

"Adnectins" (also referred to as "monobodies"), in accordance with the present invention, are based on the 10th extracellular domain of human fibronectin III (10Fn3), which adopts an Ig-like β-sandwich fold with 2 to 3 exposed loops, but lacks the central disulphide bridge (Gebauer, M. & Skerra, A. [2009] Curr. Opin. Chem. Biol. 13:245-255). Adnectins with the desired target specificity can be genetically engineered by introducing modifications into specific loops of the protein.

"Affibodies", in accordance with the present invention, are a family of antibody mimetics that is derived from the Z-domain of staphylococcal protein A. Affibodies are structurally based on a three-helix bundle domain. An affibody has a molecular mass of around 6 kDa and is stable at high temperatures and under acidic or alkaline conditions. Target specificity is obtained by randomisation of amino acids located in two alpha-helices involved in the binding activity of the parent protein domain (Feldwisch, J & Tolmachev, V. [2012] Methods Mol. Biol. 899:103-126).

"DARPins", in accordance with the present invention, are designed ankyrin repeat domains that provide a rigid interface arising from typically three repeated β-turns. DARPins usually carry three repeats corresponding to an artificial consensus sequence, whereby six positions per repeat are randomised. Consequently, DARPins lack structural flexibility (Gebauer, M. & Skerra, A. [2009] Curr. Opin. Chem. Biol. 13:245-255).

In accordance with the present invention, antibody fragments comprise, inter alia, Fab or F(ab') fragments, F(ab')$_2$, Fv or scFv fragments, single domain VH, VL or V-like domains, such as VhH or V-NAR-domains, as well as multimeric formats such as minibodies, diabodies, tribodies, triplebodies, tetrabodies or chemically conjugated Fab'-multimers (see, for example, Altshuler, E. et al. [2010] Biochem. (Mosc.) 75:1584-1605 or Holliger, P. & Hudson, P. J. [2005] Nat. Biotechnol. 23:1126-1136).

Further non-limiting examples of suitable conjugation partners include chelators such as 1,4,7,10-tetraazacyclododecane-1,4,7,10-tetraacetic acid (DOTA) or diethylene triamine pentaacetic acid (DTPA) or their activated derivatives, nanoparticles and liposomes (Nielsen, U. B. et al. [2002] Biochim. Biophys. Acta 1591:109-118).

The present invention further relates to a pharmaceutical or diagnostic composition comprising at least one of (i) the PSMA-specific binding protein of the invention; (ii) the nucleic acid molecule of the invention; (iii) the vector of the invention; (iv) the host cell of the invention; or (v) the PSMA-specific binding protein produced by the method of the invention.

The term "composition", as used in accordance with the present invention, relates to a composition which comprises at least one of the recited compounds. It may, optionally, comprise further molecules capable of altering the characteristics of the compounds of the invention thereby, for example, stabilizing, modulating and/or enhancing their function. The composition may be in solid or liquid form and may be, inter alia, in the form of (a) powder(s), (a) tablet(s) or (a) solution(s).

In one embodiment, the composition is a pharmaceutical composition.

In accordance with the present invention, the term "pharmaceutical composition" relates to a composition for administration to a patient, preferably a human patient. The pharmaceutical composition of the invention comprises the compounds recited above. The pharmaceutical composition of the present invention may, optionally and additionally, comprise a pharmaceutically acceptable carrier. By "pharmaceutically acceptable carrier" is meant a non-toxic solid, semisolid or liquid filler, diluent, encapsulating material or formulation auxiliary of any type. Examples of suitable pharmaceutically acceptable carriers are well known in the art and include sodium chloride solutions, phosphate buffered sodium chloride solutions, water, emulsions, such as oil/water emulsions, various types of wetting agents, sterile solutions, organic solvents etc. Such pharmaceutically acceptable carriers often contain minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) (poly)peptides, e.g., polyarginine or tripeptides; proteins, such as serum albumin, gelatin, or further immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as ethylenediaminetetraacetic acid (EDTA); sugar alcohols such as mannitol or sorbitol; counterions such as sodium; and/or nonionic surfactants such as polysorbates, poloxamers, or PEG. The pharmaceutical composition may comprise further agents depending on the intended use of the pharmaceutical composition, such as e.g. antitumoral agents for use in the treatment of tumors.

Administration of pharmaceutical compositions of the invention may be effected by different ways, e.g., by intravenous, intraperitoneal, subcutaneous, intramuscular, intradermal, intranasal or intrabronchial administration. Accordingly, it is preferred that the pharmaceutically acceptable carrier is a carrier suitable for these modes of administration. Most preferably, the carrier is a solution that is isotonic with the blood or tissue fluid of the recipient. Compositions comprising such carriers can be formulated by well known conventional methods. Generally, the formulations are prepared by contacting the components of the pharmaceutical composition uniformly and intimately with liquid carriers or finely divided solid carriers or both. Then, if necessary, the product is shaped into the desired formulation.

The pharmaceutical compositions can be administered to the subject at a suitable dose. The dosage regimen will be determined by the attending physician and clinical factors. As is well known in the medical arts, dosages for any one patient depend upon many factors, including the patient's size, body surface area, age, the particular compound to be administered, sex, time and route of administration, general health, and other drugs being administered concurrently. The therapeutically effective amount for a given situation will readily be determined by routine experimentation and is within the skills and judgment of the ordinary clinician or physician. The pharmaceutical composition may be for administration once or for a regular administration over a prolonged period of time. Generally, the administration of the pharmaceutical composition should be in the range of for example 1 µg/kg of body weight to 50 mg/kg of body weight for a single dose. However, a more preferred dosage might be in the range of 10 µg/kg to 20 mg/kg of body weight, even more preferably 100 µg/kg to 10 mg/kg of body weight and even more preferably 500 µg/kg to 5 mg/kg of body weight for a single dose. The components of the pharmaceutical composition to be used for therapeutic administration must be sterile. Sterility is readily accomplished for example by filtration through sterile filtration membranes (e.g., 0.2 μm membranes).

The pharmaceutical composition may be particularly useful for the treatment of tumors and/or neurological diseases, as disclosed below.

In another embodiment, the composition of the invention is a diagnostic composition.

In accordance with the present invention, the term "diagnostic composition" relates to compositions for diagnosing individual patients for their potential response to or curability by the pharmaceutical compositions of the invention. The diagnostic composition of the invention comprises at least one of the compounds recited above. The diagnostic composition may further comprise appropriate buffer(s) etc.

The components of the pharmaceutical or diagnostic composition can be packaged in a container or a plurality of containers, for example, sealed ampoules or vials, as an aqueous solution or as a lyophilized formulation for reconstitution. As an example of a lyophilized formulation, 10-ml vials are filled with 5 ml of 1% (w/v) or 10% (w/v) aqueous solution, and the resulting mixture is lyophilized. A solution for use is prepared by reconstituting the lyophilized compound(s) using either e.g. water-for-injection for therapeutic uses or another desired solvent, e.g. a buffer, for diagnostic purposes. Preservatives and other additives may also be present such as, for example, antimicrobials, anti-oxidants, chelating agents, and inert gases and the like.

The diagnostic compositions of the present invention can be used in in vivo as well as in in vitro or ex vivo diagnostic methods well known in the art. For example, the above described in vivo imaging methods using fluorescent or radioactive labels can be employed to trace the presence of PSMA to specific tissues. Furthermore, methods carried out outside the patient's body such as e.g. immunohistochemical staining of tissues or cells obtained from the patient can be employed for grading the severity of a particular cancer. In addition, measuring the amount of PSMA in brain tissue can be of diagnostic value, for example for measuring levels of PSMA in brain.

The various components of the composition may be packaged as a kit with instructions for use.

Furthermore, the present invention relates to the PSMA-specific binding protein of the invention, the nucleic acid molecule of the invention, the vector of the invention, the host cell of the invention or the PSMA-specific binding protein produced by the method of the invention, for use in therapy and/or diagnosis.

As discussed herein above, dysplastic and neoplastic transformation of prostate tissue is accompanied by a substantial increase in PSMA expression, with the highest levels observed in high-grade, metastatic, and hormone-insensitive cancers. Apart from prostate carcinoma, increased PSMA expression has been observed also for subtypes of bladder carcinoma and Schwannoma and PSMA is also detectable in the neovasculature of many solid tumors. The PSMA-specific binding proteins of the present invention are capable of targeting neovasculature-restricted PSMA and, therefore, offer versatile diagnostic tools for the detection of many solid cancers, including prostate carcinoma. The diagnostic value for the PSMA-specific binding proteins of the present invention further extends to the prediction of a potential relapse following radical prostatectomy, as PSMA is one of the only four independently prognostic markers for prostate-specific antigen (PSA) relapse (Huber, F. et al. [2015] Brit. J. Cancer. 112:140-148). In addition, the PSMA-specific binding proteins of the present invention open excellent therapeutic opportunities, for example by combining the PSMA-specific binding proteins of the present invention with effector molecules, such as e.g. radioactive moieties or toxins.

PSMA is also found in the central nervous system, where it catalyzes the hydrolysis of N-acetylaspartylglutamate (NAAG), the most abundant peptidic neurotransmitter, to glutamate and N-acetylaspartate (NAA). Glutamate is a common and abundant excitatory neurotransmitter in the central nervous system which is detrimental to neurons when present in excessive concentrations due to the overstimulation and -activation of glutamate receptors. For these reasons, glutamate has been implicated in many neurological diseases and disorders and, accordingly, a specific control of PSMA activity in the brain is of high importance. Accordingly, the PSMA-specific binding proteins of the present invention may serve to diagnose the level of PSMA expression in the brain.

Finally, Zhang, T. et al. [2012] (PLoS One 7:e37139) have shown that upregulation of FOLH1 (i.e. the gene encoding PSMA) gene expression is predictive of the ileal Crohn's disease (CD) phenotype compared to non-CD. Accordingly, PSMA is additionally a biomarker for ileal CD phenotype in the macroscopically disease unaffected proximal margin of resected ileum from ileal CD subjects.

Accordingly, the present invention further relates to the PSMA-specific binding protein of the invention, the nucleic acid molecule of the invention, the vector of the invention, the host cell of the invention or the PSMA-specific binding protein produced by the method of the invention, for use in the therapy and/or diagnosis of tumors, Crohn's disease and/or neurological diseases.

The term "tumor", in accordance with the present invention, refers to a class of diseases or disorders characterized by uncontrolled division of cells and encompasses all types of tumors, such as e.g. cancerous tumors and benign tumors as well as solid tumors and non-solid tumors. Cancerous tumors are further characterized by the ability of these tumors to spread, either by direct growth into adjacent tissue through invasion, or by implantation into distant sites by metastasis (where tumor cells are transported through the bloodstream or lymphatic system).

Preferably, the tumor is a cancerous tumor, more preferably a solid tumor. Even more preferably, the tumor is selected from the group consisting of prostate cancer, bladder carcinoma, Schwannoma, glioma, breast cancer, small-cell lung cancer and non-small cell lung cancer. Most preferably, the cancer is prostate cancer.

The term "Crohn's disease", as used herein, relates to an inflammatory disease of the digestive system which may affect any part of the gastrointestinal tract from mouth to anus. The disease is also known as granulomatous colitis and regional enteritis. Symptoms of Crohn's disease can vary significantly among afflicted individuals. The main gastrointestinal symptoms are abdominal pain, diarrhea (which may be visibly bloody), vomiting, or weight loss. Crohn's disease can also cause complications outside of the gastrointestinal tract such as skin rashes, arthritis, and inflammation of the eye. The precise cause of Crohn's disease is not known. The disease occurs when the immune system attacks the gastrointestinal tract. This autoimmune activity produces inflammation in the gastrointestinal tract, and therefore Crohn's disease is classified as an inflammatory bowel disease.

The term "neurological diseases", in accordance with the present invention, refers to disorders that affect the nervous system, i.e. the brain, spinal cord, and the nerves. Preferably, the neurological diseases are selected from the group consisting of stroke, amyotrophic lateral sclerosis (ALS), schizophrenia, diabetic neuropathy, severe head injury (SHI), traumatic brain injury (TBI), neuropathic pain, inflammatory pain, drug addiction, as well as neurodegenerative diseases such as Parkinson's disease and Huntington's disease.

All the cancer types and neurological diseases referred to herein are well known to the skilled person and are defined in accordance with the pertinent art and the common general knowledge of the skilled person.

Unless otherwise defined, all technical and scientific terms used herein have the same meaning as commonly understood by one of ordinary skill in the art to which this invention belongs. In case of conflict, the patent specification, including definitions, will prevail.

All the sequences accessible through the Database Accession Numbers cited herein are within the scope of the present invention and also include potential future updates in the database, in order to account for future corrections and modifications in the entries of the respective databases, which might occur due to the continuing progress of science.

All amino acid sequences provided herein are presented starting with the most N-terminal residue and ending with the most C-terminal residue (N→C), as customarily done in the art, and the one-letter or three-letter code abbreviations as used to identify amino acids throughout the present invention correspond to those commonly used for amino acids.

Regarding the embodiments characterized in this specification, in particular in the claims, it is intended that each embodiment mentioned in a dependent claim is combined with each embodiment of each claim (independent or dependent) said dependent claim depends from. For example, in case of an independent claim 1 reciting 3 alternatives A, B and C, a dependent claim 2 reciting 3 alternatives D, E and F and a claim 3 depending from claims 1 and 2 and reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Similarly, and also in those cases where independent and/or dependent claims do not recite alternatives, it is understood that if dependent claims refer back to a plurality of preceding claims, any combination of subject-matter covered thereby is considered to be explicitly disclosed. For example, in case of an independent claim 1, a dependent claim 2 referring back to claim 1, and a dependent claim 3 referring back to both claims 2 and 1, it follows that the combination of the subject-matter of claims 3 and 1 is clearly and unambiguously disclosed as is the combination of the subject-matter of claims 3, 2 and 1. In case a further dependent claim 4 is present which refers to any one of claims 1 to 3, it follows that the combination of the subject-matter of claims 4 and 1, of claims 4, 2 and 1, of claims 4, 3 and 1, as well as of claims 4, 3, 2 and 1 is clearly and unambiguously disclosed.

The above considerations apply mutatis mutandis to all appended claims. To give a non-limiting example, the combination of claims 8, 5 and 4 is clearly and unambiguously envisaged in view of the claim structure. The same applies for example to the combination of claims 8 and 5, etc.

The invention is illustrated with the following figures which show:

FIG. 1: PSMA variants used in this study. Three recombinant versions of the PSMA extracellular domain were produced as secreted proteins in Schneider S2 cells and purified via optimized protocols using size-exclusion chromatography (SEC) as final purification step. (A) Amino acid sequence at the N-terminus of the PSMA ectodomain (i.e. residues 44-750; UniProt ID: Q04609). Avi-PSMA: the TEV-cleavable Avi-tag (SEQ ID NO:50) is recognized in vivo/in vitro by BirA biotin ligase, allowing the attachment of a single biotin group at the lysine residue shown in bold. SF-PSMA: the cleavable N-terminal extension with the Strep-tag II and FLAG-tag (SEQ ID NO:51) which were employed for purification and panning, respectively. Furthermore, the wild-type ectodomain was produced with its native N-terminus (rhPSMA). (B) Elution profiles from a Superdex HR200 size-exclusion column documenting monodispersity of PSMA preparations. (C) Coomassie-stained SDS-PAGE of purified PSMA variants. Purity of all protein versions was >98%.

Figure 2B:
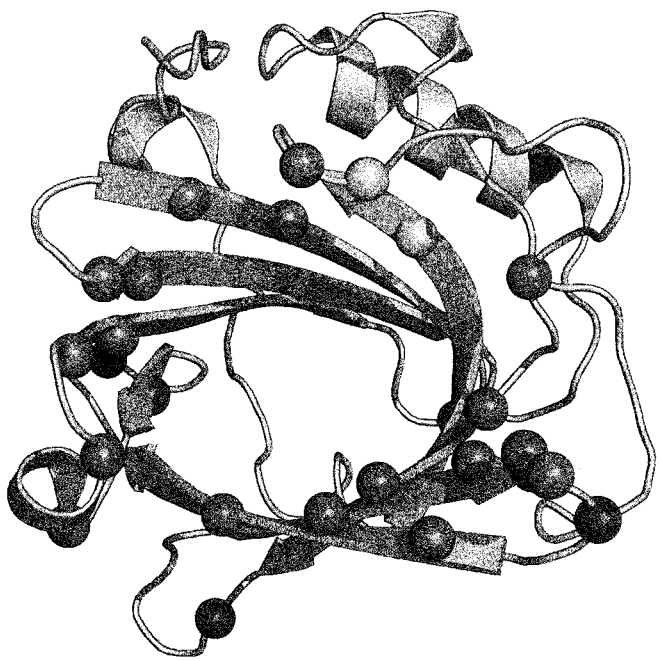

FIG. 2: Structure and sequence analysis of the selected PSMA-specific Anticalins in comparison with wild-type Lcn2. (A, B) Structure of human Lcn2 (PDB code: 1L6M). A rigid β-barrel composed of eight β-strands that are connected by four structurally variable loops at its open end is depicted in cartoon representation. Positions of residues that were randomized in the Lcn2 random library used here are shown as grey balls. (C) Sequence alignment of the selected Anticalins with the template Lcn2, also illustrating the naïve Anticalin library (randomized positions denoted "x"). A3 was selected from the original combinatorial library, while the subsequent variants emerged during affinity maturation of this clone in several iterations. Positions where a given Anticalin differs from the respective parent variant are shown in bold. The central gene cassette flanked by the pair of BstXI sites is underlined; β-strands and loops are labeled by letters A through H and numbers 1 through 4, respectively.

Figure 3A:
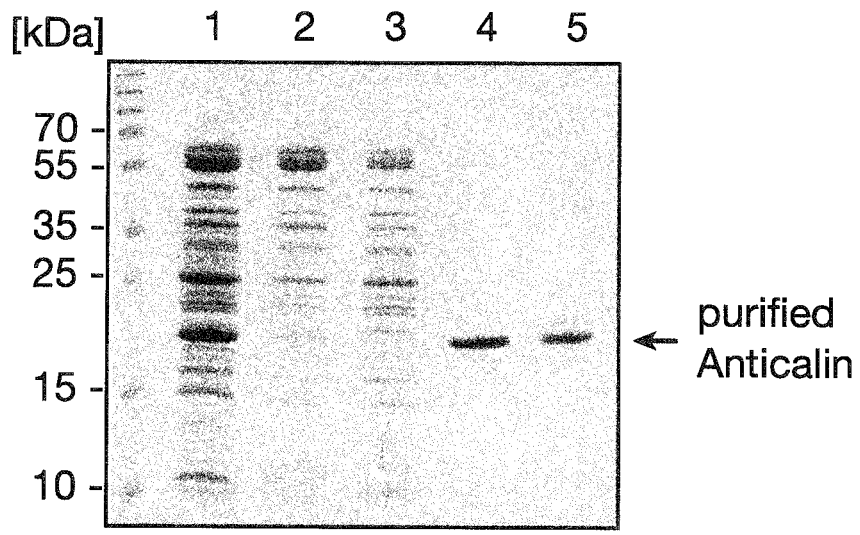
Figure 3B:
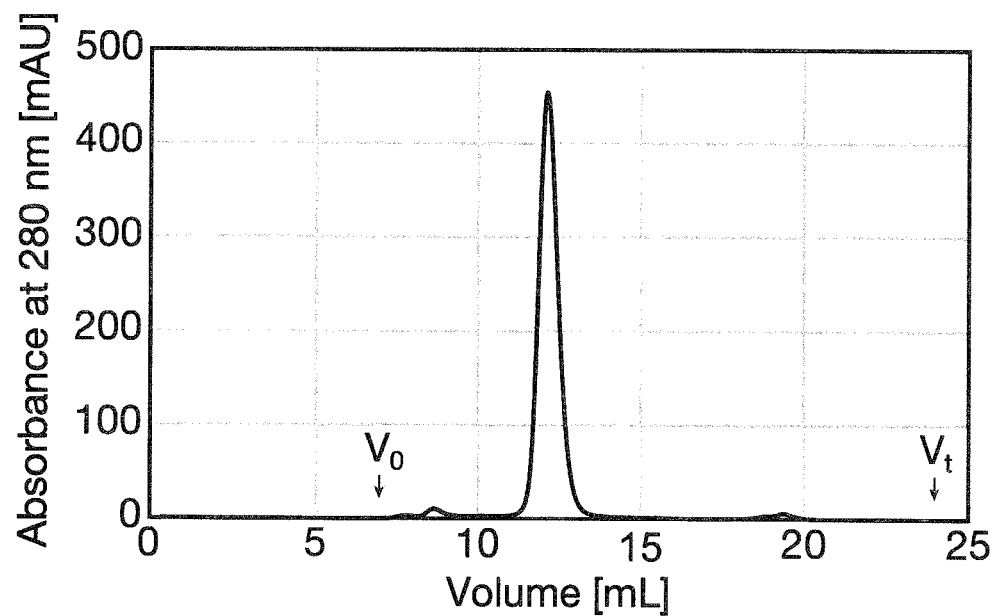
Figure 4A:
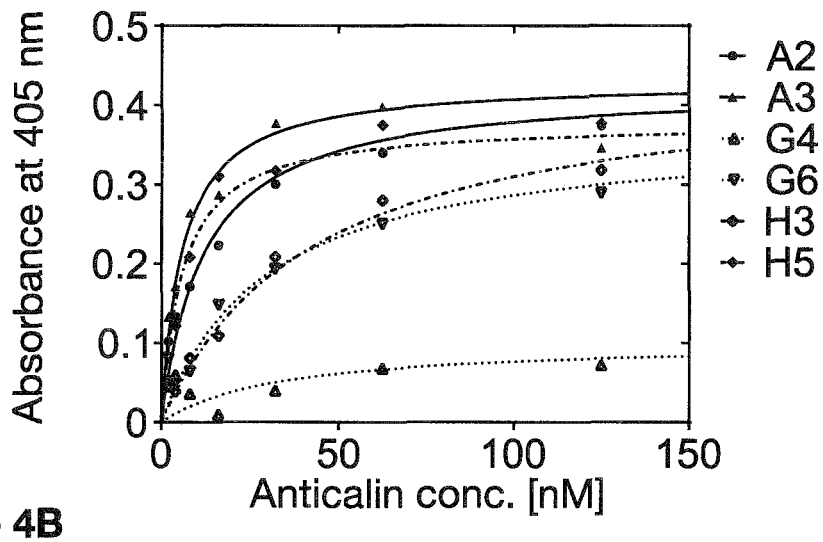
Figure 4B:
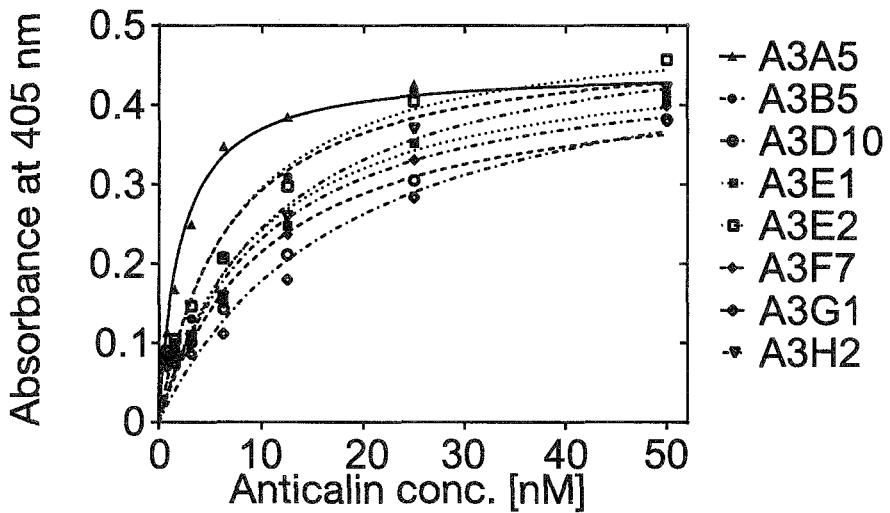
Figure 4C:
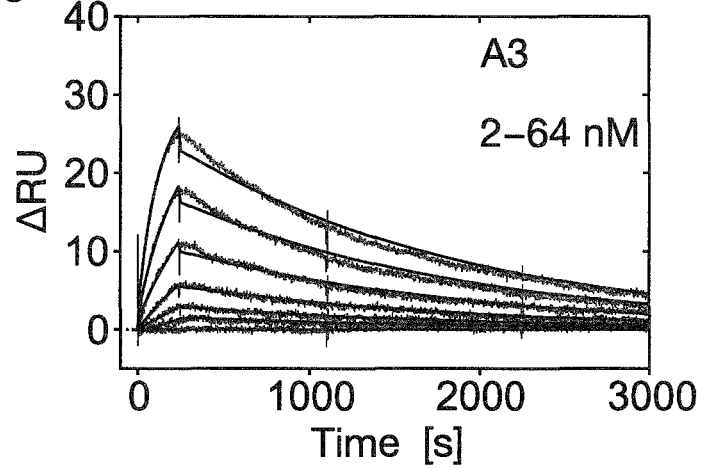
Figure 4D:
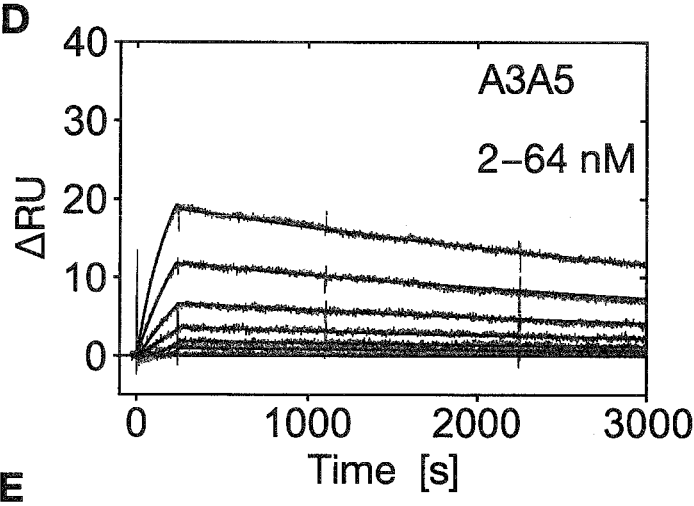
Figure 4E:
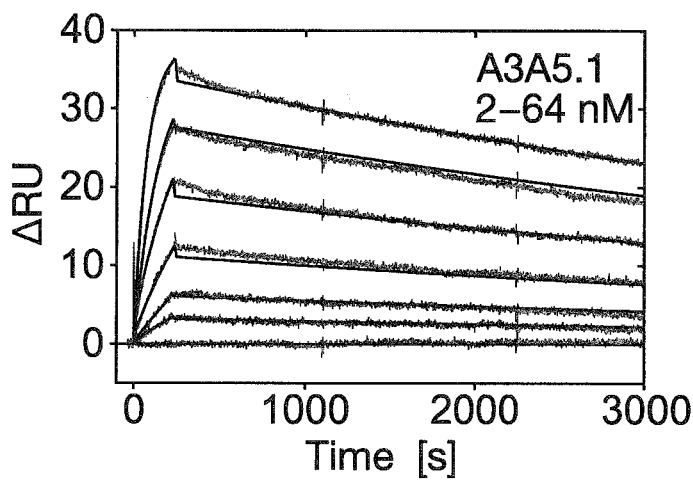
Figure 4F:
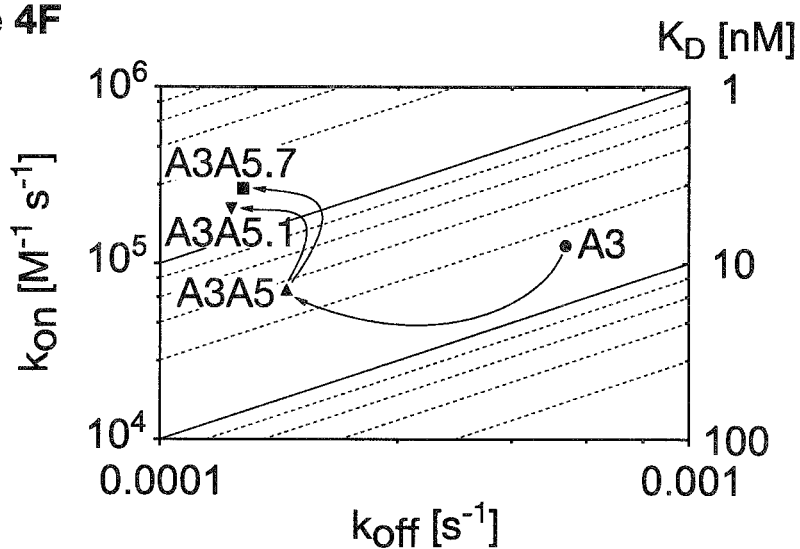

FIG. 3: Anticalin expression and purification. The selected PSMA-specific Anticalin A3A5 is shown as an example. A3A5 was produced as a soluble protein via periplasmic secretion in E. coli and purified by StrepTactin affinity chromatography and SEC on a Superdex HR75 column. (A) Coomassie-stained 15% SDS-PAGE illustrating A3A5 purification. Fractions: 1, periplasmic extract; 2, flow-through from StrepTactin column; 3, washing step; 4, elution step; 5, pooled fractions after SEC. (B) Elution profile from the Superdex HR75 column documents monodispersity of the A3A5 protein preparation. The elution volume corresponds to a molecular weight of 21 kDa as expected for the monomeric Anticalin. Peak fractions were pooled, concentrated and used for subsequent experiments.

FIG. 4: Anticalin affinities towards PSMA as determined by ELISA and BIAcore measurements. Binding activities of Anticalins selected from the original naïve library (A) or resulting from subsequent affinity maturation of the A3 variant (B) were compared in an ELISA. A 96-well MaxiSorp plate was coated with rhPSMA (or ovalbumin as a negative control, not shown) and purified Anticalin variants were applied in dilution series. Anticalin binding was detected using StrepTactin/AP conjugate, followed by chromogenic reaction. Absorption was plotted against the Anticalin concentration and data were analyzed by curve fitting. Binding curves for the best performing clones A3 and A3A5 are shown as solid lines. (C-E) SPR sensograms measured for Anticalins A3, A3A5 and A3A5.1 on a BIAcore 2000 instrument. Approximately 500 RU of rhPSMA was immobilized on a CM5 sensor chip by amine coupling. A dilution series from 64 to 2 nM of the purified Anticalin in HBS was applied and the resulting curves were fitted according to a Langmuir 1:1 binding model. (F) Comparison of parameters from real-time SPR analysis for Anticalins investigated in C-E, together with A3A5.7, in a $k_{on}/k_{off}$ plot.

FIG. 5: Detection of PSMA expressed on cells with the Anticalin A3A5 by immunofluorescence microscopy. (A) Quantification of PSMA levels in cell lysates. Cell lysates were separated by 10% SDS-PAGE, transferred onto a PVDF membrane and immunostained with the antibody GCP04, followed by an anti-mouse/HRP conjugate. Expression levels were significantly higher in PSMA-transfected HEK293T cells compared to endogenously expressed PSMA in the LNCaP prostate cell line. Tubulin a was used as internal control. (B) PSMA-positive cell lines (LNCaP, HEK293T/PSMA) and corresponding PSMA-negative controls (PC-3, HEK293T) were fixed on glass coverslips by paraformaldehyde and permeabilized. Fixed cells were probed with 0.5 µM Anticalin A3A5, followed by detection via StrepMAB-Immo and an Alexa Fluor 488-labeled anti-mouse secondary antibody. Both plasma membrane and cytoplasmic staining is detectable for PSMA-positive LNCaP (panel H) and, even more pronounced, HEK293T/PSMA (panel D) cells. PSMA-negative PC-3 prostate cell line and non-transfected HEK293T cells revealed no staining. Nuclei were visualized with DAPI (scale bar, 20 µm).

Figure 5A:
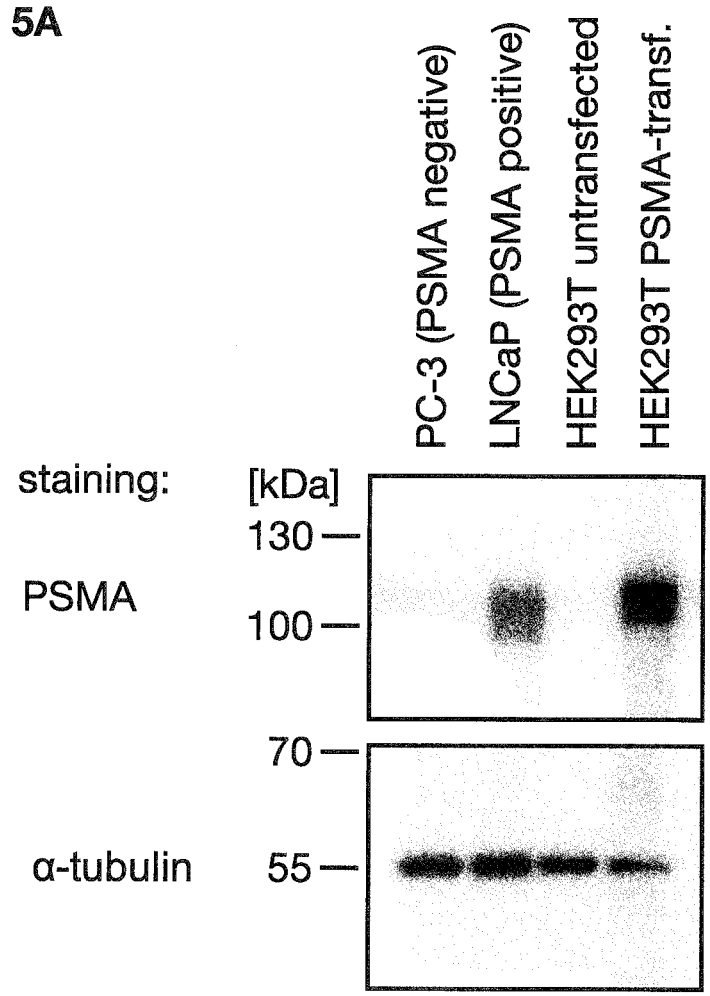
Figure 6:
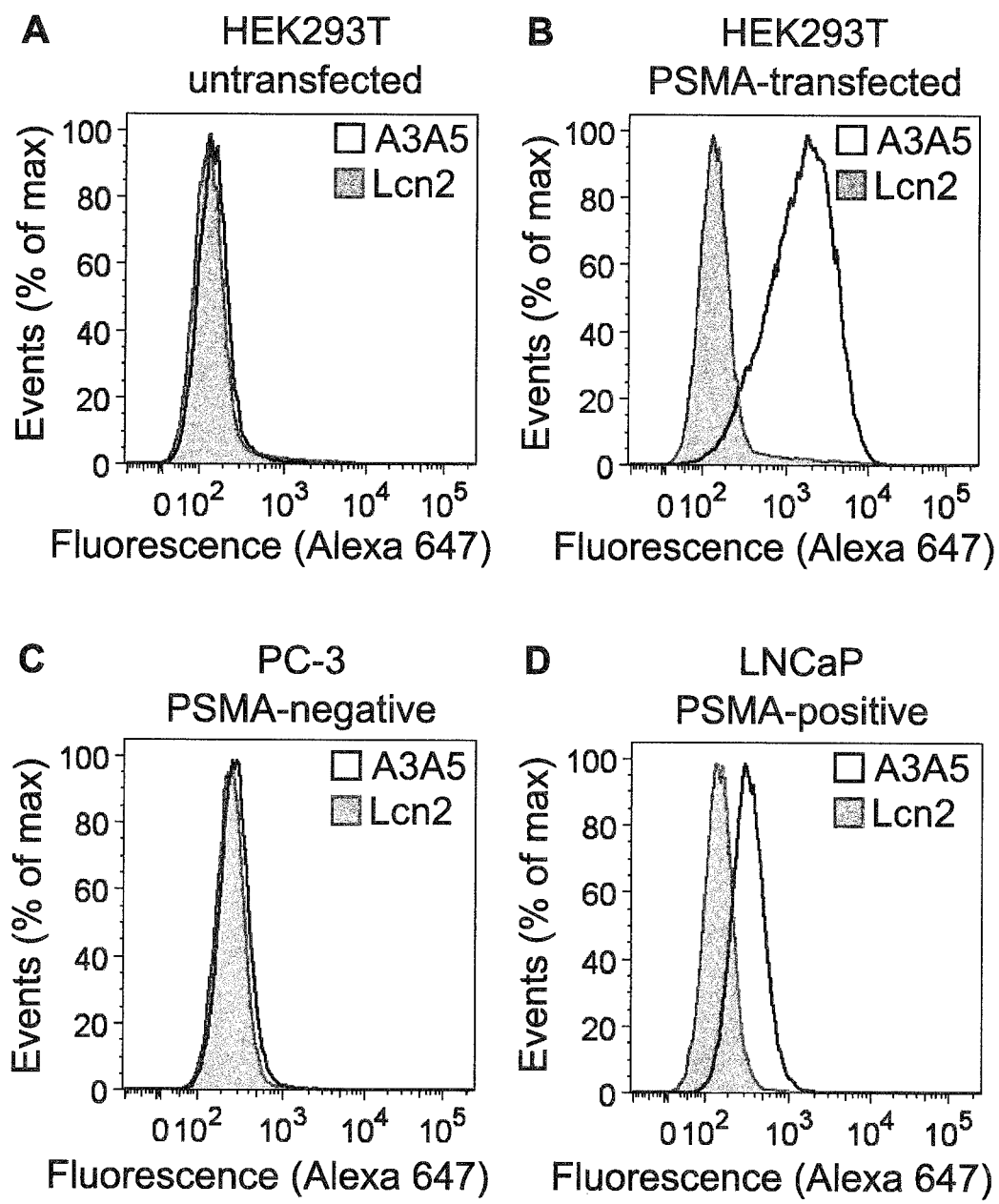

FIG. 6: Flow cytometric analysis of PSMA expression on live cells. Two cell lines of prostatic origin, LNCaP (PSMA$^+$, panel D) and PC-3 (PSMA$^-$, panel C), along with HEK293T/PSMA cells (panel B; with the matching non-transfected HEK293T included as control, panel A) were used to assess binding of 1 µM Anticalin to PSMA in its native environment on the surface of live cells. Anticalin binding was detected with StrepMAB-Immo and a secondary anti-mouse antibody labeled with Alexa Fluor 647. Open histograms (black line) show the staining profile for the Anticalin A3A5 while filled histograms (grey) indicate the background fluorescence intensity measured for wild-type Lcn2. A3A5 staining intensity is weaker for LNCaP cells due to lower amounts of PSMA present at the cell surface, in agreement with Western blotting and immunofluorescence data (cf. FIG. 5). A minimum of 20,000 cells were analyzed for each sample using FlowJo software.

Figure 7:
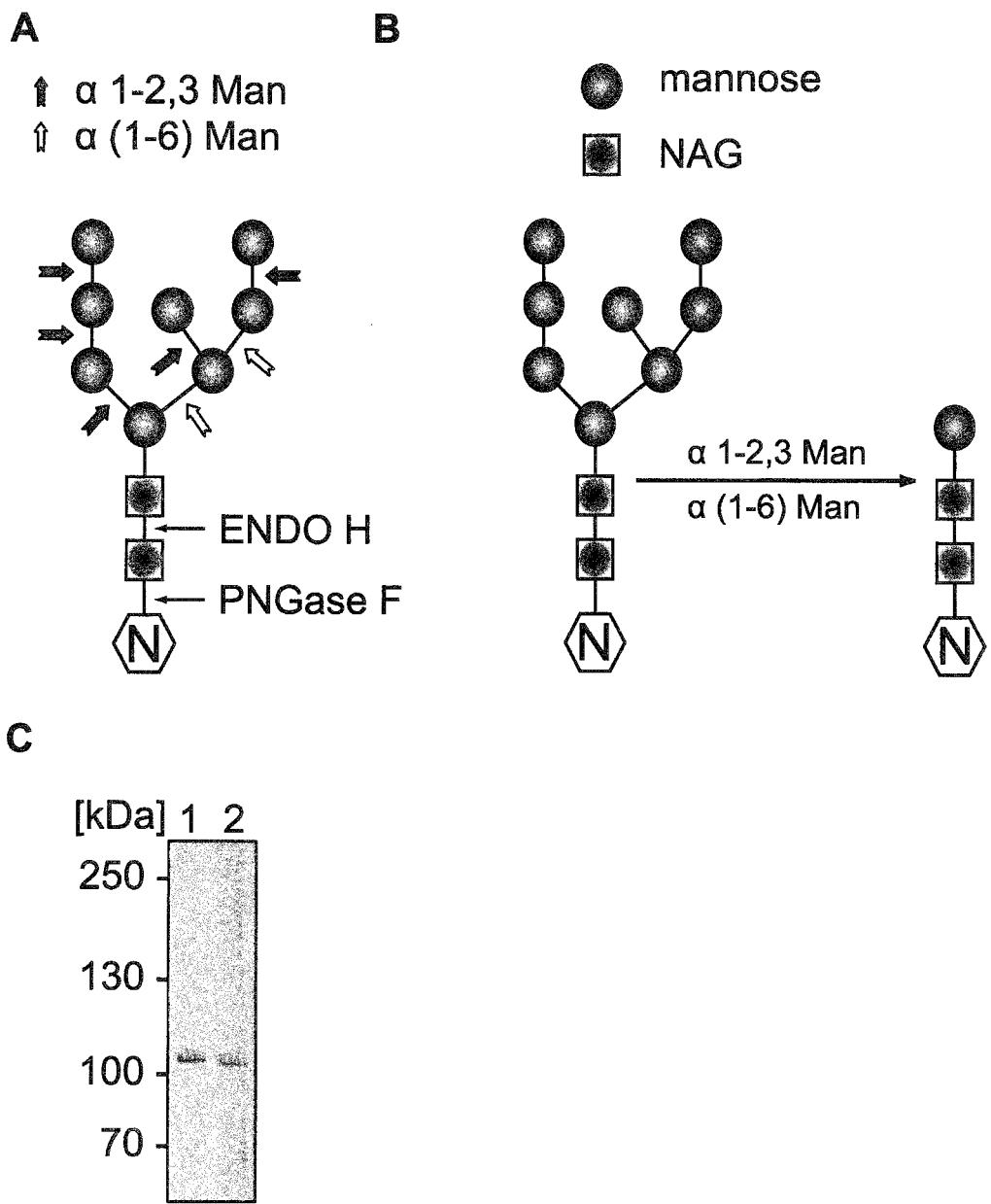

FIG. 7: Partial deglycosylation of SF-PSMA using a mixture of α-mannosidases. (A) Specificity of endoglycosidases on a "typical" high-mannose oligosaccharide chain (N represents the asparagine residue as part of a glycosylation sequon in a protein). (B) Expected processing of N-linked sugars by the combination of α1-2,3 mannosidase and α1-6 mannosidase used in this study. (C) SDS-PAGE analysis of the fully glycosylated (lane 1) and partially deglycosylated (lane 2) recombinant PSMA proteins. Samples were resolved using a 4-12% gradient gel (NUPAGE, Invitrogen) and silver-stained.

The following examples illustrate the invention:

EXAMPLE 1: GENERAL METHODS

Expression and purification of human PSMA variants
Three variants of human PSMA featuring different N-terminal tags were used (FIG. 1). These PSMA variants were produced as secreted proteins in Schneider S2 cells. The conditioned media (SFX serum-free medium; ThermoFisher Scientific, SH30278) was concentrated, dialyzed by tangential flow filtration (TFF; Millipore) and target proteins were purified according to the following protocols.

Wild-Type rhPSMA:
Cloning, expression and purification of the extracellular part of human PSMA (rhPSMA; denoted rhGCPII in the original paper, residues 44-750) were carried out as described.[23] The protein was purified using ion-exchange chromatography (Q and SP Sepharose FF), affinity chromatography on Lentil-Lectin Sepharose, and size-exclusion chromatography (SEC) on a Superdex 16/60 HR200 column with 20 mM Tris/HCl, 150 mM NaCl, pH 8.0 as mobile phase (all resins/columns from GE Healthcare Bio-Sciences). Purified rhPSMA was concentrated to 1 mg/mL and kept at −80° C. until further use.

Avi-PSMA:
The extracellular part of human PSMA comprising an N-terminal Avi-tag (Avi-PSMA) was prepared as previously described.[24] Briefly, the recombinant protein was expressed in Schneider S2 cells stably transfected with *E. coli* biotin protein ligase localized to the endoplasmic reticulum. After coexpression of the fusion protein, single-step purification was carried out using a resin with an immobilized Streptavidin mutant (Streptavidin Mutein Matrix, Roche, 03708152001) with biotin elution. SEC as above yielded the final preparation with >95% purity. Avi-PSMA was aliquoted, shock-frozen in liquid nitrogen and stored at −80° C. until further use.

SF-PSMA:
A Strep-FLAG-TEV sequence (FIG. 1A) was introduced at the N-terminus of the coding region for the extracellular part of human PSMA (residues 44-750) by polymerase chain reaction (PCR). The PCR product was cloned via Bg/II and XhoI restriction sites on pMT/BiP/V5-His A (Invitrogen) resulting in the plasmid pMT/BiP/SF-PSMA. This plasmid, together with pCoBLAST which confers resistance to Blasticidine (InvivoGen, ant-bl-1), was transfected into Schneider S2 cells using Effectene (Qiagen, 301425) according to the manufacturer's protocol. Two days post transfection, transfectants were selected by adding 50 µg/mL Blasticidine into the SFX serum-free medium supplemented with 10% v/v FBS. Approximately three weeks post transfection, the Blasticidine-resistant S2 cell population was transferred into SFX medium, expanded and expression of SF-PSMA was induced by the addition of 0.7 mM CuSO$_4$ at a cell density of 1×10$^6$/mL. Seven days post induction, approximately 30×10$^6$ cells per mL were harvested by centrifugation and the conditioned media was concentrated by tangenital flow filtration to 1/10 of the original volume. Concentrated media was dialyzed three times against at least 10-fold excess of 50 mM Tris/HCl, 150 mM NaCl, pH 8.0 (TBS). Dialyzed media was loaded onto a 5 mL Strep-Tactin column (IBA, 2-1208-025) equilibrated in TBS and the SF-PSMA protein was eluted with 3 mM D-desthiobiotin (IBA, 2-1000-001) in TBS. Pooled elution fractions containing pure SF-PSMA were concentrated and loaded onto a Superdex 16/60 HR200 size-exclusion column equilibrated in TBS. Fractions corresponding to the SF-PSMA dimer were pooled, concentrated to 1 mg/mL by ultrafiltration, snap-frozen in liquid nitrogen and stored at −80° C. until further use. The typical yield of SF-PSMA was about 5 mg per liter culture with purity >99% (FIG. 1).

For partial deglycosylation, SF-PSMA (10 µg) was mixed with both α1-2,3 Mannosidase (64 U) and α1-6 Mannosidase (80 U; both from New England Biolabs) in a volume of 50 µL. The deglycosylation reaction was carried out at 37° C. for 4 h and monitored by SDS-PAGE.

Selection of Anticalins Against PSMA Via Phage Display

A previously published Lcn2 library (Gebauer, M. et al. [2013] J. Mol. Biol. 425:780-802) served as a starting point for the selection of PSMA-specific Anticalins. In this library, twenty specified amino acid positions within the structurally variable loops and adjoining regions around the natural ligand pocket were randomized to generate a genetic library amenable for phage display selection of lipocalin variants with prescribed binding activities. This Anticalin library was encoded on the pNGAL108 plasmid in frame with the N-terminal OmpA signal peptide and the C-terminal Strep-tag II, followed by the pIII minor coat protein of M13 bacteriophage (Gebauer, M. & Skerra, A. [2012] Meth. Enzymol. 503:157-188).

The successful selection of PSMA-specific lipocalin variants from the naïve library was carried out by on-bead panning essentially following a published procedure (Gebauer, M. & Skerra, A. [2012] Meth. Enzymol. 503:157-188). To this end, 100 nM SF-PSMA was first incubated with $10^{11}$ phages of the library in TBS+2% (w/v) BSA in a total volume of 500 µL for 1 h at room temperature. SF-PSMA/phage complexes were then captured during 10 min using 25 µL of Anti-FLAG M2 magnetic beads (Sigma-Aldrich, M8823). Following magnetic separation, unbound phages were discarded and the beads were washed ten times with TBS containing 0.1% v/v Tween 20 (TBS/T; 0.5 mL per a wash cycle). Finally, bound phagemid/SF-PSMA complexes were released from the resin by competitive elution with an excess of the FLAG peptide (300 µL of 200 µg/mL; Sigma-Aldrich, F3290) in TBS/T. Amplification of eluted phagemids was performed as described.[21] A total of four panning cycles were carried out in this way using $10^9$-$10^{11}$ phages from the preceding panning round as an input (exact number of phages determined from titer). The phasmid DNA of the enriched population from the last cycle was isolated with the QIAgen Plasmid Midiprep Kit (QIAgen, 12143) and subjected to subcloning on the plasmid pNGAL98 for soluble expression and ELISA screening (see below).

For affinity maturation via phage display, the panning procedure was modified as follows: instead of SF-PSMA, Avi-PSMA was incubated with the blocked phagemid library in solution and Avi-PSMA/phagemid complexes were captured via Streptavidin magnetic beads (50 µL; Roche, 11641778001; rounds 1 and 3) or Neutravidin-coated Sera-Mag Speed beads (50 µL; Thermo Scientific, 78152104011150, rounds 2 and 4) in an alternating manner. 10 nM Avi-PSMA target was used for the first two rounds whereas the concentration was decreased to 1 nM in rounds 3 and 4. Bead-bound phages were washed under more stringent conditions with first TBS/T containing 0.1 mM D-desthiobiotin as well as 100 nM rhPSMA for 30 min (to select for slow $k_{off}$), followed by nine washing steps with TBS/T+desthiobiotin for 1 min. Bound phages were finally released by acidic elution with 350 µL of 0.1 M glycine/HCl pH 2.2, for 10 min and immediately neutralized by addition of 55 µL 0.5 M Tris base (pH 10.5).

Affinity maturation via phage display A second generation Anticalin library was generated by error prone PCR based on the Anticalin A3 template obtained from the original anti-PSMA selection campaign using the GeneMorph II random mutagenesis kit (Agilent Technologies, 200550). First, the Anticalin gene was amplified from the pNGAL98 expression vector by Taq DNA polymerase using the primers 5'-AGA CAG CTA TCG CGA TTG CA (SEQ ID NO:52) and 5'-CGC AGT AGC GGT AAA CG (SEQ ID NO:53). The amplified gene was purified from an agarose gel with the QIAquick Gel Extraction Kit (QIAgen, 28704) and used as a template for the error-prone PCR, which was carried out according to the manufacturer's protocol. Shortly, 1 ng of the template together with the primers BstXI-for (5'-cag gac aac caa ttc cat ggg) (SEQ ID NO:54) and BstXI-rev (5'-gga ggc cca gag att tgg) (SEQ ID NO:55) that flank the central region of the Anticalin gene, comprising all four previously randomized loops, were used to introduce an optimal number of 4-6 nucleotide mutations per gene during a total of 30 reaction cycles. The resulting PCR product was purified from agarose gel and ligated with the phage display vector pNGAL108 using BstXI restriction sites, followed by electroporation of E. coli XL1-Blue cells as described (Gebauer, M. & Skerra, A. [2012] Meth. Enzymol. 503:157-188). The complexity of the resulting sublibrary was assessed by plating a dilution series of transformed cells and revealed typically about $10^8$-$10^9$ individual clones. Finally, phage particles were produced and used for the panning rounds as described above.

Identification of PSMA-Specific Anticalin Candidates by High-Throughput ELISA

Enriched lipocalin variants from phage display were subjected to ELISA screening after subcloning of the central BstXI gene cassette on pNGAL98, which also encodes the N-terminal OmpA signal sequence directing the expressed protein into the bacterial periplasm and a C-terminal Strep-tag II for purification (Schmidt, T. G. & Skerra, A. [2007] Nat. Protoc. 2:1528-1535). After transformation of E. coli TG1-F- (Kim, H. J. et al. [2009] J. Am. Chem. Soc. 131:3565-3576) with the ligation mixture, randomly picked colonies were inoculated in a 96-well plate filled with 100 µL of Terrific broth (TB) media supplemented with 100 µg/mL ampicillin per well. Anticalin expression was induced at an optical density of $OD_{550}$=0.3-0.5 by addition of 20 µL TB/Amp containing 1.2 µg/mL anhydrotetracycline (aTc; ACROS Organics, 233131000) overnight at 20° C. The periplasmic extract was prepared as previously described[21] and applied to 96-well MaxiSorp plates (Nunc, 442404) coated with rhPSMA (5 µg/mL in TBS) and blocked with BSA. Ovalbumin (10 µg/mL in TBS) served as non-related control protein in parallel. After 1 h incubation at room temperature, plates were washed three times with PBS/T and bound lipocalin variants were detected by means of their C-terminal Strep-tag II using StrepTactin conjugated to alkaline phosphatase (IBA, 2-1503-001), diluted 1:5,000 in PBS, for 1 h. Signals were developed by hydrolysis of 0.5 mg/mL p-nitrophenyl phosphate in 0.1 M NaCl, 5 mM $MgCl_2$, 0.1 M Tris/HCl, pH 8.8, and monitored via absorbance measurement at 405 nm with an Infinite 200 PRO microplate reader (Tecan).

Affinity Maturation Via Bacterial Surface Display

First, a library based on the Lcn2 variant A3A5 was constructed via error-prone PCR as described above. The resulting PCR product was digested with BstXI, purified and ligated with the plasmid pNGAL146 (Gebauer, M. & Skerra, A. [2012] Meth. Enzymol. 503:157-188), which encodes a fusion protein between the lipocalin and the β-domain of the bacterial autotransporter EspP. The resulting Anticalin library was used for transformation of electrocompetent E. coli JK321 cells (Jose, J. et al. [1996] Gene 178:107-110), followed by plating on LB/Amp agar.

For EspP-mediated bacterial surface display, cell cultivation, target incubation, staining and fluorescence-activated cell sorting (FACS) were carried out as described before (Binder, U. et al. [2010] J. Mol. Biol. 400:783-802). In brief, colonies were scraped from the agar plate, suspended in 50 mL of LB/Amp and shaken for 1 h at 37° C. This culture was used to inoculate a 50 mL LB/Amp overnight culture at 30°

C. which in turn was used the next day to inoculate 50 mL LB/Amp at 30° C. with a starting $OD_{550}=0.15$. Gene expression was induced at $OD_{550}=0.5$ with 10 ng/mL aTc for 2.5 h. Cells from 100-200 μL of this culture were spun down in an Eppendorf tube for 3 min at 4° C., washed once in PBS with 3% w/v BSA (PBS/BSA) and resuspended in 1000 μL PBS/BSA supplemented with 2.5 or 1 nM Avi-PSMA (see below). After 1 h incubation under gentle shaking at 4° C. the cells were washed and incubated in the presence of 100 nM purified A3A5 Anticalin as competing PSMA ligand. After that, cells were washed once and remaining bound PSMA was stained by subsequent incubation with PBS/BSA containing 25 μg/mL streptavidin/phycoerythrin (SA/PE; BD Biosciences, 554061) and 3 μM Dy634-labelled A3C5 Fab fragment directed against a peptide tag as part of the Anticalin-autotransporter fusion protein (Binder, U. et al. [2010] J. Mol. Biol. 400:783-802). Following 30 min of incubation on ice the cells were finally washed once with PBS and then applied to a FACSAria Cell-Sorting System (BD Biosciences).

For fluorescence detection of PE, a 488 nm laser diode and a 530/30 band pass filter was used, while Dy634 was detected using a HeNe laser (633 nm) and a 660/20 band pass filter. In each of the four selection rounds the fraction comprising the 0.3-0.5% most fluorescent cells were sorted and subsequently cultivated for the next cycle. Stringency of the selection was gradually increased by lowering the concentration of Avi-PSMA (2.5 nM in round 1 and 2; 1 nM in round 3 and 4) and increasing the duration of the competitive dissociation step from 3 h in round 1 to 30 h in round 4. Finally, single clones were analyzed by DNA sequencing of the BstXI gene cassette as well as individual cultivation, staining and single-clone FACS analysis. For further analysis of promising candidates, the BstXI gene cassette was subcloned on pNGAL98.

Anticalin Expression and Purification

Anticalin candidates were produced via periplasmic secretion in E. coli using the vector pNGAL98 in shaker flasks according to a standard procedure (Gebauer, M. & Skerra, A. [2012] Meth. Enzymol. 503:157-188). Transformed E. coli TG1-F⁻ were cultured in LB medium supplemented with 100 mg/L ampicillin at 22° C. and 180 rpm until exponential growth was reached. Then, expression was induced for 3 h by addition of aTc to a final concentration of 200 μg/L. Bacteria were harvested by centrifugation and the periplasmic extract was prepared by a mild osmotic shock and subsequent removal of spheroplasts by centrifugation. The recombinant Anticalins were purified by means of StrepTactin affinity chromatography (Schmidt, T. G. & Skerra, A. [2007] Nat. Protoc. 2:1528-1535), followed by size-exclusion chromatography on a Superdex 16/60 HR75 column equilibrated in PBS.

Anticalin Affinity Measurement by ELISA

50 μL of rhPSMA (5 μg/mL in TBS) was directly adsorbed onto the surface of a MaxiSorp 96-well plate overnight at 4° C. Similarly, ovalbumin-coated wells (10 μg/mL in PBS) were used as a negative control. After blocking with 250 μL of 2% w/v BSA for 1 h at room temperature, 50 μL from a serial Anticalin dilution in PBS was added to each well and incubated for 1 h. The plates were washed three times and bound Anticalins were detected with StrepTactin-AP as described further above. The data were analyzed using Prism 5 software (GraphPad) and absorption values (A) were fitted according to the formula $\Delta A = A_{max} \cdot [L_{tot}]/(K_D+[L_{tot}])$ with the concentration of the applied lipocalin variant $[L_{tot}]$ and the dissociation constant $K_D$.

BIAcore Real-Time Affinity Measurements

Surface plasmon resonance (SPR) spectroscopy was performed on a BIAcore 2000 instrument (BIAcore) following published procedures (Gebauer, M. et al. [2013] J. Mol. Biol. 425:780-802; De Crescenzo, G. et al. [2008] J. Mol. Recognit. 21:256-266). rhPSMA (1 nM in 10 mM Na-acetate pH 5.0) was immobilized on a CM5 sensor chip (BIAcore) using an amine coupling kit (GE Healthcare, BR100050), resulting in around 500 resonance units (ΔRU). The purified Anticalins were diluted in HEPES buffered saline (HBS; 10 mM HEPES/NaOH, 150 mM NaCl, pH 7.4) with 0.005% v/v Tween 20 to concentrations from 64-2 nM. The instrument was operated using the same running buffer at a flow rate of 25 μL/min. Complex formation was monitored by injection of 100 μL of the Anticalin solution and dissociation was observed for 100 min. Regeneration of the sensor chip was achieved by up to four injections of 10 μL glycine/HCl, pH 2.0. The sensorgrams were corrected by double subtraction of the corresponding signals measured for the in-line control blank channel and an averaged baseline determined from three buffer blank injections[31]. Kinetic parameters were determined by data fitting using a 1:1 Langmuir binding model with BIAevaluation software version 4.1 (BIAcore).

Cell Lines

The PSMA-positive LNCaP and PSMA-negative PC-3 prostate carcinoma cell lines were grown in RPMI-1640 medium (Sigma-Aldrich, cat. no. R5886) supplemented with 10% v/v fetal bovine serum (FBS). The HEK293T/17 cell line was purchased from the American Type Culture Collection (CRL-11268) and grown in Dulbecco's modified Eagle's medium in the presence of 10% v/v fetal bovine serum under a humidified 5% v/v $CO_2$ atmosphere at 37° C. HEK293T/17 cells overexpressing PSMA were generated by jetPRIME-mediated transfection (Polyplus-transfection, 114-07) using the vector pcDNA4/V5-His A (Invitrogen) carrying the nucleotide sequence for full-length human PSMA (FOLH1; NCBI Reference sequence: NM_004476.1). The PSMA-expressing clone was obtained by repeated cloning of a single cell under the selection pressure of Zeocin (25 μg/mL; InvivoGen, ant-zn-1).

Western Blotting and Immunodetection

PSMA-overexpressing cells were washed with PBS, collected by centrifugation and lysed in 50 mM Tris/HCl pH 6.8, 2% w/v SDS, 10% v/v glycerol. The total protein concentration in the cell lysate was estimated using the BCA protein assay (Pierce Biotechnology, 23228 and 23224) and 20 μg of protein per lane were loaded on a 10% SDS-PAGE gel. After electrophoresis, proteins were transferred onto a PVDF membrane (Millipore Corporation, 1PFL00010) and PSMA was detected by subsequent incubation with the GCP04 primary antibody[32] and an anti-mouse secondary antibody conjugated to horseradish peroxidase (Bio-Rad, 172-1011), followed by signal development with Luminata Forte chemiluminescence substrate (Millipore Corporation, WBLUF0500). Signals were recorded with an ImageQuant LAS 4000 imager (GE Healthcare) and processed with Adobe Photoshop software.

Immunofluorescence Microscopy

PSMA-positive and -negative cells grown on cover slides coated with gelatin (0.1% w/v) were washed twice with PBS, fixed with 4% w/v paraformaldehyde in PBS for 15 min, permeabilized by treatment with PBS containing 0.1% v/v Triton X-100 for 15 min, and incubated in the blocking solution (5% w/v non-fat dried milk/PBS) for 30 min at room temperature (RT). Cells were then incubated with 0.5 μM Anticalin in 5% w/v non-fat dried milk/PBS for 45 min at RT followed by incubation with a Strep-tag II specific monoclonal antibody StrepMAB-Immo (2 µg/mL in PBS/ 0.05% Tween-20; IBA, 2-1517) for 1 h at RT. An anti-mouse secondary antibody conjugated to Alexa Fluor 488 (5 µg/mL in PBS/0.05% Tween-20; Life Technologies, A11029) served as detection reagent and was applied for 1 h at RT. All incubation steps were interspersed by extensive washing with PBS/0.05% Tween-20. Processed slides were treated with 4',6-diamidino-2-phenylindole (DAPI; 1 µg/mL; Sigma, D9542) for 5 min, mounted in VectaShield medium (Vector Laboratories, H-1000), and imaged with a TCS SP5 confocal microscope equipped with a 63× immersion oil objective (Leica Microsystems,). Images were processed using Adobe Photoshop software.

Flow Cytometry

Cells were detached by PBS supplemented with 0.25% w/v Trypsin and 0.02% w/v EDTA, washed, centrifuged, resuspended in PBS containing 2% w/v BSA and incubated with 1 µM of purified Anticalin for 30 min at 4° C. in a total volume of 20 µL. Next, the cell suspension was incubated with the StrepMAB-Immo antibody (6.7 µg/mL) for 30 min at 4° C. in a total volume of 40 µL. Finally, cells were incubated with an anti-mouse secondary antibody conjugated to Alexa Fluor 647 (4 µg/mL; Life Technologies, A21236) for 30 min at 4° C. in a total volume of 50 µL. All incubations and interspersing washing steps were performed in PBS/2% BSA. To label dead cells, Hoechst 33258 was added to the samples immediately before flow cytometry analysis. Cells were analyzed using a LSRII flow cytometer (BD Biosciences) and data were processed using FlowJo software (FlowJo LLC). Only viable cells (negative for Hoechst staining) were analyzed.

EXAMPLE 2: PREPARATION OF PSMA VARIANTS AS TARGET PROTEINS FOR SELECTION EXPERIMENTS AND BIOCHEMICAL ASSAYS

Three different versions of the extracellular region of human PSMA (residues 44-750; UniProt ID: Q04609) were constructed and denoted rhPSMA, Avi-PSMA, and SF-PSMA. These versions differ in their respective N-termini (FIG. 1A): while rhPSMA shows the mature N-terminus, Avi-PSMA features the Avi-tag, which is recognized by BirA ligase that catalyzes the attachment of a single biotin group both in vivo and in vitro. Expression, purification and characterization of these two variants were previously described (Barinka, C. et al. [2002] J. Neurochem. 80:477-487; Tykvart, J. et al. [2012] Protein Expr. Purif. 82:106-115). SF-PSMA was specifically constructed for this study and comprises a TEV-cleavable N-terminal Strep-tag II and FLAG-tag, arranged in tandem, which can be used for purification and immobilization, respectively. This variant was expressed in Schneider S2 cells and purified to homogeneity by StrepTactin affinity chromatography (Schmidt, T. G. & Skerra, A. [2007] Nat. Protoc. 2:1528-1535), followed by size-exclusion chromatography (SEC). The final dimeric protein preparation was >98% pure and monodisperse, with an overall yield >5 mg/L of conditioned medium (FIG. 1).

The extracellular region of human PSMA comprises 10 potential N-glycosylation sites per monomer, all carrying an oligosaccharide chain in vivo. Depending on the expression host and/or tissue source, glycans can account for up to 30% of the total molecular weight of the protein (Holmes, E. H. et al. [1996] Prostate Suppl. 7:25-29; Barinka, C. et al. [2004] Protein Sci. 13:1627-1635). Our mass-spectrometric analysis indicated that the PSMA ectodomain overexpressed in insect cells carried N-linked sugars with a combined mass of approximately 9.4 kDa (i.e. 12% of the polypeptide mass; data not shown). Such a high degree of N-glycosylation could hamper the in vitro selection of binding proteins by masking/obstructing potential surface epitopes. However, it was shown that the complete removal of N-linked sugars, e.g. by PNGase F treatment or by cultivating PSMA-expressing cells in the presence of tunicamycin, leads to inactive, partially misfolded protein preparations (Barinka, C. et al. [2004] Protein Sci. 13:1627-1635; Barinka, C. et al. [2002] J. Neurochem. 80:477-487). To increase the accessible protein surface area of PSMA that may be targeted during Anticalin selection, while still maintaining its three-dimensional fold (as well as enzymatic activity), a combined treatment with α1-2,3 mannosidase and α1-6 mannosidase was thus used to only partially deglycosylate the purified SF-PSMA. This endoglycosidase processing yielded a PSMA preparation that migrated faster in SDS-PAGE, confirming the partial removal of N-linked sugars (FIG. 7). At the same time, the partially deglycosylated protein retained its NAAG-hydrolyzing activity, suggesting that the overall fold of the enzyme was preserved (not shown). Both the fully glycosylated and partially deglycosylated versions of SF-PSMA were used for the phage display panning experiments.

EXAMPLE 3: SELECTION OF PSMA-SPECIFIC ANTICALINS

A Lcn2-based random library (Gebauer, M. et al. [2013] J. Mol. Biol. 425:780-802) cloned on the vector pNGAL108 was used for phagemid display selection against PSMA (FIG. 2). In a first selection attempt, 100 nM Avi-PSMA was used as target for solution phase panning, i.e. Avi-PSMA/phagemid complexes were formed upon incubation and subsequently captured using Streptavidin or Neutravidin paramagnetic beads; after intense washing, the bead-bound phagemids were released by acidic elution with 0.1 M glycine/HCl, pH 2.2. Following four rounds of panning, six PSMA-reactive clones were identified via ELISA screening and subcloned for expression as soluble proteins. The resulting lipocalin variants were purified and their affinities and specificities for rhPSMA were tested. Surprisingly, all variants selected by this experimental setup showed strong off-target binding as witnessed by virtually identical ELISA signals from corresponding ovalbumin-coated control plates (data not shown).

Consequently, the panning procedure was modified to increase the selectivity of elution conditions for specifically formed target/phagemid complexes by the utilization of the FLAG-tagged SF-PSMA in conjunction with anti-FLAG M2 magnetic beads and competitive elution with the FLAG peptide. Additionally, the partially deglycosylated SF-PSMA (see above) was used to increase the accessibility of epitopes on the recombinant target protein. To this end, fully glycosylated and partially deglycosylated SF-PSMA were applied in a second selection campaign in two parallel panning setups. 100 nM of each SF-PSMA variant was incubated with the naive Lcn2 library and SF-PSMA/phagemid complexes were captured via the N-terminal FLAG epitope on anti-FLAG M2 magnetic beads. After intense washing, bound phagemid particles (together with the bound target protein) were competitively eluted with a 200 µg/mL solution of the FLAG peptide. Eluted phagemids were amplified in E. coli XL1-Blue cells and used for three successive panning cycles under the same conditions. After the fourth selection round, the pool of enriched phagemids was amplified and phasmid DNA was isolated. The BstXI-flanked central lipocalin gene cassette encoding the mutagenized binding site was subcloned on the expression vector pNGAL98 (Gebauer, M. & Skerra, A. [2012] Meth. Enzymol. 503:157-188) which allowed the production of soluble Anticalin in the periplasm of E. coli TG1-F−.

Individual colonies were used for micro-scale expression in a 96-well plate and crude E. coli lysates from these cultures were screened in an ELISA for Anticalins having PSMA-binding activity. To this end, MaxiSorp plates coated with glycosylated rhPSMA were used as a target, whereas ovalbumin-coated wells were used as negative control to assess non-specific binding. Bound Anticalins were detected via the C-terminal Strep-tag II. While the first phage display selection campaign, conducted with the fully glycosylated Avi-PSMA produced in insect cells, did not yield any useful Anticalin candidates, the second attempt with the two SF-PSMA preparations was clearly successful. In total, of 172 clones that were screened 39 (approximately 23%; 32 from the selection against partially-deglycosylated SF-GCPII, 7 from the selection against fully glycosylated SF-GCPII) gave rise to a positive signal in the ELISA.

Sequencing of these clones revealed 6 unique Anticalin candidates, of which two (denoted A2 (SEQ ID NOs:69 and 74) and A3 (SEQ ID NOs:1 and 44)) were selected against the partially deglycosylated target and four (G4 (SEQ ID NOs:68 and 73), G6 (SEQ ID NOs:67 and 72), H3 (SEQ ID NOs:66 and 71), and H5 (SEQ ID NOs:65 and 70)) were selected against the fully glycosylated target. These variants were individually produced in 5 L shake flask cultures and purified from the periplasmic cell fraction of E. coli via the C-terminal Strep-tag II and SEC. The average yield of these engineered lipocalins was in the range of 0.3-0.8 mg/L. Purity and oligomerization status were assayed by SDS-PAGE and analytical SEC, respectively, indicating that all selected variants were homogenous and monomeric with an apparent molecular weight of approximately 21 kDa, as expected (FIG. 3).

EXAMPLE 4: BIOCHEMICAL CHARACTERIZATION AND AFFINITY MATURATION OF ANTICALINS

Specific binding activities of selected Anticalins toward rhPSMA as well as apparent affinity constants were initially determined by ELISA in 96-well Maxisorp plates coated with the recombinant wild-type PSMA protein. Anticalins were applied in a dilution series and detected via the C-terminal Strep-tag II. Five of the six analyzed Anticalin candidates specifically recognized PSMA with apparent dissociation constants ($K_D$ values) ranging from 6 to 42 nM, for A3 and H3, respectively (FIG. 4). For comparison, binding activity towards ovalbumin, which served as a negative control, was negligible. The G4 clone was later found to bind the anti-FLAG antibody (not shown).

The most promising variant, A3, which showed highest affinity, highest signal amplitude and low non-specific binding, was chosen for an in vitro affinity maturation using error-prone PCR (see Example 1). First, the PCR was optimized with regard to the number of amplification cycles and template amount, aiming at the introduction of 3 to 6 nucleotide mutations per Anticalin gene cassette. Then, the mutated PCR fragment was subcloned via two unique and mutually non-compatible BstXI sites on the plasmid pNGAL108, which is suitable for the production of lipocalin variants in fusion with the phage minor coat protein pIII. Transformation of electrocompetent XL1-Blue cells yielded a phagemid library with a complexity of $10^8$-$10^9$ clones and phagemid particles were produced according to published procedures (Gebauer, M. et al. [2013] J. Mol. Biol. 425: 780-802).

During the panning procedure, a modified setup with higher stringency was used to select for improved PSMA affinity as well as slower dissociation. To this end, a lower target concentration of 10 nM (for the first two rounds) and 1 nM (rounds 3 and 4) of Avi-PSMA was immobilized on paramagnetic beads coated with either streptavidin (rounds 1 and 3) or neutravidin (rounds 2 and 4). In this experiment the biotin-binding reagents were systematically altered to avoid selection of cognate binders. To further increase the selection pressure and avoid rebinding of dissociated phagemids, 100 nM rhPSMA was added as competitor to the first washing solution and incubated with the beads for 30 min at room temperature. After several additional washing steps with buffer, remaining bound phagemids were eluted using 100 mM glycine/HCl, pH 2.2. These phagemids were amplified, screened in an ELISA as described above, and sequenced. In total, 12 of 92 clones screened by the ELISA exhibited significantly higher signals in comparison with the original A3 clone. Among those, DNA sequencing revealed eight new clones. These were expressed at the shake flask scale, purified and their affinities for rhPSMA were determined by ELISA (FIG. 4). The best clone, denoted A3A5, showed an apparent dissociation constant of 2.1 nM while differing from the parent A3 Anticalin by a single substitution of Val for Met at position 40 in Loop 1 (cf. FIG. 2).

To test further mutations, bacterial surface display mediated by the E. coli autotransporter EspP was applied, a technique previously developed for the affinity maturation of Anticalins (Binder, U. et al. [2010] J. Mol. Biol. 400:783-802). To this end, the central coding region for A3A5 was subjected to another error-prone PCR as described above and subcloned on a vector that allows secretion of a fusion with the β-barrel domain of EspP and insertion into the outer membrane as well as presentation on the surface of the Gram-negative bacterium. Following incubation with Avi-PSMA and washing, cells with bound target protein were stained with a streptavidin/phycoerythrin conjugate and enriched by fluorescence activated cell sorting (FACS). In this case, a long incubation step in the presence of an excess of the purified soluble A3A5 Anticalin, prior to washing and sorting, was used for competition and selection on slow dissociation. After four FACS cycles, two mutated Anticalin candidates were identified that showed clearly enhanced signals in single clone FACS analysis for PSMA binding: A3A5.1 and A3A5.7 (cf. FIG. 2).

EXAMPLE 5: REAL-TIME AFFINITY MEASUREMENTS AND ANTICALIN-MEDIATED DETECTION OF CELLULAR PSMA

To precisely determine kinetic and thermodynamic binding constants of the PSMA-specific Anticalin A3 and its variants, surface plasmon resonance (SPR) real-time analyses was performed on a BIAcore 2000 instrument. To this end, rhPSMA was chemically coupled to the carboxymethyl dextran matrix of a sensorchip using amine chemistry and a concentrations series of each Anticalin was applied. As result, the initial Anticalin A3 exhibited a $K_D$ value of 4.8 nM whereas the first mutant resulting from affinity maturation, A3A5, was two-fold improved to 2.5 nM (Table 1). These results closely match the affinities of 5.8 and 2.1 nM, respectively that were previously determined by ELISA.

Further enhanced affinities were detected by SPR for A3A5.1 and A3A5.7, with $K_D$ values of 660 and 540 μM, respectively.

TABLE 1

$k_{on}$, $k_{off}$ and $K_D$ values of the different PSMA-specific binding proteins

| Lipocalin variant | $k_{on}$ [$10^5$ M$^{-1}$·s$^{-1}$] | $k_{off}$ [$10^{-4}$ s$^{-1}$] | $K_D$ ± SE [nM] |
|---|---|---|---|
| A3 | 1.2 | 5.8 | 4.8 ± 0.010 |
| A3A5 | 0.71 | 1.7 | 2.5 ± 0.0067 |
| A3A5.1 | 2.1 | 1.4 | 0.66 ± 0.0007 |
| A3A5.7 | 2.7 | 1.4 | 0.54 ± 0.0005 |

To determine the capability of selected Anticalins to detect PSMA in its native cellular context both transfected HEK293T cells and human prostate carcinoma cell lines were employed. HEK293T stably transfected with a plasmid encoding full length wild-type PSMA were generated using jetPRIME transfection and Zeocin selection. In addition, the PSMA-positive and PSMA-negative prostate cancer cell lines LNCaP and PC-3, respectively, were employed. The presence/absence of human PSMA in these cell lines was confirmed by Western blotting using the mAb GCP04 that specifically recognizes PSMA (FIG. 5) (Barinka, C. et al. [2004] Eur. J. Biochem. 271:2782-2790). As expected, both non-transfected HEK293T cells and the PC-3 cell line were negative for PSMA, whereas PSMA-transfected HEK293T cells as well as LNCaP cells were PSMA positive, with the HEK293T/PSMA cells expressing significantly higher levels of PSMA than LNCaP (FIG. 5A).

For immunofluorescence microscopy, the different cell lines were fixed with paraformaldehyde on glass coverslips and permeabilized. Following a blocking step, cells were probed with the Anticalin A3A5, which was detected by a murine antibody (StrepMAB-Immo) recognizing the Strep-tag II and an Alexa Fluor 488-labeled anti-mouse secondary antibody. In this manner, PSMA was stained via the Anticalin both on the plasma membrane and in the cytoplasmic region of permeabilized PSMA-positive cells, but not in the case of PSMA-negative cells. Also, when wild-type Lcn2 was used instead of the Anticalin A3A5, no fluorescent staining was detected. The intensity of the signal observed with the Anticalin for the different PSMA-positive cells was proportional to the PSMA protein level as estimated by Western blotting (FIG. 5B). Finally, flow cytometric analysis was used to assess binding of the Anticalin A3A5 to human PSMA expressed on the surface of live HEK293T/PSMA and LNCaP cells. Anticalin binding was again detected via indirect staining by a sandwich of StrepMAB-Immo and a secondary antibody labeled with Alexa Fluor 647. As seen from the flow cytometry histograms (FIG. 6), staining of HEK293T/PSMA cells was stronger than for LNCaP, in line with the Western blot and immunofluorescence data. Notably, the Anticalin did not stain both PSMA-negative control cell lines (HEK293T and PC-3), thus confirming its specificity for this target.

EXAMPLE 6: COMBINATION OF SEQUENCE VARIATIONS BETWEEN A3A5, A3A5.1 AND A3A5.7

Several combinations of mutations occurring in the PSMA-specific Lcn2 variants A3A5.1 (carrying 5 new mutations) and A3A5.7 (carrying 4 new mutations) were prepared in order to investigate the relevance of the mutations that were found during affinity maturation for improved PSMA binding with the aim to create a combined Anticalin variant suitable for further protein engineering studies. A first combination, containing solely the mutations located in the loop regions of the Anticalins, was carried out by introducing the following mutations into the sequence of A3A5 (see SEQ ID NO:2): (i) a Y at position 71 as also present in A3A5.1, (ii) an N at position 74 as also present in A3A5.7, (iii) a D at position 103 as also present in A3A5.1. This triple substitution variant, termed A3A5.8, was obtained by gene synthesis, cloned and subsequently expressed (as described in Example 1). A $K_D$ value of 1.4 nM was determined in BIAcore measurements (Table 2), which was almost 2-fold improved over the A3A5 variant but did not reach the subnanomolar affinity range as found for the variants A3A5.1 and A3A5.7. A further combination variant was constructed based on A3A5.8 by replacing the E at position 147 (as in A3A5) with a K as present in A3A5.1 as well as A3A5.7 using QuikChange mutagenesis with appropriate primers, resulting in the variant A3A5.9. Although this mutation is not situated in the Anticalin loops, its location within the structurally important α-helix that packs against the β-barrel may influence the protein structure in a way to increase PSMA binding. After soluble protein production and purification, the BIAcore measurements revealed a $K_D$ value of 740 μM (Table 2), which is close to the high affinity of the variants A3A5.1 and A3A5.7 (cf. Table 1) while lacking the four amino acid exchanges at the bottom of the β-barrel which are far away from the binding site in the loop region and less likely to be involved in PSMA binding by the Anticalin.

Generally, the introduction of these combinations of amino acid substitutions showed that variants maintain their binding properties toward PMSA when loops are modified with other mutations as exemplarily shown here for the variants A3A5.8 and A3A5.9.

TABLE 2

$k_{on}$, $k_{off}$ and $K_D$ values of combinations of mutations in PSMA-specific binding proteins

| Lipocalin variant | $k_{on}$ [$10^5$ M$^{-1}$·s$^{-1}$] | $k_{off}$ [$10^{-4}$ s$^{-1}$] | $K_D$ ± SE [nM] |
|---|---|---|---|
| A3A5.8 | 1.1 | 1.5 | 1.4 ± 0.0011 |
| A3A5.9 | 2.2 | 1.6 | 0.74 ± 0.0009 |

The invention claimed is:

1. A prostate-specific membrane antigen (PSMA)-specific binding protein, wherein the PSMA-specific binding protein is a lipocalin 2 (Lcn2)-derived binding protein and binds to PSMA with a $K_D$ of 10 nM or lower, and further wherein the PSMA-specific binding protein comprises or consists of an amino acid sequence selected from the group consisting of the amino acid sequences of SEQ ID NOs:1 to 6.

2. The PSMA-specific binding protein of claim 1, wherein the PSMA-specific binding protein comprises or consists of an amino acid sequence selected from the group consisting of the amino acid sequences represented in SEQ ID NO:3 and SEQ ID NO:4.

3. A protein conjugate comprising the PSMA-specific binding protein of claim 1.

4. A pharmaceutical or diagnostic composition comprising at least one of
   (i) a PSMA-specific binding protein of claim 1; or
   (ii) a PSMA-specific binding protein produced by culturing a host cell transformed with a vector encoding a nucleic acid molecule encoding the PSMA-specific binding protein of claim 1 under suitable conditions and isolating the PSMA-specific binding protein produced.

5. A composition of claim 4, wherein the PSMA-specific binding protein is a protein conjugate comprising the PSMA-specific binding protein.

6. A method for the production of a PSMA-specific binding protein, the method comprising culturing a host cell transformed with a vector comprising a nucleic acid molecule encoding the PSMA-specific binding protein of claim 1 under suitable conditions and isolating the PSMA-specific binding protein produced.

7. A method for therapy and/or diagnosis of tumors and Crohn's disease, comprising administration of a composition of claim 4, wherein the method for therapy comprises administration of a therapeutically effective amount of a pharmaceutical composition of claim 4, and the method for diagnosis comprises administration of a composition of claim 4 and measuring binding to PSMA.

8. The method of claim 7, wherein the PSMA-specific binding protein is a protein conjugate comprising the PSMA-specific binding protein.

9. The method of claim 7, wherein the method for diagnosis further comprises imaging.

10. A method for diagnosis of schizophrenia, comprising administration of a composition of claim 4, wherein the method for diagnosis comprises administration of a composition of claim 4 and measuring binding to PSMA.

11. The method of claim 10, wherein the method for diagnosis further comprises imaging.

* * * * *

SEQUENCE LISTING

<160> NUMBER OF SEQ ID NOS: 74

<210> SEQ ID NO 1
<211> LENGTH: 178
<212> TYPE: PRT

```
<213> ORGANISM: Artificial Sequence
<220> FEATURE:
<223> OTHER INFORMATION: Synthetic PSMA-specific binding protein A3

<400> SEQUENCE: 1

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Leu Ala Gly Asn Met Ile Leu Arg Glu Asp Lys Asp Pro
            35                  40                  45

Tyr Lys Met Ser Ala Thr Ile Tyr Glu Leu Lys Glu Asp Lys Ser Tyr
    50                  55                  60

Asn Val Thr Asn Val Arg Phe Tyr Leu Lys Lys Cys Tyr Tyr Thr Ile
65                  70                  75                  80

Ala Thr Phe Val Pro Gly Ser Gln Pro Gly Glu Phe Thr Leu Gly Thr
                85                  90                  95

Ile Lys Ser Gly Pro Gly Lys Thr Ser Gly Leu Val Arg Val Val Ser
                100                 105                 110

Thr Asn Tyr Asn Gln His Ala Met Val Phe Phe Lys Glu Val Gln Gln
            115                 120                 125

Asn Arg Glu Trp Phe Ile Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 2
<211> LENGTH: 178
<212> TYPE: PRT
<213> ORGANISM: Artificial Sequence
<220> FEATURE:
<223> OTHER INFORMATION: Synthetic PSMA-specific binding protein A3A5

<400> SEQUENCE: 2

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Leu Ala Gly Asn Val Ile Leu Arg Glu Asp Lys Asp Pro
            35                  40                  45

Tyr Lys Met Ser Ala Thr Ile Tyr Glu Leu Lys Glu Asp Lys Ser Tyr
    50                  55                  60

Asn Val Thr Asn Val Arg Phe Tyr Leu Lys Lys Cys Tyr Tyr Thr Ile
65                  70                  75                  80

Ala Thr Phe Val Pro Gly Ser Gln Pro Gly Glu Phe Thr Leu Gly Thr
                85                  90                  95

Ile Lys Ser Gly Pro Gly Lys Thr Ser Gly Leu Val Arg Val Val Ser
                100                 105                 110

Thr Asn Tyr Asn Gln His Ala Met Val Phe Phe Lys Glu Val Gln Gln
            115                 120                 125

Asn Arg Glu Trp Phe Ile Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
```

```
                145                 150                 155                 160
Leu Pro Glu Asn His Ile Val Phe Pro Val Pro Ile Asp Gln Cys Ile
                165                 170                 175

Asp Gly

<210> SEQ ID NO 3
<211> LENGTH: 178
<212> TYPE: PRT
<213> ORGANISM: Artificial Sequence
<220> FEATURE:
<223> OTHER INFORMATION: Synthetic PSMA-specific binding protein A3A5-1

<400> SEQUENCE: 3

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Leu Ala Gly Asn Val Ile Leu Arg Glu Asp Lys Asp Pro
            35                  40                  45

Tyr Lys Met Ser Ala Thr Ile Tyr Glu Leu Asn Glu Asp Lys Ser Tyr
    50                  55                  60

Asn Val Thr Asn Val Arg Tyr Tyr Leu Lys Lys Cys Tyr Tyr Thr Ile
65                  70                  75                  80

Ala Thr Phe Val Pro Gly Ser Gln Pro Gly Glu Tyr Thr Leu Gly Thr
                85                  90                  95

Ile Lys Ser Gly Pro Gly Asp Thr Ser Gly Leu Val Arg Val Val Ser
            100                 105                 110

Thr Asn Tyr Asn Gln His Ala Met Val Phe Phe Lys Glu Val Gln Gln
        115                 120                 125

Asn Arg Glu Trp Phe Ile Ile Thr Leu Tyr Gly Arg Thr Lys Glu Leu
    130                 135                 140

Thr Ser Lys Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 4
<211> LENGTH: 178
<212> TYPE: PRT
<213> ORGANISM: Artificial Sequence
<220> FEATURE:
<223> OTHER INFORMATION: Synthetic PSMA-specific binding protein A3A5-7

<400> SEQUENCE: 4

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Leu Ala Gly Asn Val Ile Leu Arg Glu Asp Lys Asp Pro
            35                  40                  45

Tyr Lys Met Ser Ala Thr Ile Tyr Glu Leu Lys Glu Asp Lys Ser Tyr
    50                  55                  60

Asn Val Thr Asn Val Arg Phe Tyr Leu Asn Lys Cys Tyr Tyr Thr Ile
65                  70                  75                  80

Ala Thr Phe Val Pro Gly Ser Arg Pro Gly Glu Phe Thr Leu Gly Thr
                85                  90                  95
```

```
Ile Lys Ser Gly Pro Gly Lys Thr Ser Gly Leu Val Arg Val Val Ser
            100                 105                 110

Thr Asn Tyr Ser Gln His Ala Met Val Phe Lys Glu Val Gln Gln
            115                 120                 125

Asn Arg Glu Trp Phe Ile Ile Thr Leu Tyr Gly Arg Thr Lys Glu Leu
130                 135                 140

Thr Ser Lys Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 5
<211> LENGTH: 178
<212> TYPE: PRT
<213> ORGANISM: Artificial Sequence
<220> FEATURE:
<223> OTHER INFORMATION: Synthetic PSMA-specific binding protein A3A5-8

<400> SEQUENCE: 5

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Val Ile Leu Arg Glu Asp Lys Asp Pro
        35                  40                  45

Tyr Lys Met Ser Ala Thr Ile Tyr Glu Leu Lys Glu Asp Lys Ser Tyr
50                  55                  60

Asn Val Thr Asn Val Arg Tyr Tyr Leu Asn Lys Cys Tyr Tyr Thr Ile
65                  70                  75                  80

Ala Thr Phe Val Pro Gly Ser Gln Pro Gly Glu Phe Thr Leu Gly Thr
                85                  90                  95

Ile Lys Ser Gly Pro Gly Asp Thr Ser Gly Leu Val Arg Val Val Ser
            100                 105                 110

Thr Asn Tyr Asn Gln His Ala Met Val Phe Lys Glu Val Gln Gln
            115                 120                 125

Asn Arg Glu Trp Phe Ile Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 6
<211> LENGTH: 178
<212> TYPE: PRT
<213> ORGANISM: Artificial Sequence
<220> FEATURE:
<223> OTHER INFORMATION: Synthetic PSMA-specific binding protein A3A5-9

<400> SEQUENCE: 6

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30
```

```
Val Val Gly Leu Ala Gly Asn Val Ile Leu Arg Glu Asp Lys Asp Pro
             35                  40                  45

Tyr Lys Met Ser Ala Thr Ile Tyr Glu Leu Lys Glu Asp Lys Ser Tyr
 50                  55                  60

Asn Val Thr Asn Val Arg Tyr Tyr Leu Asn Lys Cys Tyr Tyr Thr Ile
 65                  70                  75                  80

Ala Thr Phe Val Pro Gly Ser Gln Pro Gly Glu Phe Thr Leu Gly Thr
                 85                  90                  95

Ile Lys Ser Gly Pro Gly Asp Thr Ser Gly Leu Val Arg Val Val Ser
                100                 105                 110

Thr Asn Tyr Asn Gln His Ala Met Val Phe Phe Lys Glu Val Gln Gln
             115                 120                 125

Asn Arg Glu Trp Phe Ile Ile Thr Leu Tyr Gly Arg Thr Lys Glu Leu
 130                 135                 140

Thr Ser Lys Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 7
<211> LENGTH: 178
<212> TYPE: PRT
<213> ORGANISM: Artificial Sequence
<220> FEATURE:
<223> OTHER INFORMATION: Synthetic wtLcn2

<400> SEQUENCE: 7

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe Gln Gly Lys Trp Tyr
                 20                  25                  30

Val Val Gly Leu Ala Gly Asn Ala Ile Leu Arg Glu Asp Lys Asp Pro
             35                  40                  45

Gln Lys Met Tyr Ala Thr Ile Tyr Glu Leu Lys Glu Asp Lys Ser Tyr
 50                  55                  60

Asn Val Thr Ser Val Leu Phe Arg Lys Lys Lys Cys Asp Tyr Trp Ile
 65                  70                  75                  80

Arg Thr Phe Val Pro Gly Cys Gln Pro Gly Glu Phe Thr Leu Gly Asn
                 85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
             115                 120                 125

Asn Arg Glu Tyr Phe Lys Ile Thr Leu Tyr Gly Arg Thr Lys Glu Leu
 130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 8
<211> LENGTH: 27
<212> TYPE: PRT
<213> ORGANISM: Artificial Sequence
```

```
<220> FEATURE:
<223> OTHER INFORMATION: Synthetic PSMA-specific binding protein Frame
      1 x1

<400> SEQUENCE: 8

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe
            20                  25

<210> SEQ ID NO 9
<211> LENGTH: 9
<212> TYPE: PRT
<213> ORGANISM: Artificial Sequence
<220> FEATURE:
<223> OTHER INFORMATION: Synthetic PSMA-specific binding protein Frame
      1 x2

<400> SEQUENCE: 9

Gly Lys Trp Tyr Val Val Gly Leu Ala
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic PSMA-specific binding protein Frame
      2 x3

<400> SEQUENCE: 10

Ala Thr Ile Tyr Glu Leu
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic PSMA-specific binding protein Frame
      2 x4

<400> SEQUENCE: 11

Glu Asp Lys Ser Tyr Asn Val Thr
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic PSMA-specific binding protein Frame
      3 x8

<400> SEQUENCE: 12

Thr Phe Val Pro Gly
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic PSMA-specific binding protein Frame
      4 x11

<400> SEQUENCE: 13
```

Leu Val Arg Val Val Ser Thr Asn Tyr
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic PSMA-specific binding protein Frame
      4 x12

<400> SEQUENCE: 14

Gln His Ala Met Val Phe Phe Lys
1               5

<210> SEQ ID NO 15
<211> LENGTH: 12
<212> TYPE: PRT
<213> ORGANISM: Artificial Sequence
<220> FEATURE:
<223> OTHER INFORMATION: Synthetic PSMA-specific binding protein Frame
      5 x14

<400> SEQUENCE: 15

Ile Thr Leu Tyr Gly Arg Thr Lys Glu Leu Thr Ser
1               5                   10

<210> SEQ ID NO 16
<211> LENGTH: 31
<212> TYPE: PRT
<213> ORGANISM: Artificial Sequence
<220> FEATURE:
<223> OTHER INFORMATION: Synthetic PSMA-specific binding protein Frame
      5 x15

<400> SEQUENCE: 16

Leu Lys Glu Asn Phe Ile Arg Phe Ser Lys Ser Leu Gly Leu Pro Glu
1               5                   10                  15

Asn His Ile Val Phe Pro Val Pro Ile Asp Gln Cys Ile Asp Gly
            20                  25                  30

<210> SEQ ID NO 17
<211> LENGTH: 8
<212> TYPE: PRT
<213> ORGANISM: Artificial Sequence
<220> FEATURE:
<223> OTHER INFORMATION: Synthetic PSMA-specific binding protein Loop
      1 y2

<400> SEQUENCE: 17

Ile Leu Arg Glu Asp Lys Asp Pro
1               5

<210> SEQ ID NO 18
<211> LENGTH: 4
<212> TYPE: PRT
<213> ORGANISM: Artificial Sequence
<220> FEATURE:
<223> OTHER INFORMATION: Synthetic PSMA-specific binding protein Loop
      4 y10

<400> SEQUENCE: 18

Gln Asn Arg Glu
1

<210> SEQ ID NO 19
<211> LENGTH: 14

```
<212> TYPE: PRT
<213> ORGANISM: Artificial Sequence
<220> FEATURE:
<223> OTHER INFORMATION: Synthetic PSMA-specific binding protein Loop 1

<400> SEQUENCE: 19

Gly Asn Val Ile Leu Arg Glu Asp Lys Asp Pro Tyr Lys Met
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Synthetic PSMA-specific binding protein Loop 1

<400> SEQUENCE: 20

Gly Asn Met Ile Leu Arg Glu Asp Lys Asp Pro Tyr Lys Met
1               5                   10

<210> SEQ ID NO 21
<211> LENGTH: 7
<212> TYPE: PRT
<213> ORGANISM: Artificial Sequence
<220> FEATURE:
<223> OTHER INFORMATION: Synthetic PSMA-specific binding protein Loop 2

<400> SEQUENCE: 21

Arg Phe Tyr Leu Asn Lys Cys
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic PSMA-specific binding protein Loop 2

<400> SEQUENCE: 22

Arg Phe Tyr Leu Lys Lys Cys
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic PSMA-specific binding protein Loop 2

<400> SEQUENCE: 23

Arg Tyr Tyr Leu Asn Lys Cys
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic PSMA-specific binding protein Loop 2

<400> SEQUENCE: 24

Arg Tyr Tyr Leu Lys Lys Cys
1               5

<210> SEQ ID NO 25
<211> LENGTH: 11
<212> TYPE: PRT
```

```
<213> ORGANISM: Artificial Sequence
<220> FEATURE:
<223> OTHER INFORMATION: Synthetic PSMA-specific binding protein Loop 3

<400> SEQUENCE: 25

Gly Thr Ile Lys Ser Gly Pro Gly Lys Thr Ser
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Synthetic PSMA-specific binding protein Loop 3

<400> SEQUENCE: 26

Gly Thr Ile Lys Ser Gly Pro Gly Asp Thr Ser
1               5                   10

<210> SEQ ID NO 27
<211> LENGTH: 8
<212> TYPE: PRT
<213> ORGANISM: Artificial Sequence
<220> FEATURE:
<223> OTHER INFORMATION: Synthetic PSMA-specific binding protein Loop 4

<400> SEQUENCE: 27

Glu Val Gln Gln Asn Arg Glu Trp
1               5

<210> SEQ ID NO 28
<211> LENGTH: 37
<212> TYPE: PRT
<213> ORGANISM: Artificial Sequence
<220> FEATURE:
<223> OTHER INFORMATION: Synthetic PSMA-specific binding protein Frame 1

<400> SEQUENCE: 28

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala
        35

<210> SEQ ID NO 29
<211> LENGTH: 37
<212> TYPE: PRT
<213> ORGANISM: Artificial Sequence
<220> FEATURE:
<223> OTHER INFORMATION: Synthetic PSMA-specific binding protein Frame 1

<400> SEQUENCE: 29

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala
        35

<210> SEQ ID NO 30
<211> LENGTH: 18
<212> TYPE: PRT
<213> ORGANISM: Artificial Sequence
<220> FEATURE:
```

<223> OTHER INFORMATION: Synthetic PSMA-specific binding protein Frame 2

<400> SEQUENCE: 30

Ser Ala Thr Ile Tyr Glu Leu Lys Glu Asp Lys Ser Tyr Asn Val Thr
1               5                   10                  15

Asn Val

<210> SEQ ID NO 31
<211> LENGTH: 18
<212> TYPE: PRT
<213> ORGANISM: Artificial Sequence
<220> FEATURE:
<223> OTHER INFORMATION: Synthetic PSMA-specific binding protein Frame 2

<400> SEQUENCE: 31

Ser Ala Thr Ile Tyr Glu Leu Asn Glu Asp Lys Ser Tyr Asn Val Thr
1               5                   10                  15

Asn Val

<210> SEQ ID NO 32
<211> LENGTH: 18
<212> TYPE: PRT
<213> ORGANISM: Artificial Sequence
<220> FEATURE:
<223> OTHER INFORMATION: Synthetic PSMA-specific binding protein Frame 3

<400> SEQUENCE: 32

Tyr Tyr Thr Ile Ala Thr Phe Val Pro Gly Ser Arg Pro Gly Glu Phe
1               5                   10                  15

Thr Leu

<210> SEQ ID NO 33
<211> LENGTH: 18
<212> TYPE: PRT
<213> ORGANISM: Artificial Sequence
<220> FEATURE:
<223> OTHER INFORMATION: Synthetic PSMA-specific binding protein Frame 3

<400> SEQUENCE: 33

Tyr Tyr Thr Ile Ala Thr Phe Val Pro Gly Ser Gln Pro Gly Glu Phe
1               5                   10                  15

Thr Leu

<210> SEQ ID NO 34
<211> LENGTH: 18
<212> TYPE: PRT
<213> ORGANISM: Artificial Sequence
<220> FEATURE:
<223> OTHER INFORMATION: Synthetic PSMA-specific binding protein Frame 3

<400> SEQUENCE: 34

Tyr Tyr Thr Ile Ala Thr Phe Val Pro Gly Ser Gln Pro Gly Glu Tyr
1               5                   10                  15

Thr Leu

<210> SEQ ID NO 35
<211> LENGTH: 18
<212> TYPE: PRT
<213> ORGANISM: Artificial Sequence
<220> FEATURE:
<223> OTHER INFORMATION: Synthetic PSMA-specific binding protein Frame 3

<400> SEQUENCE: 35

```
Tyr Tyr Thr Ile Ala Thr Phe Val Pro Gly Ser Arg Pro Gly Glu Tyr
1               5                   10                  15

Thr Leu

<210> SEQ ID NO 36
<211> LENGTH: 18
<212> TYPE: PRT
<213> ORGANISM: Artificial Sequence
<220> FEATURE:
<223> OTHER INFORMATION: Synthetic PSMA-specific binding protein Frame 3

<400> SEQUENCE: 36

Tyr Tyr Thr Ile Ala Thr Phe Val Pro Gly Cys Arg Pro Gly Glu Phe
1               5                   10                  15

Thr Leu

<210> SEQ ID NO 37
<211> LENGTH: 18
<212> TYPE: PRT
<213> ORGANISM: Artificial Sequence
<220> FEATURE:
<223> OTHER INFORMATION: Synthetic PSMA-specific binding protein Frame 3

<400> SEQUENCE: 37

Tyr Tyr Thr Ile Ala Thr Phe Val Pro Gly Cys Gln Pro Gly Glu Phe
1               5                   10                  15

Thr Leu

<210> SEQ ID NO 38
<211> LENGTH: 18
<212> TYPE: PRT
<213> ORGANISM: Artificial Sequence
<220> FEATURE:
<223> OTHER INFORMATION: Synthetic PSMA-specific binding protein Frame 3

<400> SEQUENCE: 38

Tyr Tyr Thr Ile Ala Thr Phe Val Pro Gly Cys Gln Pro Gly Glu Tyr
1               5                   10                  15

Thr Leu

<210> SEQ ID NO 39
<211> LENGTH: 18
<212> TYPE: PRT
<213> ORGANISM: Artificial Sequence
<220> FEATURE:
<223> OTHER INFORMATION: Synthetic PSMA-specific binding protein Frame 3

<400> SEQUENCE: 39

Tyr Tyr Thr Ile Ala Thr Phe Val Pro Gly Cys Arg Pro Gly Glu Tyr
1               5                   10                  15

Thr Leu

<210> SEQ ID NO 40
<211> LENGTH: 19
<212> TYPE: PRT
<213> ORGANISM: Artificial Sequence
<220> FEATURE:
<223> OTHER INFORMATION: Synthetic PSMA-specific binding protein Frame 4

<400> SEQUENCE: 40

Gly Leu Val Arg Val Val Ser Thr Asn Tyr Ser Gln His Ala Met Val
1               5                   10                  15

Phe Phe Lys
```

<210> SEQ ID NO 41
<211> LENGTH: 19
<212> TYPE: PRT
<213> ORGANISM: Artificial Sequence
<220> FEATURE:
<223> OTHER INFORMATION: Synthetic PSMA-specific binding protein Frame 4

<400> SEQUENCE: 41

Gly Leu Val Arg Val Val Ser Thr Asn Tyr Asn Gln His Ala Met Val
1               5                   10                  15

Phe Phe Lys

<210> SEQ ID NO 42
<211> LENGTH: 46
<212> TYPE: PRT
<213> ORGANISM: Artificial Sequence
<220> FEATURE:
<223> OTHER INFORMATION: Synthetic PSMA-specific binding protein Frame 5

<400> SEQUENCE: 42

Phe Ile Ile Thr Leu Tyr Gly Arg Thr Lys Glu Leu Thr Ser Lys Leu
1               5                   10                  15

Lys Glu Asn Phe Ile Arg Phe Ser Lys Ser Leu Gly Leu Pro Glu Asn
            20                  25                  30

His Ile Val Phe Pro Val Pro Ile Asp Gln Cys Ile Asp Gly
        35                  40                  45

<210> SEQ ID NO 43
<211> LENGTH: 46
<212> TYPE: PRT
<213> ORGANISM: Artificial Sequence
<220> FEATURE:
<223> OTHER INFORMATION: Synthetic PSMA-specific binding protein Frame 5

<400> SEQUENCE: 43

Phe Ile Ile Thr Leu Tyr Gly Arg Thr Lys Glu Leu Thr Ser Glu Leu
1               5                   10                  15

Lys Glu Asn Phe Ile Arg Phe Ser Lys Ser Leu Gly Leu Pro Glu Asn
            20                  25                  30

His Ile Val Phe Pro Val Pro Ile Asp Gln Cys Ile Asp Gly
        35                  40                  45

<210> SEQ ID NO 44
<211> LENGTH: 534
<212> TYPE: DNA
<213> ORGANISM: Artificial Sequence
<220> FEATURE:
<221> NAME/KEY: source
<222> LOCATION: 1..534
<223> OTHER INFORMATION: /mol_type="unassigned DNA"
     /note= "Synthetic PSMA-specific binding protein A3"
     /organism="Artificial Sequence"

<400> SEQUENCE: 44
caggactcca cctcagacct gatcccagcc ccacctctga gcaaggtccc tctgcagcag      60
aacttccagg acaaccaatt ccatgggaaa tggtatgtcg tgggcctggc cggaaatatg     120
atcctgcgtg aggataagga tccgtacaaa atgagcgcga ccatttacga gttgaaagaa     180
gataaatcat ataacgtcac caatgtgcgt ttttacctga gaaatgcta ctacaccatt      240 gcaacctttg tgccggggag ccagccgggc gagtttactt taggcaccat taaaagtgga     300
ccgggcaaaa catcaggatt ggtccgcgtc gtgagcacca actacaacca gcatgccatg     360
gtgttcttca aggaggtgca acagaaccgc gagtggttta tcatcacact gtacgggcgc      420
acgaaagaac tgacaagcga gctgaaggaa aattttatcc gcttttccaa atctctgggc      480
ctccctgaaa accacatcgt cttccctgtc ccaatcgacc agtgtatcga cggc            534

<210> SEQ ID NO 45
<211> LENGTH: 534
<212> TYPE: DNA
<213> ORGANISM: Artificial Sequence
<220> FEATURE:
<221> NAME/KEY: source
<222> LOCATION: 1..534
<223> OTHER INFORMATION: /mol_type="unassigned DNA"
     /note="Synthetic PSMA-specific binding protein A3A5"
     /organism="Artificial Sequence"

<400> SEQUENCE: 45
caggactcca cctcagacct gatcccagcc ccacctctga gcaaggtccc tctgcagcag      60
aacttccagg acaaccaatt ccatgggaaa tggtatgtcg tgggcctggc cggaaatgtg      120
atcctgcgtg aggataagga tccgtacaaa atgagcgcga ccatttacga gttgaaagaa      180
gataaatcat ataacgtcac caatgtgcgt ttttacctga gaaatgcta ctacaccatt      240 gcaacctttg tgccggggag ccagccgggc gagtttactt taggcaccat taaaagtgga      300
ccgggcaaaa catcaggatt ggtccgcgtc gtgagcacca actacaacca gcatgccatg      360
gtgttcttca aggaggtgca acagaaccgc gagtggttta tcatcacact gtacgggcgc      420
acgaaagaac tgacaagcga gctgaaggaa aattttatcc gcttttccaa atctctgggc      480
ctccctgaaa accacatcgt cttccctgtc ccaatcgacc agtgtatcga cggc            534

<210> SEQ ID NO 46
<211> LENGTH: 534
<212> TYPE: DNA
<213> ORGANISM: Artificial Sequence
<220> FEATURE:
<221> NAME/KEY: source
<222> LOCATION: 1..534
<223> OTHER INFORMATION: /mol_type="unassigned DNA"
     /note="Synthetic PSMA-specific binding protein A3A5-1"
     /organism="Artificial Sequence"

<400> SEQUENCE: 46
caggactcca cctcagacct gatcccagcc ccacctctga gcaaggtccc tctgcagcag      60
aacttccagg acaaccaatt ccatgggaaa tggtatgtcg tgggcctggc cggaaatgtg      120
atcctacgtg aggataagga tccgtacaaa atgagcgcga ccatttacga gttgaatgaa      180
gataaatcat ataacgtcac caatgtgcgt tattacctga gaaatgcta ctacaccatt      240 gcaacctttg tgccggggag ccagccgggc gagtatactt taggcaccat taaaagtgga      300
ccgggcgata catcaggatt ggtccgcgtc gtgagcacca attacaacca gcatgccatg      360
gtgttcttca aggaggtgca acagaaccgc gagtggttta tcatcacact gtacgggcgc      420
acgaaagaac tgacaagcaa gctgaaggaa aattttatcc gcttttccaa atctctgggc      480
ctccctgaaa accacatcgt cttccctgtc ccaatcgacc agtgtatcga cggc            534

<210> SEQ ID NO 47
<211> LENGTH: 534
<212> TYPE: DNA
<213> ORGANISM: Artificial Sequence
<220> FEATURE:
<221> NAME/KEY: source
<222> LOCATION: 1..534

```
<223> OTHER INFORMATION: /mol_type="unassigned DNA"
      /note="Synthetic PSMA-specific binding protein A3A5-7"
      /organism="Artificial Sequence"

<400> SEQUENCE: 47
caggactcca cctcagacct gatcccagcc ccacctctga gcaaggtccc tctgcagcag      60
aacttccagg acaaccaatt ccatgggaaa tggtatgtcg tgggcctggc cggaaatgtg     120
atcctgcgtg aggacaagga tccgtacaaa atgagcgcga ccatttacga gttgaaagaa     180
gataaatcat ataacgtcac caatgtgcgt ttttacctga taaatgcta ctacaccatt      240 gcaacctttg tgccggggag ccggccgggc gagtttactt taggcaccat taaaagtgga     300
ccgggcaaaa catcaggatt ggtccgcgtc gtgagcacca actacagcca gcatgccatg     360
gtgttcttca aggaagtgca acagaaccgc gagtggttta tcatcacact gtacgggcgc     420
acgaaagaac tgacaagcaa gctgaaggaa aattttatcc gcttttccaa atctctgggc     480
ctccctgaaa accacatcgt cttccctgtc ccaatcgacc agtgtatcga cggc           534

<210> SEQ ID NO 48
<211> LENGTH: 534
<212> TYPE: DNA
<213> ORGANISM: Artificial Sequence
<220> FEATURE:
<221> NAME/KEY: source
<222> LOCATION: 1..534
<223> OTHER INFORMATION: /mol_type="unassigned DNA"
      /note="Synthetic PSMA-specific binding protein A3A5-8"
      /organism="Artificial Sequence"

<400> SEQUENCE: 48
caggactcca cctcagacct gatcccagcc ccacctctga gcaaggtccc tctgcagcag      60
aacttccagg acaaccaatt ccatgggaaa tggtatgtcg tgggcctggc cggaaatgtg     120
atcctgcgtg aggataagga tccgtacaaa atgagcgcga ccatttacga gctcaaagaa     180
gataaatcat ataacgtcac caatgtgcgt tattacctga caaatgcta ctacaccatt      240 gcaacctttg tgccggggag ccagccgggc gaattcactt taggtaccat taaaagtgga     300
cccggggata catcaggatt ggtccgcgtc gtgagcacca actacaacca gcatgccatg     360
gtgttcttca aggaggtgca acagaaccgc gagtggttta tcatcacact gtacgggcgc     420
acgaaagaac tgacaagcga gctgaaggaa aattttatcc gcttttccaa atctctgggc     480
ctccctgaaa accacatcgt cttccctgtc ccaatcgacc agtgtatcga cggc           534

<210> SEQ ID NO 49
<211> LENGTH: 534
<212> TYPE: DNA
<213> ORGANISM: Artificial Sequence
<220> FEATURE:
<221> NAME/KEY: source
<222> LOCATION: 1..534
<223> OTHER INFORMATION: /mol_type="unassigned DNA"
      /note="Synthetic PSMA-specific binding protein A3A5-9"
      /organism="Artificial Sequence"

<400> SEQUENCE: 49
caggactcca cctcagacct gatcccagcc ccacctctga gcaaggtccc tctgcagcag      60
aacttccagg acaaccaatt ccatgggaaa tggtatgtcg tgggcctggc cggaaatgtg     120
atcctgcgtg aggataagga tccgtacaaa atgagcgcga ccatttacga gctcaaagaa     180
gataaatcat ataacgtcac caatgtgcgt tattacctga caaatgcta ctacaccatt      240 gcaacctttg tgccggggag ccagccgggc gaattcactt taggtaccat taaaagtgga     300
```

```
cccggggata catcaggatt ggtccgcgtc gtgagcacca actacaacca gcatgccatg    360
gtgttcttca aggaggtgca acagaaccgc gagtggttta tcatcacact gtacgggcgc    420
acgaaagaac tgacaagcaa gctgaaggaa aattttatcc gcttttccaa atctctgggc    480
ctccctgaaa accacatcgt cttccctgtc ccaatcgacc agtgtatcga cggc          534
```

```
<210> SEQ ID NO 50
<211> LENGTH: 32
<212> TYPE: PRT
<213> ORGANISM: Artificial Sequence
<220> FEATURE:
<223> OTHER INFORMATION: Synthetic peptide Avi-tag

<400> SEQUENCE: 50

Arg Ser Gly Leu Asn Asp Ile Phe Glu Ala Gln Lys Ile Glu Trp His
1               5                   10                  15

Glu Gly Ser Gly Ser Gly Ser Glu Asn Leu Tyr Phe Gln Gly Arg Ser
            20                  25                  30

<210> SEQ ID NO 51
<211> LENGTH: 27
<212> TYPE: PRT
<213> ORGANISM: Artificial Sequence
<220> FEATURE:
<223> OTHER INFORMATION: Synthetic peptide StrepII-Flag-tag

<400> SEQUENCE: 51

Arg Ser Trp Ser His Pro Gln Phe Glu Lys Asp Tyr Lys Asp Asp Asp
1               5                   10                  15

Asp Lys Glu Asn Leu Tyr Phe Gln Gly Arg Ser
            20                  25

<210> SEQ ID NO 52
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="Anticalin amplification primer 1"
      /organism="Artificial Sequence"

<400> SEQUENCE: 52
agacagctat cgcgattgca                                                 20

<210> SEQ ID NO 53
<211> LENGTH: 17
<212> TYPE: DNA
<213> ORGANISM: Artificial Sequence
<220> FEATURE:
<221> NAME/KEY: source
<222> LOCATION: 1..17
<223> OTHER INFORMATION: /mol_type="unassigned DNA"
      /note="Anticalin amplification primer 2"
      /organism="Artificial Sequence"

<400> SEQUENCE: 53
cgcagtagcg gtaaacg                                                    17

<210> SEQ ID NO 54
<211> LENGTH: 21
<212> TYPE: DNA
<213> ORGANISM: Artificial Sequence
<220> FEATURE:
```

```
<221> NAME/KEY: source
<222> LOCATION: 1..21
<223> OTHER INFORMATION: /mol_type="unassigned DNA"
      /note="error-prone PCR primer BstXI-for"
      /organism="Artificial Sequence"

<400> SEQUENCE: 54
caggacaacc aattccatgg g                                                 21

<210> SEQ ID NO 55
<211> LENGTH: 18
<212> TYPE: DNA
<213> ORGANISM: Artificial Sequence
<220> FEATURE:
<221> NAME/KEY: source
<222> LOCATION: 1..18
<223> OTHER INFORMATION: /mol_type="unassigned DNA"
      /note="error-prone PCR primer BstXI-rev"
      /organism="Artificial Sequence"

<400> SEQUENCE: 55
ggaggcccag agatttgg                                                     18

<210> SEQ ID NO 56
<211> LENGTH: 21
<212> TYPE: PRT
<213> ORGANISM: Artificial Sequence
<220> FEATURE:
<223> OTHER INFORMATION: Synthetic PSMA-specific binding protein Frame
      1 N-terminal deletion fragment

<400> SEQUENCE: 56

Leu Ile Pro Ala Pro Pro Leu Ser Lys Val Pro Leu Gln Gln Asn Phe
1               5                   10                  15

Gln Asp Asn Gln Phe
            20

<210> SEQ ID NO 57
<211> LENGTH: 22
<212> TYPE: PRT
<213> ORGANISM: Artificial Sequence
<220> FEATURE:
<223> OTHER INFORMATION: Synthetic PSMA-specific binding protein Frame
      1 N-terminal deletion fragment

<400> SEQUENCE: 57

Asp Leu Ile Pro Ala Pro Pro Leu Ser Lys Val Pro Leu Gln Gln Asn
1               5                   10                  15

Phe Gln Asp Asn Gln Phe
            20

<210> SEQ ID NO 58
<211> LENGTH: 23
<212> TYPE: PRT
<213> ORGANISM: Artificial Sequence
<220> FEATURE:
<223> OTHER INFORMATION: Synthetic PSMA-specific binding protein Frame
      1 N-terminal deletion fragment

<400> SEQUENCE: 58

Ser Asp Leu Ile Pro Ala Pro Pro Leu Ser Lys Val Pro Leu Gln Gln
1               5                   10                  15

Asn Phe Gln Asp Asn Gln Phe
            20

<210> SEQ ID NO 59
```

```
<211> LENGTH: 24
<212> TYPE: PRT
<213> ORGANISM: Artificial Sequence
<220> FEATURE:
<223> OTHER INFORMATION: Synthetic PSMA-specific binding protein Frame
      1 N-terminal deletion fragment

<400> SEQUENCE: 59

Thr Ser Asp Leu Ile Pro Ala Pro Pro Leu Ser Lys Val Pro Leu Gln
1               5                   10                  15

Gln Asn Phe Gln Asp Asn Gln Phe
            20

<210> SEQ ID NO 60
<211> LENGTH: 25
<212> TYPE: PRT
<213> ORGANISM: Artificial Sequence
<220> FEATURE:
<223> OTHER INFORMATION: Synthetic PSMA-specific binding protein Frame
      1 N-terminal deletion fragment

<400> SEQUENCE: 60

Ser Thr Ser Asp Leu Ile Pro Ala Pro Pro Leu Ser Lys Val Pro Leu
1               5                   10                  15

Gln Gln Asn Phe Gln Asp Asn Gln Phe
            20                  25

<210> SEQ ID NO 61
<211> LENGTH: 26
<212> TYPE: PRT
<213> ORGANISM: Artificial Sequence
<220> FEATURE:
<223> OTHER INFORMATION: Synthetic PSMA-specific binding protein Frame
      1 N-terminal deletion fragment

<400> SEQUENCE: 61

Asp Ser Thr Ser Asp Leu Ile Pro Ala Pro Pro Leu Ser Lys Val Pro
1               5                   10                  15

Leu Gln Gln Asn Phe Gln Asp Asn Gln Phe
            20                  25

<210> SEQ ID NO 62
<211> LENGTH: 28
<212> TYPE: PRT
<213> ORGANISM: Artificial Sequence
<220> FEATURE:
<223> OTHER INFORMATION: Synthetic PSMA-specific binding protein Frame
      5 C-terminal deletion fragment

<400> SEQUENCE: 62

Leu Lys Glu Asn Phe Ile Arg Phe Ser Lys Ser Leu Gly Leu Pro Glu
1               5                   10                  15

Asn His Ile Val Phe Pro Val Pro Ile Asp Gln Cys
            20                  25

<210> SEQ ID NO 63
<211> LENGTH: 29
<212> TYPE: PRT
<213> ORGANISM: Artificial Sequence
<220> FEATURE:
<223> OTHER INFORMATION: Synthetic PSMA-specific binding protein Frame
      5 C-terminal deletion fragment

<400> SEQUENCE: 63

Leu Lys Glu Asn Phe Ile Arg Phe Ser Lys Ser Leu Gly Leu Pro Glu
1               5                   10                  15
```

```
Asn His Ile Val Phe Pro Val Pro Ile Asp Gln Cys Ile
            20                  25
```

<210> SEQ ID NO 64
<211> LENGTH: 30
<212> TYPE: PRT
<213> ORGANISM: Artificial Sequence
<220> FEATURE:
<223> OTHER INFORMATION: Synthetic PSMA-specific binding protein Frame
      5 C-terminal deletion fragment

<400> SEQUENCE: 64

```
Leu Lys Glu Asn Phe Ile Arg Phe Ser Lys Ser Leu Gly Leu Pro Glu
1               5                   10                  15

Asn His Ile Val Phe Pro Val Pro Ile Asp Gln Cys Ile Asp
            20                  25                  30
```

<210> SEQ ID NO 65
<211> LENGTH: 178
<212> TYPE: PRT
<213> ORGANISM: Artificial Sequence
<220> FEATURE:
<223> OTHER INFORMATION: Synthetic PSMA-specific binding proting
      Anticalin H5

<400> SEQUENCE: 65

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Thr Ala Gly Asn Trp Pro Leu Arg Glu Asp Lys Asp Pro
        35                  40                  45

His Lys Met Ser Ala Thr Ile Tyr Glu Leu Lys Glu Asp Lys Ser Tyr
    50                  55                  60

Asn Val Thr Asn Val Gln Phe Ser Ser Lys Lys Cys Leu Tyr Phe Ile
65                  70                  75                  80

Gly Thr Phe Val Pro Gly Ser Gln Pro Gly Glu Phe Thr Leu Gly Pro
                85                  90                  95

Ile Lys Ser Ala Pro Gly Gln Thr Ser Gly Leu Val Arg Val Val Ser
            100                 105                 110

Thr Asn Tyr Asn Gln His Ala Met Val Phe Phe Lys Gln Val Ile Gln
        115                 120                 125

Asn Arg Glu Ala Phe Ile Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 66
<211> LENGTH: 178
<212> TYPE: PRT
<213> ORGANISM: Artificial Sequence
<220> FEATURE:
<223> OTHER INFORMATION: Synthetic PSMA-specific Anticalin H3

<400> SEQUENCE: 66

```
Gln Asp Ser Thr Ser Asp Leu Ile Pro Ala Pro Pro Leu Ser Lys Val
1               5                   10                  15
```

-continued

```
Pro Leu Gln Gln Asn Phe Gln Asp Asn Gln Phe His Gly Lys Trp Tyr
            20                  25                  30

Val Val Gly Met Ala Gly Asn Met Arg Leu Arg Glu Asp Lys Asp Pro
        35                  40                  45

Phe Lys Met Ser Ala Thr Ile Tyr Glu Leu Lys Glu Asp Lys Ser Tyr
     50                  55                  60

Asn Val Thr Asn Val Arg Phe Trp Tyr Lys Lys Cys Leu Tyr Thr Ile
 65                  70                  75                  80

Ala Thr Phe Val Pro Gly Ser Gln Pro Gly Glu Phe Thr Leu Gly Tyr
                85                  90                  95

Ile Lys Ser Asn Pro Gly Phe Thr Ser Ala Leu Val Arg Val Val Ser
            100                 105                 110

Thr Asn Tyr Asn Gln His Ala Met Val Phe Phe Lys Gln Val Ile Gln
        115                 120                 125

Asn Arg Glu Thr Phe Val Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 67
<211> LENGTH: 178
<212> TYPE: PRT
<213> ORGANISM: Artificial Sequence
<220> FEATURE:
<223> OTHER INFORMATION: Synthetic PSMA-specific Anticalin G6

<400> SEQUENCE: 67

```
Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
            20                  25                  30

Val Val Gly Met Ala Gly Asn Met Arg Leu Arg Glu Asp Lys Asp Pro
        35                  40                  45

Phe Lys Met Ser Ala Thr Ile Tyr Glu Leu Lys Glu Asp Lys Ser Tyr
     50                  55                  60

Asn Val Thr Asn Val Arg Phe Trp Tyr Lys Lys Cys Leu Tyr Thr Ile
 65                  70                  75                  80

Ala Thr Phe Val Pro Gly Ser Gln Pro Gly Glu Phe Thr Leu Gly Tyr
                85                  90                  95

Ile Lys Ser Asn Pro Gly Phe Thr Ser Ala Leu Val Arg Val Val Ser
            100                 105                 110

Thr Asn Tyr Asn Gln His Ala Met Val Phe Phe Lys Gln Val Ile Gln
        115                 120                 125

Asn Arg Glu Thr Phe Val Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

-continued

```
<210> SEQ ID NO 68
<211> LENGTH: 178
<212> TYPE: PRT
<213> ORGANISM: Artificial Sequence
<220> FEATURE:
<223> OTHER INFORMATION: Synthetic PSMA-specific Anticalin G4

<400> SEQUENCE: 68

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly His Ala Gly Asn Met Leu Leu Arg Glu Asp Lys Asp Pro
        35                  40                  45

Ser Lys Met Val Ala Thr Ile Tyr Glu Leu Lys Glu Asp Lys Ser Tyr
    50                  55                  60

Asn Val Thr Gln Val Asp Phe Gly Thr Lys Lys Cys Phe Tyr Ala Ile
65                  70                  75                  80

Asn Thr Phe Val Pro Gly Ser Gln Pro Gly Glu Phe Thr Leu Gly His
                85                  90                  95

Ile Lys Ser Asn Pro Gly Met Thr Ser Met Leu Val Arg Val Val Ser
            100                 105                 110

Thr Asn Tyr Asn Gln His Ala Met Val Phe Phe Lys Ala Val Leu Gln
        115                 120                 125

Asn Arg Glu Gly Phe Leu Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 69
<211> LENGTH: 178
<212> TYPE: PRT
<213> ORGANISM: Artificial Sequence
<220> FEATURE:
<223> OTHER INFORMATION: Synthetic PSMA-specific Anticalin A2

<400> SEQUENCE: 69

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Arg Ala Gly Asn Lys Pro Leu Arg Glu Asp Lys Asp Pro
        35                  40                  45

Leu Lys Met Trp Ala Thr Ile Tyr Glu Leu Lys Glu Asp Lys Ser Tyr
    50                  55                  60

Asn Val Thr Ile Val Trp Phe Asp Phe Lys Lys Cys Trp Tyr Arg Ile
65                  70                  75                  80

Ser Thr Phe Val Pro Gly Ser Gln Pro Gly Glu Phe Thr Leu Gly Arg
                85                  90                  95

Ile Lys Ser Ala Pro Gly Val Thr Ser Gly Leu Val Arg Val Val Ser
            100                 105                 110

Thr Asn Tyr Asn Gln His Ala Met Val Phe Phe Lys Tyr Val Phe Gln
        115                 120                 125

Asn Arg Glu Trp Phe His Ile Thr Leu Tyr Gly Arg Thr Lys Glu Leu
```

```
                130             135             140
Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

```
<210> SEQ ID NO 70
<211> LENGTH: 534
<212> TYPE: DNA
<213> ORGANISM: Artificial Sequence
<220> FEATURE:
<221> NAME/KEY: source
<222> LOCATION: 1..534
<223> OTHER INFORMATION: /mol_type="unassigned DNA"
      /note="Synthetic PSMA-specific Anticalin H5"
      /organism="Artificial Sequence"

<400> SEQUENCE: 70
caggactcca cctcagacct gatcccagcc ccacctctga gcaaggtccc tctgcagcag      60
aacttccagg acaaccaatt ccatgggaaa tggtatgtcg tgggcaccgc cggaaattgg     120
cctctgcgtg aggataagga tccgcacaaa atgagcgcga ccatttacga gttgaaagaa     180
gataaatcat ataacgtcac caatgtgcaa tttagcagca agaaatgcct gtacttcatt     240
ggaacctttg tgccggggag ccagccgggc gagtttactt taggccctat aaaaagtgca     300
ccgggccaaa catcaggatt ggtccgcgtc gtgagcacca actacaacca gcatgccatg     360
gtgttcttca gcaagtgat ccagaaccgc gaggcattta tcatcacact gtacgggcgc      420
acgaaagaac tgacaagcga gctgaaggaa aattttatcc gcttttccaa atctctgggc     480
ctccctgaaa accacatcgt cttccctgtc ccaatcgacc agtgtatcga cggc            534
```

```
<210> SEQ ID NO 71
<211> LENGTH: 534
<212> TYPE: DNA
<213> ORGANISM: Artificial Sequence
<220> FEATURE:
<221> NAME/KEY: source
<222> LOCATION: 1..534
<223> OTHER INFORMATION: /mol_type="unassigned DNA"
      /note="Synthetic PSMA-specific Anticalin H3"
      /organism="Artificial Sequence"

<400> SEQUENCE: 71
caggactcca cctcagacct gatcccagcc ccacctctga gcaaggtccc tctgcagcag      60
aacttccagg acaaccaatt ccatgggaaa tggtatgtcg tgggcatggc cggaaatatg     120
cgtctgcgtg aggataagga tccgttcaaa atgagcgcga ccatttacga gttgaaagaa     180
gataaatcat atacgtcac caatgtgcgt ttttggtaca agaaatgcct gtacaccatt      240
gcaacctttg tgccggggag ccagccgggc gagtttactt taggctacat aaaaagtaat     300
ccgggcttca catcagcatt ggtccgcgtc gtgagcacca actacaacca gcatgccatg     360
gtgttcttca gcaagtgat ccagaaccgc gagacctttg ttatcacact gtacgggcgc      420
acgaaagaac tgacaagcga gctgaaggaa aattttatcc gcttttccaa atctctgggc     480
ctccctgaaa accacatcgt cttccctgtc ccaatcgacc agtgtatcga cggc            534
```

```
<210> SEQ ID NO 72
<211> LENGTH: 534
<212> TYPE: DNA
<213> ORGANISM: Artificial Sequence
```

<220> FEATURE:
<221> NAME/KEY: source
<222> LOCATION: 1..534
<223> OTHER INFORMATION: /mol_type="unassigned DNA"
    /note="Synthetic PSMA-specific Anticalin G6"
    /organism="Artificial Sequence"

<400> SEQUENCE: 72

```
caggactcca cctcagacct gatcccagcc ccacctctga gcaaggtccc tctgcagcag      60
aacttccagg acaaccaatt ccatgggaaa tggtatgtcg tgggcatggc cggaaatatg     120
cgtctgcgtg aggataagga tccgttcaaa atgagcgcga ccatttacga gttgaaagaa     180
gataaatcat ataacgtcac caatgtgcgt ttttggtaca agaaatgcct gtacaccatt     240
gcaacctttg tgccggggag ccagccgggc gagtttactt taggctacat taaaagtaat     300
ccgggcttca catcagcatt ggtccgcgtc gtgagcacca actacaacca gcatgccatg     360
gtgttcttca agcaagtgat ccagaaccgc gagacctttg ttatcacact gtacgggcgc     420
acgaaagaac tgacaagcga gctgaaggaa aattttatcc gcttttccaa atctctgggc     480
ctccctgaaa accacatcgt cttccctgtc ccaatcgacc agtgtatcga cggc           534
```

<210> SEQ ID NO 73
<211> LENGTH: 534
<212> TYPE: DNA
<213> ORGANISM: Artificial Sequence
<220> FEATURE:
<221> NAME/KEY: source
<222> LOCATION: 1..534
<223> OTHER INFORMATION: /mol_type="unassigned DNA"
    /note="Synthetic PSMA-specific Anticalin G4"
    /organism="Artificial Sequence"

<400> SEQUENCE: 73

```
caggactcca cctcagacct gatcccagcc ccacctctga gcaaggtccc tctgcagcag      60
aacttccagg acaaccaatt ccatgggaaa tggtatgtcg tgggccacgc cggaaatatg     120
ctgctgcgtg aggataagga tccgagcaaa atggttgcga ccatttacga gttgaaagaa     180
gataaatcat ataacgtcac ccaagtggac tttggaacta agaaatgctt ctacgcaatt     240
aatacctttg tgccggggag ccagccgggc gagtttactt taggccacat taaaagtaat     300
ccgggcatga catcaatgtt ggtccgcgtc gtgagcacca actacaacca gcatgccatg     360
gtgttcttca aggcagtgct gcagaaccgc gagggatttc tgatcacact gtacgggcgc     420
acgaaagaac tgacaagcga gctgaaggaa aattttatcc gcttttccaa atctctgggc     480
ctccctgaaa accacatcgt cttccctgtc ccaatcgacc agtgtatcga cggc           534
```

<210> SEQ ID NO 74
<211> LENGTH: 534
<212> TYPE: DNA
<213> ORGANISM: Artificial Sequence
<220> FEATURE:
<221> NAME/KEY: source
<222> LOCATION: 1..534
<223> OTHER INFORMATION: /mol_type="unassigned DNA"
    /note="Synthetic PSMA-specific Anticalin A2"
    /organism="Artificial Sequence"

<400> SEQUENCE: 74

```
caggactcca cctcagacct gatcccagcc ccacctctga gcaaggtccc tctgcagcag      60
aacttccagg acaaccaatt ccatgggaaa tggtatgtcg tgggccgtgc cggaaataaa     120
cctctgcgtg aggataagga tccgctgaaa atgtgggcga ccatttacga gttgaaagaa     180
```

```
gataaatcat ataacgtcac catcgtgtgg tttgacttca agaaatgctg gtaccgtatt      240
agcacctttg tgccggggag ccagccgggc gagtttactt taggccgtat taaaagtgca      300
ccgggcgtta catcaggatt ggtccgcgtc gtgagcacca actacaacca gcatgccatg      360
gtgttcttca agtacgtgtt ccagaaccgc gagtggtttc acatcacact gtacgggcgc      420
acgaaagaac tgacaagcga gctgaaggaa aattttatcc gcttttccaa atctctgggc      480
ctccctgaaa accacatcgt cttccctgtc ccaatcgacc agtgtatcga cggc            534
```